United States Patent
Hassan et al.

(10) Patent No.: US 9,592,484 B2
(45) Date of Patent: Mar. 14, 2017

(54) GASIFICATION OF CARBONACEOUS MATERIALS AND GAS TO LIQUID PROCESSES

(71) Applicant: H R D Corporation, Sugar Land, TX (US)

(72) Inventors: Abbas Hassan, Sugar Land, TX (US); Aziz Hassan, Sugar Land, TX (US); Rayford G. Anthony, College Station, TX (US); Gregory G. Borsinger, Chatham, NJ (US)

(73) Assignee: HRD Corporation, Houston, TX (US)

( * ) Notice: Subject to any disclaimer, the term of this patent is extended or adjusted under 35 U.S.C. 154(b) by 546 days.

(21) Appl. No.: 13/753,224

(22) Filed: Jan. 29, 2013

(65) Prior Publication Data

US 2013/0142706 A1 Jun. 6, 2013

Related U.S. Application Data

(60) Division of application No. 13/495,954, filed on Jun. 13, 2012, now Pat. No. 8,497,309, which is a
(Continued)

(51) Int. Cl.
*B01J 8/02* (2006.01)
*B01J 8/22* (2006.01)
(Continued)

(52) U.S. Cl.
CPC ........... *B01J 8/008* (2013.01); *B01F 7/00766* (2013.01); *B01F 7/00791* (2013.01);
(Continued)

(58) Field of Classification Search
None
See application file for complete search history.

(56) References Cited

U.S. PATENT DOCUMENTS

| | | | |
|---|---|---|---|
| 3,632,503 A | 1/1972 | Hayes et al. | |
| 3,755,481 A | 8/1973 | Hayes et al. | |

(Continued)

FOREIGN PATENT DOCUMENTS

| | | |
|---|---|---|
| CA | 2690107 | 11/2012 |
| CN | 101668725 | 3/2010 |

(Continued)

OTHER PUBLICATIONS

Eurasian Office Action dated Apr. 16, 2014 for corresponding Eurasian Application No. 201000062/13 (3 pgs.).
(Continued)

*Primary Examiner* — Jennifer A Leung
(74) *Attorney, Agent, or Firm* — Timothy S. Westby; Porter Hedges LLP

(57) ABSTRACT

Herein disclosed is a system for producing an organic, the system including at least one high shear mixing device having at least one rotor and at least one stator separated by a shear gap, wherein the shear gap is the minimum distance between the at least one rotor and the at least one stator; a pump configured for delivering a fluid stream comprising liquid medium and light gas to the at least one high shear mixing device, wherein the at least one high shear mixing device is configured to form a dispersion of the light gas in the liquid medium; and a reactor comprising at least one inlet and at least one outlet, wherein the at least one inlet of the reactor is fluidly connected to the at least one high shear mixing device, and wherein the at least one outlet is configured for extracting the organic therefrom.

25 Claims, 8 Drawing Sheets

Related U.S. Application Data continuation of application No. 12/844,728, filed on Jul. 27, 2010, now Pat. No. 8,394,861, which is a continuation-in-part of application No. 12/140,763, filed on Jun. 17, 2008, now Pat. No. 8,026,403, which is a continuation-in-part of application No. 12/138,269, filed on Jun. 12, 2008, now Pat. No. 8,133,925.

(60) Provisional application No. 61/231,261, filed on Aug. 4, 2009, provisional application No. 61/039,235, filed on Mar. 25, 2008, provisional application No. 60/946,444, filed on Jun. 27, 2007, provisional application No. 60/946,468, filed on Jun. 27, 2007.

(51) Int. Cl.
| | |
|---|---|
| C07C 1/04 | (2006.01) |
| B01J 8/00 | (2006.01) |
| B01F 7/00 | (2006.01) |
| B01F 13/10 | (2006.01) |
| B01J 19/18 | (2006.01) |
| C10G 2/00 | (2006.01) |
| C10J 3/00 | (2006.01) |
| C01B 3/38 | (2006.01) |
| C10J 3/48 | (2006.01) |

(52) U.S. Cl.
CPC ...... *B01F 13/1013* (2013.01); *B01F 13/1016* (2013.01); *B01J 8/222* (2013.01); *B01J 19/1806* (2013.01); *B01J 19/1862* (2013.01); *C01B 3/38* (2013.01); *C07C 1/041* (2013.01); *C07C 1/0405* (2013.01); *C07C 1/0415* (2013.01); *C10G 2/341* (2013.01); *C10G 2/342* (2013.01); *C10G 2/344* (2013.01); *C10G 2/35* (2013.01); *C10J 3/00* (2013.01); *B01J 2208/0053* (2013.01); *B01J 2208/00823* (2013.01); *B01J 2208/00876* (2013.01); *B01J 2219/00083* (2013.01); *B01J 2219/00159* (2013.01); *C01B 2203/0233* (2013.01); *C01B 2203/0283* (2013.01); *C01B 2203/061* (2013.01); *C01B 2203/062* (2013.01); *C01B 2203/1247* (2013.01); *C10G 2300/107* (2013.01); *C10G 2300/1014* (2013.01); *C10G 2300/1025* (2013.01); *C10G 2300/1033* (2013.01); *C10G 2300/1077* (2013.01); *C10G 2300/42* (2013.01); *C10J 2300/093* (2013.01); *C10J 2300/0906* (2013.01); *C10J 2300/0926* (2013.01); *C10J 2300/0986* (2013.01); *C10J 2300/0989* (2013.01); *C10J 2300/1656* (2013.01); *C10J 2300/1659* (2013.01); *Y02P 20/582* (2015.11); *Y02P 30/20* (2015.11)

(56) References Cited

U.S. PATENT DOCUMENTS

| | | | |
|---|---|---|---|
| 3,878,131 A | 4/1975 | Hayes et al. | |
| 3,887,167 A | 6/1975 | Irwin | |
| 3,894,107 A | 7/1975 | Butter et al. | |
| 3,988,329 A * | 10/1976 | Zucker | 554/144 |
| 4,206,713 A | 6/1980 | Ryason | |
| 4,543,434 A | 9/1985 | Chang et al. | |
| 4,551,444 A | 11/1985 | Lin et al. | |
| 4,670,472 A * | 6/1987 | Dyer et al. | 518/700 |
| 4,684,618 A * | 8/1987 | Foley et al. | 502/313 |
| 4,752,600 A * | 6/1988 | Fiato et al. | 502/325 |
| 4,857,076 A * | 8/1989 | Pearson | C10J 3/506 239/132.3 |
| 4,931,225 A | 6/1990 | Cheng | |
| 5,233,113 A | 8/1993 | Periana et al. | |
| 5,344,849 A * | 9/1994 | Ayasse | C07C 1/0435 518/713 |
| 5,427,992 A * | 6/1995 | Graefe et al. | 502/111 |
| 5,538,191 A | 7/1996 | Holl et al. | |
| 5,597,044 A | 1/1997 | Roberts et al. | |
| 5,659,090 A | 8/1997 | Cameron et al. | |
| 5,844,005 A | 12/1998 | Bauman et al. | |
| 5,877,350 A | 3/1999 | Langer et al. | |
| 6,096,789 A | 8/2000 | Clerici et al. | |
| 6,147,126 A | 11/2000 | DeGeorge et al. | |
| 6,262,131 B1 | 7/2001 | Arcuri et al. | |
| 6,368,366 B1 | 4/2002 | Langer et al. | |
| 6,380,444 B1 | 4/2002 | Bjerrum et al. | |
| 6,383,237 B1 | 5/2002 | Langer et al. | |
| 6,530,964 B2 | 3/2003 | Langer et al. | |
| 6,600,000 B1 | 7/2003 | Ooura et al. | |
| 6,742,774 B2 | 6/2004 | Holl | |
| 6,752,529 B2 | 6/2004 | Holl | |
| 6,822,007 B2 | 11/2004 | Ketley et al. | |
| 6,868,366 B1 | 3/2005 | Eisenzopf | |
| 6,924,316 B2 | 8/2005 | Iwamoto et al. | |
| 7,165,881 B2 | 1/2007 | Holl et al. | |
| 7,282,603 B2 | 10/2007 | Richards et al. | |
| 7,538,237 B2 | 5/2009 | Holl et al. | |
| 7,556,679 B2 | 7/2009 | Lee et al. | |
| 7,575,728 B2 | 8/2009 | Holl et al. | |
| 7,833,512 B2 | 11/2010 | Pulkrabek et al. | |
| 7,884,250 B2 * | 2/2011 | Hassan et al. | 568/458 |
| 7,888,535 B2 * | 2/2011 | Hassan et al. | 568/476 |
| 7,910,068 B2 * | 3/2011 | Hassan et al. | 422/129 |
| 7,910,069 B2 * | 3/2011 | Hassan et al. | 422/129 |
| 7,910,758 B2 * | 3/2011 | Hassan et al. | 554/169 |
| 7,914,744 B2 * | 3/2011 | Hassan et al. | 422/129 |
| 7,914,745 B2 * | 3/2011 | Hassan et al. | 422/129 |
| 8,026,402 B2 * | 9/2011 | Hassan et al. | 585/270 |
| 8,026,403 B2 | 9/2011 | Hassan et al. | |
| 8,133,447 B2 * | 3/2012 | Hassan et al. | 422/225 |
| 8,133,925 B2 | 3/2012 | Hassan et al. | |
| 8,147,768 B2 * | 4/2012 | Hassan et al. | 422/225 |
| 8,349,269 B2 * | 1/2013 | Hassan et al. | 422/225 |
| 8,349,861 B2 | 1/2013 | Hassan et al. | |
| 8,371,741 B2 * | 2/2013 | Hassan et al. | 366/101 |
| 8,394,861 B2 | 3/2013 | Hassan et al. | |
| 8,426,653 B2 * | 4/2013 | Hassan et al. | 568/884 |
| 8,445,672 B2 * | 5/2013 | Hassan et al. | 536/124 |
| 8,480,961 B2 * | 7/2013 | Hassan et al. | 422/129 |
| 8,491,856 B2 * | 7/2013 | Hassan et al. | 422/606 |
| 8,771,605 B2 * | 7/2014 | Hassan et al. | 422/225 |
| 2001/0051588 A1 * | 12/2001 | Herron et al. | 502/302 |
| 2004/0122114 A1 | 6/2004 | Font Freide et al. | |
| 2004/0132836 A1 * | 7/2004 | Font Freide et al. | 518/726 |
| 2004/0147621 A1 | 7/2004 | Font Freide et al. | |
| 2004/0157941 A1 | 8/2004 | Font Freide et al. | |
| 2004/0180976 A1 | 9/2004 | Hensman et al. | |
| 2005/0053532 A1 | 3/2005 | Holl | |
| 2006/0102519 A1 | 5/2006 | Tonkovich et al. | |
| 2006/0254956 A1 | 11/2006 | Khan | |
| 2007/0149392 A1 | 6/2007 | Ku | |
| 2007/0186472 A1 | 8/2007 | Rabovitser et al. | |
| 2008/0281001 A1 | 11/2008 | Wood et al. | |
| 2008/0281136 A1 | 11/2008 | Bagherzadeh et al. | |
| 2009/0003126 A1 | 1/2009 | Hassan et al. | |
| 2009/0005587 A1 | 1/2009 | Hassan et al. | |
| 2009/0075364 A1 | 3/2009 | Fabiyi et al. | |
| 2009/0158663 A1 * | 6/2009 | Deluga | C10J 3/463 48/209 |
| 2009/0205488 A1 | 8/2009 | Betting et al. | |
| 2010/0317748 A1 | 12/2010 | Hassan et al. | |
| 2010/0329944 A1 | 12/2010 | Hassan et al. | |
| 2012/0252908 A1 | 10/2012 | Hassan et al. | |

FOREIGN PATENT DOCUMENTS

| | | |
|---|---|---|
| DE | 4235558 | 5/1994 |
| EA | 005789 | 6/2005 |
| EP | 0442300 | 8/1991 |
| EP | 1558353 | 8/2005 |
| FR | 2825996 | 12/2002 |
| JP | 3197504 | 8/1991 |

(56) References Cited

FOREIGN PATENT DOCUMENTS

| | | |
|---|---|---|
| JP | 8506998 | 8/1994 |
| JP | H08506998 | 7/1996 |
| JP | 2004534874 | 5/2002 |
| JP | 2004534874 | 11/2004 |
| JP | 2010515073 | 5/2010 |
| JP | 5579601 | 9/2010 |
| NG | NG/C/2009/633 | 12/2011 |
| WO | 9402772 | 12/1994 |
| WO | 9427722 | 12/1994 |
| WO | 0138269 | 5/2001 |
| WO | 02064708 | 8/2002 |
| WO | 02096836 | 12/2002 |
| WO | 02096837 | 12/2002 |
| WO | 03041848 | 5/2003 |
| WO | 2004041399 | 5/2004 |

OTHER PUBLICATIONS

Office Action dated Jun. 4, 2014 for corresponding U.S. Appl. No. 13/366,245 (19 pgs.).
Eurasian Office Action dated Jun. 7, 2013 for corresponding Eurasian Patent Application No. 201000062/13 (2 pgs.).
Notice of Allowance dated Jun. 7, 2013 for corresponding U.S. Appl. No. 13/495,954 (15 pgs.).
Eurasian Office Action dated Jun. 25, 2013 for corresponding Eurasian Patent Application No. 200901336/13 (2 pgs.).
Gulf Cooperation Council Search Report dated Jun. 2, 2014 for corresponding GCC Application No. GCC/P/2008/11149 (7 pgs.).
Chinese Office Action dated Jul. 7, 2014 for corresponding Chinese Application No. 201080034661.6 (10 pgs.).
European Examination Report dated Jul. 1, 2013 for corresponding European Patent Application No. 08771780.7 (2 pgs.).
Chinese Office Action dated Jun. 4, 2013 for corresponding Chinese Patent Application No. 201080034661.6 (3 pgs.).
Japanese Office Action dated Jul. 11, 2013 for corresponding Japanese Patent Application No. 2010-515073 (5 pgs.).
Japanese Office Action dated Jul. 9, 2013 for corresponding Japanese Patent Application No. 2010-515073 (5 pgs.).
Chinese Office Action dated Aug. 5, 2013 for corresponding Chinese Patent Application No. 200880013603.8 (9 pgs.).
Eurasian Office Action dated Oct. 7, 2013 for corresponding Eurasian Patent Application No. 201000062/13 (4 pgs.).
Eurasian Office Action dated Oct. 4, 2013 for corresponding Eurasian Patent Application No. 200901336/13 (2 pgs.).
India Examination Report dated Sep. 19, 2013 for corresponding India Patent Application No. 5504/DELNP/2009 (2 pgs.).
Australian Examination Report dated Nov. 18, 2013 for corresponding Australian Patent Application No. 2010281384 (3 pgs.).
European Examination Report dated Nov. 7, 2013 for corresponding European Patent Application No. 10806922.0 (10 pgs.).
Office Action dated Mar. 28, 2014 for corresponding U.S. Appl. No. 12/874,442 (62 pgs.).
Eurasian Office Action dated May 20, 2014 for corresponding Eurasian Application No. 201290039/31 (6 pgs.).
Eurasian Office Action dated Jun. 21, 2012 for corresponding Eurasian Application No. 200901336 (4 pgs.).
Search Report dated Aug. 28, 2008 for corresponding International Application No. PCT/US2008/068174 (2 pgs.).
GCC Search Report dated Sep. 8, 2011 for corresponding GCC Application No. GCC/P/2008/11165 (6 pgs.).
Canadian Office Action dated Aug. 9, 2011 for corresponding Canadian Application No. 2690107 (3 pgs.).
Chinese Office Action dated Jul. 13, 2011 for corresponding Chinese Application No. 200880021961.3 (9 pgs.).
Chinese Office Action dated Jun. 29, 2012 for corresponding Chinese Application No. 200880021961.3 (6 pgs.).
Eurasian Office Action dated Jun. 1, 2012 for corresponding Eurasian Application No. 201000062 (4 pgs.).
Japanese Office Action dated Aug. 21, 2012 for corresponding Japanese Application No. 2010515073 (2 pgs.).
Canadian Office Action dated Apr. 10, 2012 for corresponding Canadian Application No. 2768032 (1 pg.).
Japanese Office Action dated Feb. 18, 2014 for corresponding Japanese Application No. 2010 515073 (2 pgs.).
European Search Report dated Feb. 3, 2014 for corresponding European Patent Application No. 08771917.5-1361 (8 pgs.).
Chinese Office Action dated Feb. 27, 2014 for corresponding Chinese Application No. 200880013603.8 (7 pgs.).
IKA-DRS Reactors website http://www.ikausa.com/dr.him, on Sep. 8, 2010 (2 pgs.).
IKA, "Introduction to IKA's Three Stage Dispax Reactor," Retrieved from <http://www.ikausa.com/pdfs/process/dr%202000-Homogenizing-Dispersing-Suspending-Emulsifying,pdf> on Aug. 22, 2012 (12 pgs.).
Office Action dated Jan. 2, 2013 for corresponding U.S. Appl. No. 13/366,245 (17 pgs.).
Office Action dated Aug. 29, 2012 for corresponding U.S. Appl. No. 13/366,245 (13 pgs.).
Office Action dated Jul. 25, 2012 for corresponding U.S. Appl. No. 12/844,728 (7 pgs.).
Australian Office Action dated Nov. 15, 2012 for corresponding Australian Application No. 2010281384 (5 pgs.).
Office Action dated Dec. 5, 2012 for corresponding U.S. Appl. No. 12/844,728 (5 pgs.).
Notice of Allowance dated Jan. 7, 2013 for corresponding U.S. Appl. No. 12/844,728 (8 pgs.).
Search Report and Written Opinion dated May 2, 2011 for corresponding International Application No. PCT/US2010/043532 (9 pgs.).
Eurasian Office Action dated Sep. 21, 2012 for corresponding Eurasian Application No. 201290039 (3 pgs.).
Eurasian Office Action dated Aug. 13, 2012 for corresponding Eurasian Application No. 201290039 (3 pgs.).
Office Action dated Feb. 24, 2011 for U.S. Appl. No. 12/796,358 (13 pgs.).
Office Action dated Feb. 29, 2012 for U.S. Appl. No. 12/146,733 (8 pgs.).
Office Action dated Jun. 3, 2011 for U.S. Appl. No. 12/568,155 (11 pgs.).
Notice of Allowance dated Jun. 1, 2011 for corresponding U.S. Appl. No. 12/140,763 (8 pgs.).
Notice of Allowance dated Nov. 14, 2011 for corresponding U.S. Appl. No. 12/138,269 (7 pgs.).
Office Action dated Nov. 15, 2010 for corresponding U.S. Appl. No. 12/140,763 (7 pgs.).
Office Action dated Jun. 9, 2011 for corresponding U.S. Appl. No. 12/138,269 (8 pgs.).
Office Action dated Jun. 2, 2011 for U.S. Appl. No. 12/427,286 (12 pgs.).
Office Action dated Jun. 3, 2011 for U.S. Appl. No. 12/568,280 (16 pgs.).
Search Report and Written Opinion dated Oct. 13, 2008 for corresponding International Application No. PCT/US2008/067970 (11 pgs.).
IKA-Rotor Stator Generators, dated 2003 Processing Catalog (38 pgs.).
Gogate, et al. "Cavitation: A technology on the horizon," Current Science 91, No. 1, Jul. 2006, pp. 35-46 (12 pgs.).
Eurasian Office Action dated Apr. 3, 2013 for corresponding Eurasian Application No. 201000062/13 (2 pgs.).
Office Action dated Mar. 13, 2013 for corresponding U.S. Appl. No. 13/495,954 (11 pgs.).
Notice of Allowance dated Oct. 30, 2012 for corresponding Canadian Application No. 2,768,032 (1 pg.).
Notice of Grant dated Feb. 18, 2013 for corresponding Chinese Application No. 200880021961.3 (4 pg.).
Notice of Allowance dated Dec. 3, 2012 for corresponding Canadian Application No. 2,679,470 (1 pg.).
Chinese Office Action dated Apr. 3, 2013 for corresponding Chinese Application No. 200880013603.8 (9 pgs.).

(56) References Cited

OTHER PUBLICATIONS

Canadian Office Action dated Mar. 28, 2012 for corresponding Canadian Application No. 2679470 (2 pgs.).
Canadian Office Action dated Mar. 25, 2011 for corresponding Canadian Application No. 2679470 (3 pgs.).
Chinese Office Action dated Mar. 15, 2011 for corresponding Chinese Application No. 200880020903.9 (9 pgs.).
European Search Report dated Apr. 12, 2011 for corresponding European Application No. 08771880.7 (6 pgs.).
Office Action dated Jun. 25, 2009 for U.S. Appl. No. 12/142,447 (10 pgs.).
Office Action dated Jan. 7, 2010 for U.S. Appl. No. 12/142,447 (6 pgs.).
Office Action dated May 13, 2010 for U.S. Appl. No. 12/142,447 (5 pgs.).
Office Action dated Feb. 4, 2010 for U.S. Appl. No. 12/492,721 (5 pgs.).
Office Action dated Feb. 18, 2010 for U.S. Appl. No. 12/635,433 (6 pgs.).
Office Action dated Feb. 18, 2010 for U.S. Appl. No. 12/635,454 (6 pgs.).
Office Action dated May 14, 2010 for U.S. Appl. No. 12/137,441 (15 pgs.).
Office Action dated Feb. 19, 2010 for U.S. Appl. No. 12/144,459 (10 pgs.).
Office Action dated Sep. 2, 2009 for U.S. Appl. No. 12/142,433 (11 pgs.).
Office Action dated Jan. 29, 2010 for U.S. Appl. No. 12/142,433 (8 pgs.).
Office Action dated May 24, 2011 for U.S. Appl. No. 12/142,433 (10 pgs.).
Office Action dated Apr. 30, 2010 for U.S. Appl. No. 12/141,191 (12 pgs.).
Office Action dated Oct. 27, 2009 for U.S. Appl. No. 12/142,120 (15 pgs.).
Office Action dated May 5, 2010 for U.S. Appl. No. 12/571,537 (12 pgs.).
Chinese dated Jan. 13, 2014 for corresponding Chinese Patent Application No. 201080034661.6 (8 pgs.).
GCC Examination Report dated Nov. 28, 2013 for corresponding GCC Patent Application No. GC 2010-16448 (4 pgs.).
Indonesian Examination Report dated Nov. 25, 2013 for corresponding India Patent Application No. 7959/DELNP/2009 (2 pgs.).
Chinese Office Action dated Dec. 3, 2014 for corresponding Chinese Application No. 200880013603.8 (13 pgs.).
Office Action dated Nov. 5, 2014 for corresponding U.S. Appl. No. 13/366,245 (19 pgs.).
Office Action dated Dec. 17, 2014 for corresponding U.S. Appl. No. 12/874,442 (11 pgs.).
Chinese Office Action dated Mar. 20, 2015 for corresponding Chinese Application No. 200880013603.8 (14 pgs.).
Eurasia Office Action dated Feb. 19, 2015 for corresponding Eurasia Application No. 201290039 (5 pgs.).
GCC Examination Report dated Dec. 14, 2014 for corresponding GCC Application No. GCC/P/2008/11149 (4 pgs.).
Japan Office Action dated Jan. 13, 2015 for corresponding Japan Application No. 2013-232069 (5 pgs.).
Office Action dated May 20, 2015 for corresponding U.S. Appl. No. 12/874,442, 16 pgs.
Office Action dated Jun. 4, 2014 for counterpart U.S. Appl. No. 13/366,245; 52 pages.
Office Action dated Mar. 27, 2015 for counterpart EA Application No. 201290039; 4 pages.
Office Action dated Dec. 4, 2015 for counterpart AU Application No. 2014200169; 4 pages.
Office Action dated Aug. 27, 2015 for counterpart EP Application No. 10806922.0; 4 pages.

\* cited by examiner

GASIFICATION OF CARBONACEOUS MATERIALS AND GAS TO LIQUID PROCESSES

CROSS-REFERENCE TO RELATED APPLICATIONS

This application is a divisional application of U.S. patent application Ser. No. 13/495,954 (now U.S. Pat. No. 8,497,309), filed Jun. 13, 2012; U.S. patent application Ser. No. 13/495,954 (now U.S. Pat. No. 8,497,309) is a continuation of U.S. patent application Ser. No. 12/844,728 (now U.S. Pat. No. 8,394,861), filed Jul. 27, 2010; U.S. patent application Ser. No. 12/844,328 (now U.S. Pat. No. 8,394,861) claims the benefit under 35 U.S.C. §119(e) of U.S. Provisional Patent Application No. 61/231,261, filed Aug. 4, 2009, and is a continuation-in-part of U.S. patent application Ser. No. 12/140,763 (now U.S. Pat. No. 8,026,403, filed Jun. 17, 2008, and is also a continuation-in-part of U.S. patent application Ser. No. 12/138,269 (now U.S. Pat. No. 8,133,925), filed Jun. 12, 2008; U.S. patent application Ser. No. 12/140,763 (now U.S. Pat. No. 8,026,403) claims the benefit under 35 U.S.C. §119(e) of U.S. Provisional Patent Application No. 60/946,444, filed Jun. 27, 2007, and U.S. Provisional Patent Application No. 61/039,235, filed Mar. 25, 2008; U.S. patent application Ser. No. 12/138,269 (now U.S. Pat. No. 8,133,925) claims the benefit under 35 U.S.C. §119(e) of U.S. Provisional Patent Application No. 60/946,468, filed Jun. 27, 2007. The disclosure of each of the aforementioned applications is hereby incorporated herein by reference.

STATEMENT REGARDING FEDERALLY SPONSORED RESEARCH OR DEVELOPMENT

Not Applicable.

BACKGROUND OF THE INVENTION

Technical Field

The present invention generally relates to the production of syngas from hydrocarbon sources such as coal, peat, coke, methane, biogas, coker gas and other hydrocarbon sources. The present application also relates to conversion of light gases (such as carbon monoxide, carbon dioxide, methane, hydrogen, and/or water) into hydrocarbons and/or liquid oxygenates. The invention relates more particularly to apparatus and methods for producing liquid oxygenates and/or hydrocarbons using high shear.

Background of the Invention

The effect of increasing carbon dioxide emission on global warming is a major concern of scientists and governments due to its effect on the environment. The increased use of fossil fuels as a source of power and heat is the main reason for the increase in carbon dioxide emissions. The combustion of fossil fuels is an exothermic process where the energy released is typically used for heating and/or conversion to other forms of energy such as mechanical energy. Oxidation of hydrocarbons is also common practice in chemical reactions such as oxidation of ethylene, Fischer Tropsch and other reactions. The resulting effluent from combustion of hydrocarbon depends on the make up of the hydrocarbon but is mainly carbon dioxide and water. Releasing large amounts of carbon dioxide into the atmosphere is believed to be responsible for adverse effects to the environment and there are efforts underway to reduce carbon dioxide emissions to help abate these negative effects.

A viable solution to the deleterious environmental effects of carbon dioxide emissions should result in a net reduction of carbon dioxide emissions. Technologies to sequester carbon dioxide can consume large amounts of energy, the energy, in many cases, derived from fossil fuels, and thus resulting in little or no net reduction in carbon dioxide, or worse yet a net increase in carbon dioxide production.

A process that allows recycling carbon dioxide to produce a valuable product such as fuel or chemical feedstock would be of great benefit in reducing the purported effects of carbon dioxide on global warming. It would be additionally beneficial to develop a process to convert carbon dioxide into a liquid fuel that can be transported and/or used as a feedstock for refinery or petrochemical processes.

Methane is an important building block in organic reactions used in industry as well as an important fuel source. The methane content of natural gas may vary within the range of from about 40 volume percent to about 95 volume percent. Other constituents of natural gas may include ethane, propane, butanes, pentane (and heavier hydrocarbons), hydrogen sulfide, carbon dioxide, helium and nitrogen. Natural gas in liquid form has a density of 0.415 and a boiling point of minus 162° C. It is therefore not readily adaptable to transport as a liquid except for marine transport in very large tanks with a low surface to volume ratio. Large-scale use of natural gas often requires a sophisticated and extensive pipeline system. A significant portion of the known natural gas reserves is associated with remote fields, to which access is difficult. For many of these remote fields, pipelining to bring the gas to potential users is not economically feasible. Economically transporting methane from remote areas by converting the gas to a liquid has long been sought in the industry.

Indirectly converting methane to methanol by steam-reforming to produce synthesis gas as a first step, followed by catalytic synthesis of methanol is a well-known process. Aside from the technical complexity and the high cost of this two-step, indirect synthesis, the methanol product has a limited market and the process thus does not appear to offer a practical way to utilize natural gas from remote fields.

A process that provides an effective means for catalytically converting methanol to gasoline is described in U.S. Pat. No. 3,894,107 (Butter et al.). Although the market for gasoline is large relative to the market for methanol, and although this process was used in New Zealand, it is complex and its viability appears to be limited to situations in which the cost for supplying an alternative source of gasoline is high. Because of the high cost of producing gasoline from this process, it was shut down.

Attempts to carry out the partial oxidation of methane to liquid compounds (such as methanol or ethanol) in the gas phase have met with limited success because of difficulties in controlling the free radical processes that are involved. Since methanol is more reactive than methane, the undesirable formation of CO and $CO_2$ via secondary combustion has been unavoidable. While a variety of catalysts, mostly metal oxides, have been reported for the partial oxidation of methane to methanol, the reaction has required high temperatures and the reported methanol yields based on methane have generally been less than 10%.

Other approaches for the conversion of methane to methanol have been reported by Bjerrum, U.S. Pat. No. 6,380,444; Periana, U.S. Pat. No. 5,233,113; and Chang, U.S. Pat. No. 4,543,434. The general reaction system used for these approaches utilizes a small quantity of a radical initiator (acid) that will strip a hydrogen atom from methane, to generate methyl radicals and a small quantity of acid. Some patents have demonstrated that methane can be converted to methyl bisulfate in a single-step using Group VIII noble metal catalyst (such as platinum or palladium), and a strong inorganic acid such as sulfuric acid. Other patents describe processes which do not utilize catalyst in the conversion of methane to methanol (e.g., European Patent No. 1,558,353). Chlorine and other halogen containing acids have also been utilized in a similar manner to convert methane to methanol and other liquids. These processes tend to encounter problems with corrosion at elevated temperatures, produce relatively low yields of methanol, and create unwanted byproduct.

U.S. Pat. No. 7,282,603 to Richards discloses anhydrous processing of methane into methane sulfonic acid, methanol and other compounds and provides an overview of some of the past approaches to converting methane into methanol. The approach of Richards avoids the use or creation of water, and utilizes a radical initiator compound such as halogen gas or Marshall's acid to create methyl radicals.

Existing processes and production facilities for producing liquids from methane are typically subject to various constraints such as mass flow and product yield limitations and plant size and energy consumption requirements.

Accordingly, in view of the art, there is a need for efficient and economical methods and systems for converting carbon dioxide and/or low molecular weight alkanes, in particular methane, into valuable products whereby the emission of carbon dioxide into the environment may be reduced and/or a system and process whereby a light gas stream comprising carbon dioxide and/or methane may be converted into a liquid product. The greenhouse gas problem is addressed by the herein disclosed system and process for the conversion of carbon dioxide to hydrocarbons and/or oxygenates through the use of a high shear reactor. Such systems and methods should permit increased selectivity and yield of liquid oxygenates and conversion of methane and/or carbon dioxide, while allowing economically favorable conditions of operating temperature, pressure and/or reaction time.

SUMMARY

Herein disclosed is a method of producing synthesis gas from carbonaceous material, the method comprising: (a) providing a mixture comprising carbonaceous material and a liquid medium; (b) subjecting the mixture to high shear under gasification conditions whereby a high shear-treated stream comprising synthesis gas is produced; and (c) separating a product comprising synthesis gas from the high shear-treated stream. In an embodiment, (b) subjecting the mixture to high shear to produce a high shear-treated stream comprising synthesis gas comprises contacting the mixture with at least one gas or vapor selected from the group consisting of steam, hydrogen, air, oxygen, and associated gas.

In an embodiment, the method further comprises contacting the mixture with a catalyst that promotes the formation of synthesis gas. In an embodiment, the method further comprises recycling separated unreacted carbonaceous material, separated liquid medium or both from (c) to (a). In an embodiment, the carbonaceous material comprises coke, coal, peat, natural gas, or a combination thereof. In some cases, the coal is selected from the group consisting of bituminous, anthracite, and lignite. In an embodiment, the carbonaceous material comprises powdered coal or coalbed methane.

In an embodiment, the method further comprises utilizing at least a portion of the synthesis gas to produce a liquid product comprising forming a dispersion of synthesis gas in a liquid phase. In an embodiment, utilizing at least a portion of the synthesis gas to produce a liquid product comprises catalytically reacting the at least a portion of the synthesis gas to produce Fischer-Tropsch hydrocarbons. In an embodiment, the liquid product comprises liquid hydrocarbons and alcohols. In an embodiment, the liquid product comprises primarily liquid hydrocarbons, primarily alcohols, or substantially equivalent amounts of alcohols and liquid hydrocarbons. In an embodiment, the liquid phase comprises one or more liquid hydrocarbon produced by Fischer-Tropsch, one or more alcohol, or a combination thereof. In an embodiment, the method of forming a dispersion comprises introducing the synthesis gas and liquid carrier into a high shear device comprising at least one rotor and at least one stator and providing a tip speed of at least about 23 m/sec, wherein the tip speed is defined as $\pi Dn$, where D is the diameter of the at least one rotor and n is the frequency of revolution. In an embodiment, the method further comprises introducing the dispersion into a reactor comprising a fixed bed of catalyst or a fluidized bed of catalyst. In an embodiment, a method of producing liquid product comprising alcohol from synthesis gas comprises introducing synthesis gas obtained via the method disclosed herein and liquid carrier into a high shear device comprising at least one rotor and at least one complementarily-shaped stator; and subjecting the contents of the high shear device to a shear rate of at least 10,000 s$^{-1}$, wherein the shear rate is defined as the tip speed divided by the shear gap, wherein the tip speed is defined as $\pi Dn$, where D is the diameter of the at least one rotor and n is the frequency of revolution.

Herein also disclosed is a method for producing a liquid product. The method comprises forming a dispersion comprising gas bubbles dispersed in a liquid phase in a high shear device, wherein the average gas bubble diameter is less than about 1.5 µm; contacting the dispersion with a multifunctional catalyst to form the liquid product; and recovering the liquid product. In an embodiment, the liquid product is selected from the group consisting of C2+ hydrocarbons, C2+ oxygenates, and combinations thereof. In an embodiment, the gas is selected from the group consisting of carbon dioxide, methane, ethane, propane, butane, pentane, methanol, and combinations thereof. In an embodiment, the gas comprises a hydrogen source or the liquid phase comprises a hydrogen source. In an embodiment, the gas comprises synthesis gas. In some cases, the synthesis gas is generated via natural gas reforming. In some cases, the synthesis gas is generated via solids gasification. In an embodiment, the solid is selected from the group consisting of coal, biomass, and bio-renewables.

In an embodiment, the multifunctional catalyst promotes Fischer-Tropsch reactions. In an embodiment, the multifunctional catalyst promotes dehydrogenation reactions. In an embodiment, the multifunctional catalyst promotes alcohol forming reactions. In an embodiment, the multifunctional catalyst promotes at least two of the following reactions: dehydrogenation, water dissociation, carbon dioxide dissociation, syngas reforming, and alcohol synthesis. In an embodiment, the high shear device comprises a catalytic surface.

Herein described is a system for producing a liquid product, comprising at least one high shear mixing device comprising at least one inlet, at least one outlet, at least one rotor and at least one stator separated by a shear gap, wherein the shear gap is the minimum distance between the at least one rotor and the at least stator, and wherein the high shear mixing device is capable of producing a tip speed of the at least one rotor of greater than 22.9 m/s (4,500 ft/min); and a pump configured for delivering a fluid stream comprising liquid medium via the at least one inlet to the high shear mixing device. In an embodiment, the system further comprises a reactor comprising at least one inlet and at least one outlet, wherein the at least one inlet of the reactor is fluidly connected to the at least one outlet of the high shear mixing device and the at least one outlet of the reactor is configured for extracting the liquid product.

In an embodiment, the reactor is a Fischer-Tropsch reactor, a fixed-bed reactor, or a slurry reactor. In an embodiment, the reactor comprises a multifunctional catalyst. In an embodiment, the multifunctional catalyst promotes both Fischer-Tropsch reactions and alcohol forming reactions or both dehydrogenation reactions and alcohol forming reactions. In an embodiment, the multifunctional catalyst promotes at least two of the following reactions: dehydrogenation, water dissociation, carbon dioxide dissociation, syngas reforming, and alcohol synthesis. In an embodiment, the high shear mixing device of the system comprises a catalytic surface.

Further described herein is a system for producing synthesis gas from carbonaceous material. The system comprises apparatus for providing a mixture comprising carbonaceous material and a liquid medium; at least one high shear device comprising at least one rotor and at least one complementarily-shaped stator and configured to subject the mixture to high shear and produce a high shear-treated stream comprising synthesis gas, wherein the at least one rotor is configured to provide a tip speed of at least about 23 m/sec, wherein the tip speed is defined as πDn, where D is the diameter of the at least one rotor and n is the frequency of revolution; and a pump configured for delivering the mixture to the at least one high shear device. In an embodiment, the system further comprises a vessel coupled to the at least one high shear device, the vessel configured for receiving a high shear-treated stream from the at least one high shear device. In an embodiment, the at least one rotor is separated from the at least one stator by a shear gap in the range of from in the range of from about 0.02 mm to about 5 mm, wherein the shear gap is the minimum distance between the at least one rotor and the at least one stator. In an embodiment, the system further comprises a line for introducing a dispersible gas or vapor into the mixture upstream of the at least one high shear device or into the at least one high shear device. In an embodiment, the system more than one high shear device. In an embodiment, the at least one high shear device comprises at least two generators, wherein each generator comprises a rotor and a complementarily-shaped stator. In an embodiment, the system further comprises apparatus for the production of liquid hydrocarbons, alcohols or a combination thereof wherein the apparatus for producing liquid hydrocarbons, alcohols or a combination thereof is fluidly connected with an outlet of the at least one high shear device.

Embodiments of the present disclosure are directed to a method of reacting one or more components in a liquid medium to form an organic product that may include the steps of feeding a carbonaceous gas and a liquid medium to a high shear device; processing the gas and the liquid medium under shearing conditions in the high shear device, resulting in an emulsion comprising at least some of the carbonaceous gas dispersed in the liquid medium, wherein the dispersed carbonaceous gas comprises gas bubbles with a mean diameter of less than about 1 μm; and reacting the emulsion to produce the organic product. In an embodiment, the carbonaceous gas may include carbon monoxide and the hydrogen-based liquid medium may include methanol.

The method may include feeding hydrogen to the high shear device, and the organic product may comprise ethanol. The method may also include utilizing a catalyst to promote the formation of the organic product. In some embodiments, the catalyst may be a hydrogenation catalyst. In other embodiments, the catalyst may be a carbonylation catalyst.

In some aspects, the high shear device may produces a local pressure of at least about 1034.2 MPa (150,000 psi) at the tip of a first rotor disposed therein. In other aspects, the organic product may include alkanes, olefins, aromatics, or combinations thereof. The high shear device may include a first rotor and a first stator configured with a shear gap therebetween. The shearing conditions may include a localized temperature at a tip of the first rotor of at least 500° C.

Other embodiments of the disclosure pertain to a method of producing a liquid product comprising an organic that may include the steps of introducing gas and liquid carrier into a high shear device comprising at least one rotor and at least one complementarily-shaped stator; and shearing contents of the high shear device at a shear rate of at least 10,000 s$^{-1}$, resulting in an emulsion comprising at least some of the gas dispersed in the liquid carrier, wherein the dispersed gas comprises gas bubbles with a mean diameter of less than about 1 μm; reacting the emulsion to produce the liquid product; and recovering the liquid product.

In some aspects, the liquid product may include C2+ hydrocarbons, C2+ oxygenates, and combinations thereof. In other aspects, the gas may be selected from the group consisting of carbon dioxide, carbon monoxide, methane, ethane, propane, butane, pentane, methanol, and combinations thereof. In an embodiment, the gas comprises a hydrogen source, and the organic may be one of alkanes, olefins, aromatics, or combinations thereof.

Yet other embodiments of the disclosure pertain to a system for producing an organic that may include at least one high shear mixing device comprising a rotor and a stator separated by a shear gap; a pump configured for delivering a fluid stream comprising liquid medium to the high shear mixing device; and a reactor comprising at least one inlet and at least one outlet, wherein the at least one inlet of the reactor is fluidly connected to the high shear mixing device, and the reactor is configured for extracting the organic therefrom.

In some aspects, the reactor may be a Fischer-Tropsch reactor, a fixed-bed reactor, or a slurry reactor. The reactor may include a multifunctional catalyst. In an embodiment, the multifunctional catalyst may promote at least two of the following reactions: dehydrogenation, water dissociation, carbon dioxide dissociation, syngas reforming, and alcohol synthesis.

In other aspects, the high shear mixing device comprises a catalytic surface. In yet other aspects, the rotor may be separated from the stator by a shear gap in the range of from in about 0.02 mm to about 5 mm.

Certain embodiments of an above-described method or system potentially provide for more optimal time, temperature and pressure conditions than are otherwise possible, and which potentially increase the rate of the multiphase process. Certain embodiments of the above-described methods or systems potentially provide overall cost reduction by operating at lower temperature and/or pressure, providing increased product per unit of catalyst consumed, decreased reaction time, and/or reduced capital and/or operating costs.

These and other embodiments and potential advantages will be apparent in the following detailed description and drawings.

BRIEF DESCRIPTION OF THE DRAWINGS

For a more detailed description of the preferred embodiment of the present invention, reference will now be made to the accompanying drawings, wherein.

NOTATION AND NOMENCLATURE

Figure 1:
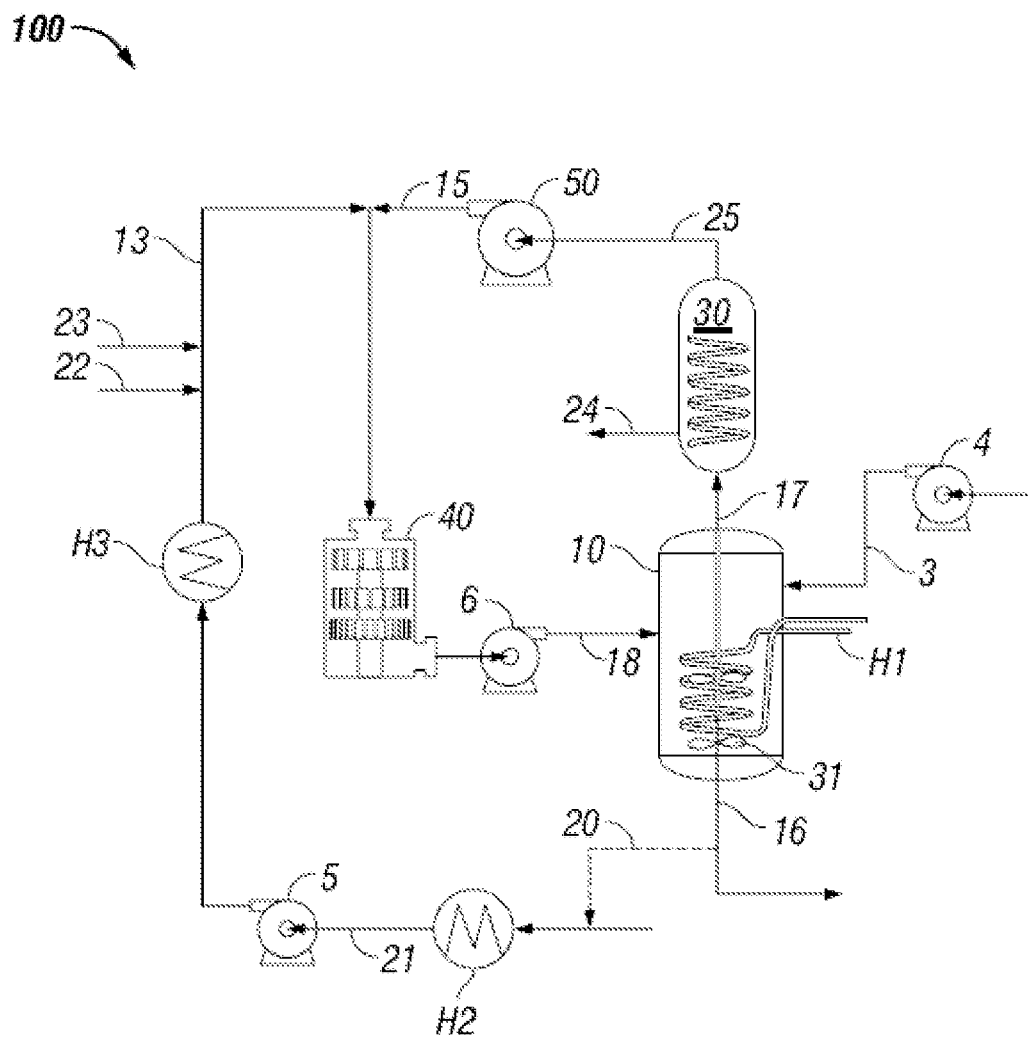
FIG. 1 is a schematic of a multiphase reaction system according to an embodiment of this disclosure comprising external high shear dispersing.

As used herein, the term "dispersion" refers to a liquefied mixture that contains at least two distinguishable substances (or "phases") that will not readily mix and dissolve together. As used herein, a "dispersion" comprises a "continuous" phase (or "matrix"), which holds therein discontinuous droplets, bubbles, and/or particles of the other phase or substance. The term dispersion may thus refer to foams comprising gas bubbles suspended in a liquid continuous phase, emulsions in which droplets of a first liquid are dispersed throughout a continuous phase comprising a second liquid with which the first liquid is immiscible, and continuous liquid phases throughout which solid particles are distributed. As used herein, the term "dispersion" encompasses continuous liquid phases throughout which gas bubbles are distributed, continuous liquid phases throughout which solid particles (e.g., solid catalyst) are distributed, continuous phases of a first liquid throughout which droplets of a second liquid that is substantially insoluble in the continuous phase are distributed, and liquid phases throughout which any one or a combination of solid particles, immiscible liquid droplets, and gas bubbles are distributed. Hence, a dispersion can exist as a homogeneous mixture in some cases (e.g., liquid/liquid phase), or as a heterogeneous mixture (e.g., gas/liquid, solid/liquid, or gas/solid/liquid), depending on the nature of the materials selected for combination. A dispersion may comprise, for example, bubbles of gas (e.g. synthesis gas) and/or particles of carbonaceous material in a liquid phase (e.g. slurry liquid and/or liquid Fischer-Tropsch hydrocarbons).

The term "oxygenate is used herein to refer to substances that have been infused with oxygen. For example, the term refers to any oxygen comprising hydrocarbon such as high octane gasoline or diesel, suitable to drive combustion engines, as well as to oxygenated fuels sometimes employed as gasoline additives to reduce carbon monoxide that is created during the burning of the fuel. The term "oxygenate" includes, but is not limited to, aldehydes such as formaldehyde, methyl formate, and formic acid as well as oxygenates based on alcohols including: methanol, ethanol, isopropyl alcohol, n-propyl alcohol, n-butanol, 2-ethyl hexanol, furfuryl alcohol, benzyl alcohol, isobutyl alcohol, and gasoline grade t-butanol (GTBA). Other oxygenates include carbonyl compounds such as ketones, esters, amides and anhydrides.

The terms "simple alkane" and "low molecular weight alkane" are used herein to refer to low carbon number alkanes including methane, propane, and butane, which are gaseous at room temperature and atmospheric pressure.

The term "light gas" as utilized herein refers to a gas comprising carbon dioxide, simple alkanes having from one to five carbon atoms or a combination thereof.

Use of the phrase, 'all or a portion of' is used herein to mean 'all or a percentage of the whole' or 'all or some components of.'

The term "catalytic surface" is used herein to refer to a surface in a device that is constructed with catalytic material (such as metals, alloys, etc.) so that catalytic activity is manifested when suitable substance comes in touch with said catalytic surface. The use of the term "catalytic surface" in this document includes all such surfaces regardless of the shape and size of surface, material of construct, method of make, degree of activity, or purpose of use.

The term "multifunctional catalyst" is used herein to refer to a catalyst that has more than one function of promoting two or more reactions when necessary reactants are present. For example, such multifunctional catalyst is a blend of two compatible catalysts wherein one catalyst promotes Fischer-Tropsch reactions and the other promotes alcohol forming reactions.

Certain terms are used throughout the following description and claims to refer to particular system components. This document does not intend to distinguish between components that differ in name but not function. In the following discussion and in the claims, the terms "including" and "comprising" are used in an open-ended fashion, and thus should be interpreted to mean "including, but not limited to . . . ".

DETAILED DESCRIPTION

Conversion of Light Gas to Hydrocarbons/Organic Oxygenates.

High shear systems and methods for improving conversion of light gas to hydrocarbons and/or organic oxygenates are disclosed. The system and method may be used to produce Syngas for further processing or hydrocarbons or hydrocarbon mixtures suitable for driving conventional combustion engines or hydrocarbons suitable for further industrial processing or other commercial use. Intermediate products such as methanol or dimethyl ether may also be generated by the process disclosed herein. In an embodiment, the overall process comprises the conversion of gas selected from carbon dioxide, methane, ethane, propane, butane, pentane and combinations thereof to hydrocarbons with carbon numbers greater than 2, preferably $C_5$-$C_{10}$ hydrocarbons and/or oxygenates, such as methanol, acetic acid. In other instances, the method comprises the use of high shear technology for the direct conversion of methane (a major component of available natural gas) to liquid hydrocarbons, primarily organic oxygenates and other liquids. The organic oxygenate product may primarily comprise alcohols. In embodiments, the organic oxygenate product comprises methanol. In embodiments, methanol and carbon dioxide are converted into organic oxygenate product comprising ethanol. In embodiments the process involves production of Syngas from a carbonaceous material followed by conversion to a hydrocarbon liquid.

The present disclosure provides a system and process for the production of hydrocarbons and/or oxygenates from light gas comprising carbon dioxide and/or at least one C1-C5 alkane using at least one high shear reactor device to dissociate reactor feedstock into free radicals by providing intimate contact of reactants and promoting chemical reactions between multiphase reactants. The resulting hydrogen and/or oxygen radicals react with carbon dioxide and/or alkane to yield the product comprising hydrocarbons and/or oxygenates. The high shear device makes favorable reaction(s) that may not be favorable using conventional reactors and operating conditions (i.e. when $\Delta G$ based on global conditions is positive).

In one embodiment, the process comprises providing water and carbon dioxide gas into a high shear reactor. Within the high shear reactor system the water and carbon dioxide may be dissociated into components. Subsequently, the components recombine to produce a product comprising higher carbon number (i.e. $C_{2+}$, preferably $C_5$-$C_{10}$) hydrocarbons and/or oxygenates. The process comprises the use of at least one external high shear device to provide for production of oxygenates and/or hydrocarbons without the need for large volume reactors. In embodiments, the addition of water serves to assist in steam stripping of organics present in vessel 10.

Another aspect of this disclosure is a process for production of hydrocarbons and/or oxygenates from carbon dioxide and/or methane and a source of hydrogen such as simple hydrocarbons or other hydrocarbon source. Water may also optionally or additionally be present as a source of free hydrogen and hydroxyl radicals. In embodiments of the method, the hydrogen source is selected from water, lower alkanes, and combinations thereof. The reaction may be catalyzed with catalytic compounds known to act as dehydrogenation catalyst. In embodiments, the hydrogen source may be a gas, e.g. hydrogen gas, or hydrogen dissociated in HSD 40 from simple gaseous alkane and the liquid in line 21 may be a carrier, such as poly ethylene glycol.

In accordance with certain embodiments, a method is presented for producing product comprising at least one selected from $C_{2+}$ hydrocarbons, oxygenates, and combinations thereof from light gas one or more of carbon dioxide, methane, ethane, propane, butane, pentane, and methanol, the method comprising forming a dispersion of light gas in the liquid feed, wherein the dispersion is formed at least in part with high shear forces, and wherein at least one of the liquid feed and the light gas is a hydrogen source. Forming a dispersion may comprise generating bubbles of light gas having a mean diameter in the range of about 0.1 to about 1.5 micron. In embodiments, the gas bubbles have a mean diameter less than about 0.4 micron.

In some embodiments, the high shear forces are produced with at least one high shear device. The at least one high shear device may comprise at least one generator comprising a stator and a complementary rotor. The rotor and stator may be separated by a minimum clearance in the range of from about 0.02 mm to about 3 mm. In embodiments, forming the dispersion comprises a tip speed of the rotor of greater than 5.0 m/s (1000 ft/min). In embodiments, forming the dispersion comprises a tip speed of the rotor of greater than 20 m/s (4000 ft/min). In embodiments, the at least one high shear device comprises at least two generators. Forming the dispersion may comprise subjecting a mixture of the light gas and the liquid feed to a shear rate of greater than about 20,000 $s^{-1}$. The high shear device may produce a local pressure of at least about 1034.2 MPa (150,000 psi) at the tip of the rotor during formation of the dispersion. The energy expenditure of the high shear device may be greater than 1000 W/m$^3$ during formation of the dispersion.

In some embodiments of the method for producing product comprising at least one selected from $C_{2+}$ hydrocarbons, oxygenates, and combinations thereof from light gas, the dispersion further comprises a catalyst. The catalyst may comprise ruthenium. The catalyst may comprise ruthenium trichloride heptahydrate. The method may further comprise introducing the dispersion into a fixed bed reactor comprising a bed of catalyst. The fixed bed of catalyst may comprise ruthenium carbonyl.

Also disclosed herein is a method for producing product comprising at least one selected from liquid oxygenates, $C_{2+}$ hydrocarbons, and combinations thereof comprising subjecting a fluid mixture comprising a light gas comprising carbon dioxide, methane, or both and a liquid medium to a shear rate greater than 20,000 $s^{-1}$ to produce a dispersion of light gas in a continuous phase of the liquid, wherein the dispersion is formed at least in part with at least one high shear device, the at least one high shear device configured to produce a dispersion of bubbles of the light gas in the liquid medium, and introducing the dispersion into a reactor from which the product comprising at least one selected from liquid oxygenates, $C_{2+}$ hydrocarbons, and combinations thereof is removed. The method may further comprise separating the reactor product into a gas stream and a liquid product stream comprising liquid product, and recycling at least a portion of the gas stream to the external high shear device. In embodiments, the dispersion has an average bubble diameter in the range of about 0.1 to about 1.5 micron. In embodiments, the dispersion has an average bubble diameter of less than 1 micron. The dispersion may be stable for at least about 15 minutes at atmospheric pressure. In embodiments, the high shear device comprises at least two generators. The dispersion may further comprise at least one catalyst.

Also disclosed herein is a system for converting a gas comprising carbon dioxide, methane, ethane, propane, butane, or a combination thereof to product comprising at least one selected from liquid oxygenates, $C_{2+}$ hydrocarbons, and combinations thereof, the system comprising at least one high shear mixing device comprising at least one generator comprising a rotor and a stator separated by a shear gap, wherein the shear gap is the minimum distance between the rotor and the stator, and wherein the high shear mixing device is capable of producing a tip speed of the rotor of greater than 22.9 m/s (4,500 ft/min), and a pump configured for delivering a mixture comprising light gas and a liquid medium to the high shear mixing device. The system may further comprise a reactor disposed between the at least one high shear device and the pump, the reactor comprising a product outlet and an inlet configured to receive the dispersion from the dispersion outlet of the at least one high shear device. The at least one high shear device may comprise at least two generators. The shear rate provided by one generator may be greater than the shear rate provided by another generator. The at least one high shear mixing device may be configured for producing a dispersion of light gas bubbles in a liquid phase comprising liquid medium; wherein the dispersion has a mean bubble diameter of less than 400 nm. The at least one high shear mixing device may be capable of producing a tip speed of the rotor of at least 40.1 m/s (7,900 ft/min). The system may comprise at least two high shear mixing devices.

Some embodiments of the system potentially make possible the production of organic liquid product from gas comprising carbon dioxide, methane, ethane, propane, butane, pentane, methanol or a combination thereof without the need for large volume reactors, via use of an external pressurized high shear reactor.

Overview.

The rate of chemical reactions involving liquids, gases and solids depend on time of contact, temperature, and pressure. In cases where it is desirable to react two or more raw materials of different phases (e.g. solid and liquid; liquid and gas; solid, liquid and gas), one of the limiting factors controlling the rate of reaction involves the contact time of the reactants. In the case of heterogeneously catalyzed reactions there is the additional rate limiting factor of having the reacted products removed from the surface of the catalyst to permit the catalyst to catalyze further reactants. Contact time for the reactants and/or catalyst is often controlled by mixing which provides contact with two or more reactants involved in a chemical reaction.

A reactor assembly that comprises an external high shear device or mixer as described herein makes possible decreased mass transfer limitations and thereby allows the reaction to more closely approach kinetic limitations. When reaction rates are accelerated, residence times may be decreased, thereby increasing obtainable throughput. Product yield may be increased as a result of the high shear system and process. Alternatively, if the product yield of an existing process is acceptable, decreasing the required residence time by incorporation of suitable high shear may allow for the use of lower temperatures and/or pressures than conventional processes.

The present invention utilizes innovative technology to produce organic product comprising hydrocarbons and/or liquid oxygenates from light gas such as carbon dioxide and/or simple alkanes. The light gas is intimately mixed with a liquid medium. At least one of the light gas and the liquid medium serves as hydrogen source. The hydrogen source may be, for example, water and/or hydrocarbons. A high shear reactor device and optionally a catalyst may dissociate reactants into free radicals allowing them to reform into product comprising hydrocarbons and oxygenates.

The system comprises the use of high shear technology for the conversion of carbon dioxide (a major greenhouse gas) and/or simple alkanes to products comprising liquid hydrocarbons, organic oxygenates or combinations thereof. The herein disclosed process and system for the production of hydrocarbons and/or liquid oxygenates via multiphase conversion of carbon dioxide and/or light gas, and a dehydrogenation catalyst employs an external high shear mechanical device to provide rapid contact and mixing of chemical ingredients in a controlled environment in a high shear device. The use of at least one high shear device reduces mass transfer limitations on the reaction(s) thus increasing rates of mass transfer and enabling reactions to more closely approach kinetic limitations and also producing localized non-ideal conditions that permit reactions to occur that would not otherwise be expected to occur based on Gibbs free energy predictions, as discussed further hereinbelow.

System for Production of Liquids from Light Gas.

A high shear system for the production of hydrocarbons and/or liquid oxygenates from light gas will now be described in relation to FIG. 1, which is a process flow diagram of a representative high shear system 100 for the production of organic oxygenates/hydrocarbons via conversion of light gas. The basic components of a representative system include external high shear mixing device (HSD) 40, vessel 10, and pump 5. As shown in FIG. 1, high shear device 40 is located external to vessel/reactor 10. Each of these components is further described in more detail below. Line 21 is connected to pump 5 for introducing liquid medium. Line 13 connects pump 5 to HSD 40, and line 18 connects HSD 40 to vessel 10. One or more line may be connected to line 13 for introducing reactant gas (e.g., carbon dioxide and/or methane gas). For example, in the embodiment in FIG. 1, lines 22 and 23 are connected to line 13. Alternatively, lines 22 and/or 23 may be connected to an inlet of HSD 40. Line 17 may be connected to vessel 10 for removal of unreacted reactant gas and/or reaction product gases. Product outlet line 16 is connected to vessel 10 for removal of liquids from vessel 10. In embodiments, product line 16 may be connected to line 21 or line 13, to provide for multi-pass operation, if desired.

Additional components may be incorporated between vessel 10, external high shear device 40, and pump 5 in some applications of the process, as will become apparent upon reading the description of the high shear process for production of organic product described hereinbelow. For example, high shear system 100 may further comprise condenser 30, compressor 50, feed pump 4, high pressure pump 6, or a combination thereof. As shown in FIG. 1, high shear system 100 may further comprise one or more additional pumps, such as feed pump 4, booster pump 6, or other pumps as necessary. Heat exchangers may be positioned throughout system 100. In embodiments, temperature control equipment is internal to vessel 10, or positioned on a line within system 100. For example, in the embodiment of FIG. 1, heat exchanger H1 is associated with vessel 10, heat exchanger H2 is positioned on line 21, and heat exchanger H3 is positioned on line 13. A heat exchanger may be positioned on line 16 of vessel 10 and may serve to adjust the temperature of reaction products exiting vessel 10.

High Shear Mixing Device.

External high shear mixing device (HSD) 40, also sometimes referred to as a high shear device or high shear mixing device, is configured for receiving an inlet stream, via line 13, comprising liquid medium and dispersible light gas. Alternatively, HSD 40 may be configured for receiving the liquid and gaseous reactant streams via separate inlet lines (not shown). Although only one high shear device is shown in FIG. 1, it should be understood that some embodiments of the system may have two or more high shear mixing devices arranged either in series or parallel flow. HSD 40 is a mechanical device that utilizes one or more generator comprising a rotor/stator combination, each of which has a gap between the stator and rotor. The gap between the rotor and the stator in each generator set may be fixed or may be adjustable. HSD 40 is configured in such a way that it is capable of producing submicron and micron-sized bubbles in a reactant mixture flowing through the high shear device. The high shear device comprises an enclosure or housing so that the pressure and temperature of the reaction mixture may be controlled.

High shear mixing devices are generally divided into three general classes, based upon their ability to mix fluids. Mixing is the process of reducing the size of particles or inhomogeneous species within the fluid. One metric for the degree or thoroughness of mixing is the energy density per unit volume that the mixing device generates to disrupt the fluid particles. The classes are distinguished based on delivered energy densities. Three classes of industrial mixers having sufficient energy density to consistently produce mixtures or emulsions with particle sizes in the range of submicron to 50 microns include homogenization valve systems, colloid mills and high speed mixers. In the first class of high energy devices, referred to as homogenization valve systems, fluid to be processed is pumped under very high pressure through a narrow-gap valve into a lower pressure environment. The pressure gradients across the valve and the resulting turbulence and cavitation act to break-up any particles in the fluid. These valve systems are most commonly used in milk homogenization and can yield average particle sizes in the submicron to about 1 micron range.

At the opposite end of the energy density spectrum is the third class of devices referred to as low energy devices. These systems usually have paddles or fluid rotors that turn at high speed in a reservoir of fluid to be processed, which in many of the more common applications is a food product. These low energy systems are customarily used when average particle sizes of greater than 20 microns are acceptable in the processed fluid.

Between the low energy devices and homogenization valve systems, in terms of the mixing energy density delivered to the fluid, are colloid mills and other high speed rotor-stator devices, which are classified as intermediate energy devices. A typical colloid mill configuration includes a conical or disk rotor that is separated from a complementary, liquid-cooled stator by a closely-controlled rotor-stator gap, which is commonly between 0.0254 mm to 10.16 mm (0.001-0.40 inch). Rotors are usually driven by an electric motor through a direct drive or belt mechanism. As the rotor rotates at high rates, it pumps fluid between the outer surface of the rotor and the inner surface of the stator, and shear forces generated in the gap process the fluid. Many colloid mills with proper adjustment achieve average particle sizes of 0.1-25 microns in the processed fluid. These capabilities render colloid mills appropriate for a variety of applications including colloid and oil/water-based emulsion processing such as that required for cosmetics, mayonnaise, or silicone/silver amalgam formation, to roofing-tar mixing.

Tip speed is the circumferential distance traveled by the tip of the rotor per unit of time. Tip speed is thus a function of the rotor diameter and the rotational frequency. Tip speed (in meters per minute, for example) may be calculated by multiplying the circumferential distance transcribed by the rotor tip, $2\pi R$, where R is the radius of the rotor (meters, for example) times the frequency of revolution (for example revolutions per minute, rpm). A colloid mill, for example, may have a tip speed in excess of 22.9 m/s (4500 ft/min) and may exceed 40 m/s (7900 ft/min). For the purpose of this disclosure, the term 'high shear' refers to mechanical rotor stator devices (e.g., colloid mills or rotor-stator dispersers) that are capable of tip speeds in excess of 5.1 m/s. (1000 ft/min) and require an external mechanically driven power device to drive energy into the stream of products to be reacted. For example, in HSD 40, a tip speed in excess of 22.9 m/s (4500 ft/min) is achievable, and may exceed 40 m/s (7900 ft/min). In some embodiments, HSD 40 is capable of delivering at least 300 L/h at a tip speed of at least 22.9 m/s (4500 ft/min). The power consumption may be about 1.5 kW. HSD 40 combines high tip speed with a very small shear gap to produce significant shear on the material being processed. The amount of shear will be dependent on the viscosity of the fluid. Accordingly, a local region of elevated pressure and temperature is created at the tip of the rotor during operation of the high shear device. In some cases the locally elevated pressure is about 1034.2 MPa (150,000 psi). In some cases the locally elevated temperature is about 500° C. In some cases, these local pressure and temperature elevations may persist for nano or pico seconds.

An approximation of energy input into the fluid (kW/L/min) can be estimated by measuring the motor energy (kW) and fluid output (L/min). As mentioned above, tip speed is the velocity (ft/min or m/s) associated with the end of the one or more revolving elements that is creating the mechanical force applied to the reactants. In embodiments, the energy expenditure of HSD 40 is greater than 1000 W/m$^3$. In embodiments, the energy expenditure of HSD 40 is in the range of from about 3000 W/m$^3$ to about 7500 W/m$^3$.

The shear rate is the tip speed divided by the shear gap width (minimal clearance between the rotor and stator). The shear rate generated in HSD 40 may be in the greater than 20,000 s$^{-1}$. In some embodiments the shear rate is at least 40,000 s$^{-1}$. In some embodiments the shear rate is at least 100,000 s$^{-1}$. In some embodiments the shear rate is at least 500,000 s$^{-1}$. In some embodiments the shear rate is at least 1,000,000 s$^{-1}$. In some embodiments the shear rate is at least 1,600,000 s$^{-1}$. In embodiments, the shear rate generated by HSD 40 is in the range of from 20,000 s$^{-1}$ to 100,000 s$^{-1}$. For example, in one application the rotor tip speed is about 40 m/s (7900 ft/min) and the shear gap width is 0.0254 mm (0.001 inch), producing a shear rate of 1,600,000 s$^{-1}$. In another application the rotor tip speed is about 22.9 m/s (4500 ft/min) and the shear gap width is 0.0254 mm (0.001 inch), producing a shear rate of about 901,600 s$^{-1}$.

HSD 40 is capable of dispersing or transporting light gas into a main liquid phase (continuous phase) with which it would normally be immiscible, at conditions such that at least a portion of the gas is converted to an organic product comprising $C_{2+}$ hydrocarbons, oxygenates, or a combination thereof. The liquid medium may comprise at least one hydrogen source (e.g. simple liquid hydrocarbon or water). In embodiments, the liquid medium further comprises a catalyst. In some embodiments, HSD 40 comprises a colloid mill. Suitable colloidal mills are manufactured by IKA® Works, Inc. Wilmington, N.C. and APV North America, Inc. Wilmington, Mass., for example. In some instances, HSD 40 comprises the DISPAX REACTOR® of IKA® Works, Inc.

The high shear device comprises at least one revolving element that creates the mechanical force applied to the reactants. The high shear device comprises at least one stator and at least one rotor separated by a clearance. For example, the rotors may be conical or disk shaped and may be separated from a complementarily-shaped stator. In embodiments, both the rotor and stator comprise a plurality of circumferentially-spaced teeth. In some embodiments, the stator(s) are adjustable to obtain the desired shear gap between the rotor and the stator of each generator (rotor/stator set). Grooves between the teeth of the rotor and/or stator may alternate direction in alternate stages for increased turbulence. Each generator may be driven by any suitable drive system configured for providing the necessary rotation.

In some embodiments, the minimum clearance (shear gap width) between the stator and the rotor is in the range of from about 0.0254 mm (0.001 inch) to about 3.175 mm (0.125 inch). In certain embodiments, the minimum clearance (shear gap width) between the stator and rotor is about 1.52 mm (0.060 inch). In certain configurations, the minimum clearance (shear gap) between the rotor and stator is at least 1.78 mm (0.07 inch). The shear rate produced by the high shear device may vary with longitudinal position along the flow pathway. In some embodiments, the rotor is set to rotate at a speed commensurate with the diameter of the rotor and the desired tip speed. In some embodiments, the high shear device has a fixed clearance (shear gap width) between the stator and rotor. Alternatively, the high shear device has adjustable clearance (shear gap width).

In some embodiments, HSD 40 comprises a single stage dispersing chamber (i.e., a single rotor/stator combination, a single generator). In some embodiments, high shear device 40 is a multiple stage inline disperser and comprises a plurality of generators. In certain embodiments, HSD 40 comprises at least two generators. In other embodiments, high shear device 40 comprises at least 3 high shear generators. In some embodiments, high shear device 40 is a multistage mixer whereby the shear rate (which, as mentioned above, varies proportionately with tip speed and inversely with rotor/stator gap width) varies with longitudinal position along the flow pathway, as further described hereinbelow.

In some embodiments, each stage of the external high shear device has interchangeable mixing tools, offering flexibility. For example, the DR 2000/4 DISPAX REACTOR® of IKA® Works, Inc. Wilmington, N.C. and APV North America, Inc. Wilmington, Mass., comprises a three stage dispersing module. This module may comprise up to three rotor/stator combinations (generators), with choice of fine, medium, coarse, and super-fine for each stage. This allows for creation of dispersions having a narrow distribution of the desired bubble size (e.g., light gas bubbles). In some embodiments, each of the stages is operated with super-fine generator. In some embodiments, at least one of the generator sets has a rotor/stator minimum clearance (shear gap width) of greater than about 5.0 mm (0.20 inch). In alternative embodiments, at least one of the generator sets has a minimum rotor/stator clearance of greater than about 1.78 mm (0.07 inch).

Figure 2:
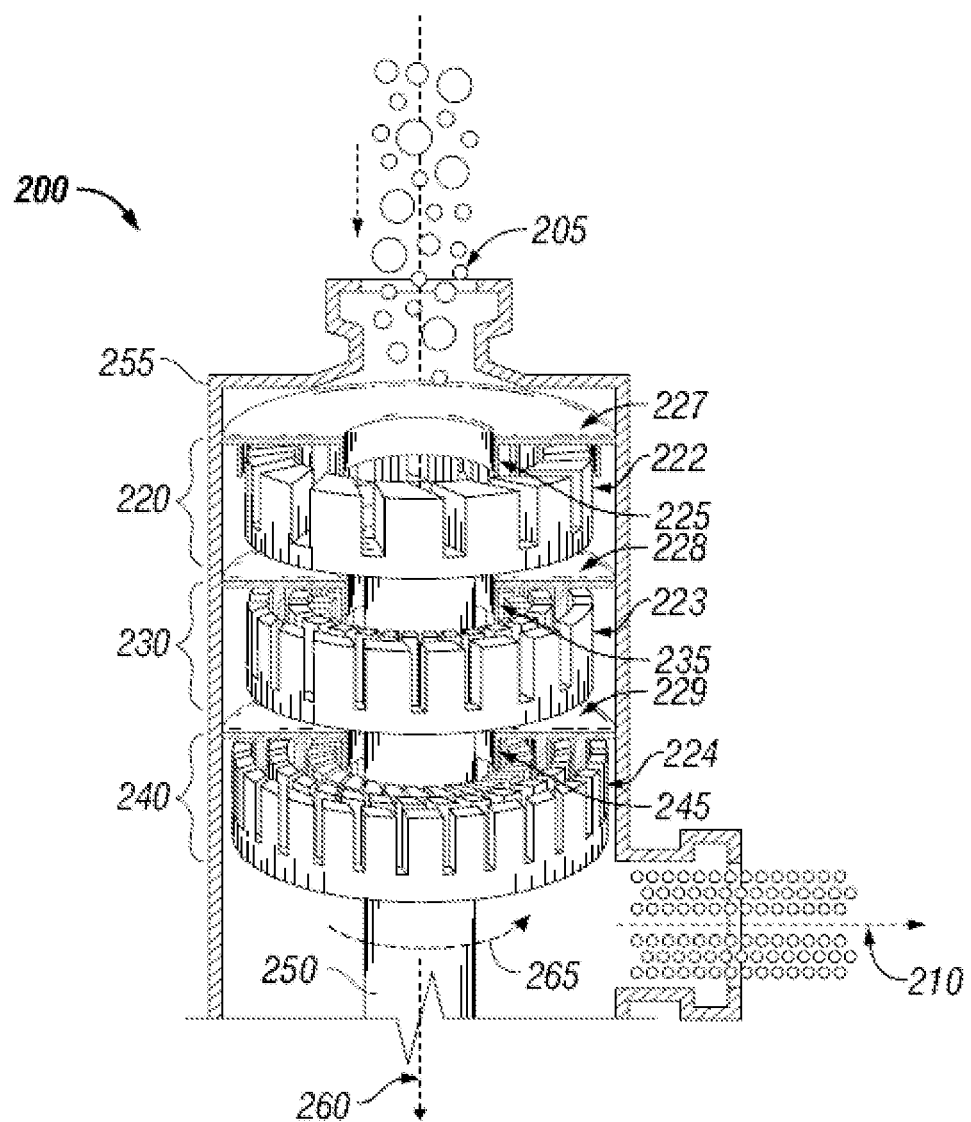
FIG. 2 is a longitudinal cross-section view of a multistage high shear device, as employed in an embodiment of the system.

Referring now to FIG. 2, there is presented a longitudinal cross-section of a suitable high shear device 200. High shear device 200 of FIG. 2 is a dispersing device comprising three stages or rotor-stator combinations. High shear device 200 is a dispersing device comprising three stages or rotor-stator combinations, 220, 230, and 240. The rotor-stator combinations may be known as generators 220, 230, 240 or stages without limitation. Three rotor/stator sets or generators 220, 230, and 240 are aligned in series along drive shaft 250.

First generator 220 comprises rotor 222 and stator 227. Second generator 230 comprises rotor 223, and stator 228. Third generator 240 comprises rotor 224 and stator 229. For each generator the rotor is rotatably driven by input 250 and rotates about axis 260 as indicated by arrow 265. The direction of rotation may be opposite that shown by arrow 265 (e.g., clockwise or counterclockwise about axis of rotation 260). Stators 227, 228, and 229 are fixably coupled to the wall 255 of high shear device 200.

As mentioned hereinabove, each generator has a shear gap width which is the minimum distance between the rotor and the stator. In the embodiment of FIG. 2, first generator 220 comprises a first shear gap 225; second generator 230 comprises a second shear gap 235; and third generator 240 comprises a third shear gap 245. In embodiments, shear gaps 225, 235, 245 have widths in the range of from about 0.025 mm to about 10.0 mm. Alternatively, the process comprises utilization of a high shear device 200 wherein the gaps 225, 235, 245 have a width in the range of from about 0.5 mm to about 2.5 mm. In certain instances the shear gap width is maintained at about 1.5 mm. Alternatively, the width of shear gaps 225, 235, 245 are different for generators 220, 230, 240. In certain instances, the width of shear gap 225 of first generator 220 is greater than the width of shear gap 235 of second generator 230, which is in turn greater than the width of shear gap 245 of third generator 240. As mentioned above, the generators of each stage may be interchangeable, offering flexibility. High shear device 200 may be configured so that the shear rate will increase stepwise longitudinally along the direction of the flow 260.

Generators 220, 230, and 240 may comprise a coarse, medium, fine, and super-fine characterization. Rotors 222, 223, and 224 and stators 227, 228, and 229 may be toothed designs. Each generator may comprise two or more sets of rotor-stator teeth. In embodiments, rotors 222, 223, and 224 comprise more than 10 rotor teeth circumferentially spaced about the circumference of each rotor. In embodiments, stators 227, 228, and 229 comprise more than ten stator teeth circumferentially spaced about the circumference of each stator. In embodiments, the inner diameter of the rotor is about 12 cm. In embodiments, the diameter of the rotor is about 6 cm. In embodiments, the outer diameter of the stator is about 15 cm. In embodiments, the diameter of the stator is about 6.4 cm. In some embodiments the rotors are 60 mm and the stators are 64 mm in diameter, providing a clearance of about 4 mm. In certain embodiments, each of three stages is operated with a super-fine generator, comprising a shear gap of between about 0.025 mm and about 4 mm. For applications in which solid particles are to be sent through high shear device 40, the appropriate shear gap width (minimum clearance between rotor and stator) may be selected for an appropriate reduction in particle size and increase in particle surface area. In embodiments, this may be beneficial for increasing surface area of solid catalyst by shearing and dispersing the particles.

High shear device 200 is configured for receiving from line 13 a reaction mixture at inlet 205. The reaction mixture comprises gas as the dispersible phase and liquid medium as the continuous phase. The feed stream may further comprise a particulate solid catalyst component. Feed stream entering inlet 205 is pumped serially through generators 220, 230, and then 240, such that a dispersion is formed. The dispersion exits high shear device 200 via outlet 210 (and line 18 of FIG. 1). The rotors 222, 223, 224 of each generator rotate at high speed relative to the fixed stators 227, 228, 229, providing a high shear rate. The rotation of the rotors pumps fluid, such as the feed stream entering inlet 205, outwardly through the shear gaps (and, if present, through the spaces between the rotor teeth and the spaces between the stator teeth), creating a localized high shear condition. High shear forces exerted on fluid in shear gaps 225, 235, and 245 (and, when present, in the gaps between the rotor teeth and the stator teeth) through which fluid flows process the fluid and create the dispersion. The product dispersion exits high shear device 200 via high shear outlet 210 (and line 18 of FIG. 1).

The produced dispersion has an average gas bubble size less than about 5 µm. In embodiments, HSD 40 produces a dispersion having a mean bubble size of less than about 1.5 µm. In embodiments, HSD 40 produces a dispersion having a mean bubble size of less than 1 µm; preferably the bubbles are sub-micron in diameter. In certain instances, the average bubble size is from about 0.1 µm to about 1.0 µm. In embodiments, HSD 40 produces a dispersion having a mean bubble size of less than 400 nm. In embodiments, HSD 40 produces a dispersion having a mean bubble size of less than 100 nm. High shear device 200 produces a dispersion comprising dispersed gas bubbles capable of remaining dispersed at atmospheric pressure for at least about 15 minutes.

Not to be limited by theory, it is known in emulsion chemistry that sub-micron particles, or bubbles, dispersed in a liquid undergo movement primarily through Brownian motion effects. The bubbles in the product dispersion created by high shear device 200 may have greater mobility through boundary layers of solid catalyst particles (if present), thereby further facilitating and accelerating the conversion reaction through enhanced transport of reactants in a heterogeneous reaction mixture.

In certain instances, high shear device 200 comprises a DISPAX REACTOR® of IKA® Works, Inc. Wilmington, N.C. and APV North America, Inc. Wilmington, Mass. Several models are available having various inlet/outlet connections, horsepower, tip speeds, output rpm, and flow rate. Selection of the high shear device will depend on throughput requirements and desired particle or bubble size in dispersion in line 18 (FIG. 1) exiting outlet 210 of high shear device 200. IKA® model DR 2000/4, for example, comprises a belt drive, 4M generator, PTFE sealing ring, inlet flange 25.4 mm (1 inch) sanitary clamp, outlet flange 19 mm (¾ inch) sanitary clamp, 2 HP power, output speed of 7900 rpm, flow capacity (water) approximately 300-700 L/h (depending on generator), a tip speed of from 9.4-41 m/s (1850 ft/min to 8070 ft/min).

Vessel.

Once dispersed, the dispersion exits high shear device 40 via high shear device outlet dispersion line 18 and is introduced into vessel 10. Vessel 10 may comprise any type of reactor in which multiphase reaction can be propagated to carry out the conversion reaction(s). For instance, a continuous or semi-continuous stirred tank reactor, or one or more batch reactors may be employed in series or in parallel. In some embodiments, vessel 10 is a tower reactor. In some applications, vessel 10 is a tubular reactor, and in others a tubular reactor or multi-tubular reactor.

Any number of reactor inlet lines is envisioned, with two shown in FIG. 1 (line 3 and line 18). An inlet line may be connected to vessel 10 for receiving a catalyst solution or slurry during operation of the system with heterogeneous catalyst. In embodiments, water is injected into vessel 10 to assist in steam stripping of organics present within vessel 10. In this manner, a portion of the organic product may be stripped with steam and exit vessel 10 in line 17 rather than in line 16. Vessel 10 may comprise an exit line 17 for vent gas, and an outlet product line 16 for a product stream. In embodiments, vessel 10 comprises a plurality of reactor product lines 16.

Conversion of carbon dioxide and/or simple hydrocarbons to organic oxygenates/hydrocarbons will occur wherever suitable time, temperature and pressure conditions exist. In this sense hydrogenation could occur at any point in the flow diagram of FIG. 1 if temperature and pressure conditions are suitable. The reaction carried out by high shear system 100 may comprise a homogeneous catalytic reaction in which the catalyst is in the same phase as another component of the reaction mixture or a heterogeneous catalytic reaction involving a solid catalyst. Where a circulated catalyst is utilized, reaction is more likely to occur at points outside vessel 10 shown of FIG. 1. Nonetheless a discrete reactor/vessel 10 is often desirable to allow for increased residence time, agitation and heating and/or cooling, as well as for separation and recovery of volatile reaction products and recycling of non-reacted gases. Thus, in some embodiments, high shear system 100 further comprises a vessel 10 downstream of the at least one high shear device, wherein an inlet of the vessel is fluidly connected with the dispersion outlet of the high shear device. When a fixed bed reactor 10 is utilized, the reactor/vessel 10 may become the primary location for the reaction to occur.

Vessel 10 outlet line 16 may be fluidly connected to line 21, for example via line 20, for recycle of a portion of the contents in line 16 comprising liquid product to HSD 40. Alternatively, a separate outlet line may connect vessel 10 with line 21 in some embodiments. In FIG. 1, high shear system 100 is configured for recycle of a portion of line 16. This configuration is one which lends itself to multi-pass operation, for example.

Vessel 10 may include one or more of the following components: stirring system, temperature control capabilities, pressure measurement instrumentation, temperature measurement instrumentation, one or more injection points, and level regulator (not shown), as are known in the art of reaction vessel design. As shown in the embodiment of FIG. 1, vessel 10 may further comprise stirring system 31; heating and/or cooling capabilities H1, pressure measurement instrumentation, temperature measurement instrumentation, or a combination thereof. For example, stirring system 31 may include a motor driven mixer. A temperature control apparatus H1 may comprise, for example, a heating mantle or cooling coils. Alternatively, as much of the conversion reaction may occur within HSD 40 in some embodiments, vessel 10 may serve primarily as a storage vessel in some cases. Although generally less desired, in some applications vessel 10 may be omitted, particularly if multiple high shear devices/reactors are employed in series, as further described below.

Heat Transfer Devices.

In addition to the above-mentioned heating/cooling capabilities of vessel 10, other external or internal heat transfer devices for heating or cooling a process stream are also contemplated in variations of the embodiments illustrated in FIG. 1. For example, temperature control may be provided to vessel 10 via internal heat transfer devices as known to one skilled in the art. The use of external heating and/or cooling heat transfer devices is also contemplated. Some suitable locations for one or more such heat transfer devices are between pump 5 and HSD 40, between HSD 40 and vessel 10, and between vessel 10 and pump 5 when system 100 is operated in multi-pass mode. Some non-limiting examples of such heat transfer devices are shell, tube, plate, and coil heat exchangers, as are known in the art.

In the embodiment of high shear system 100 in FIG. 1, three heat transfer devices are used to control temperature throughout the system. Heat transfer device H1 is used to control the temperature of the product in vessel 10. Heat transfer device H2 is positioned on line 21 for controlling temperature in line 21. Heat transfer device H3 serves to control the temperature of line 13 and thereby control the temperature of the inlet feedstream to HSD 40. Use and configuration of heating/cooling devices is for the purpose of carrying out the desired reaction and may be altered accordingly as known to those of skill in the art.

Pump(s)/Cold Trap.

Pump 5 is configured for either continuous or semi-continuous operation, and may be any suitable pumping device that is capable of providing greater than 202.65 kPa (2 atm) pressure, alternatively greater than 303.975 kPa (3 atm) pressure, to allow controlled flow through HSD 40 and system 100. For example, a Roper Type 1 gear pump, Roper Pump Company (Commerce Ga.) Dayton Pressure Booster Pump Model 2P372E, Dayton Electric Co (Niles, Ill.) is one suitable pump. All contact parts of the pump may comprise stainless steel, for example, 316 stainless steel. In some embodiments of the system, pump 5 is capable of pressures greater than about 2026.5 kPa (20 atm). In embodiments, pump 5 produces a flow rate of liquid medium 21 of between about 0.5 and about 1 gallon/min. In embodiments, pump 5 produces a flow rate of liquid medium 21 of about 1 gallon/min.

In addition to pump 5, one or more additional, high pressure pump (not shown) may be included in the system illustrated in FIG. 1. For example, a booster pump, which may be similar to pump 5, may be included between HSD 40 and vessel 10 for boosting the pressure into vessel 10. In the embodiment of FIG. 1, high shear system 100 further comprises a high pressure pump 6 for boosting the pressure into vessel 10. When pump 6 is incorporated as a booster pump, pump 5 may be used as a throttling pump/valve to reduce pressure to the high shear unit, thus reducing wear thereof. As still another example, a compressor type pump may be positioned between line 17 and HSD 40 for recycling gas from vessel 10 to an inlet of the high shear device.

As another example, a supplemental feed pump, which may be similar to pump 5, may be included for introducing additional reactants or catalyst into vessel 10. In the embodiment of FIG. 1, for example, supplemental feed pump 4 is used to introduce additional raw materials into vessel 10 through injection line 3. Catalyst and make-up fluids may be periodically or continuously added as needed to high shear system 100 via feed pump 4 and injection point 3.

As shown in FIG. 1, high shear system 100 may further comprise a cold trap, for example, within condenser 30, positioned on recycle line 17. The cold trap serves to take the recycle gases 17 into an ice cooler receiver from which the gas in line 25 is piped to compressor 50 to be injected into high shear device 40 via line 15. Condenser 28 comprises an outlet line 24 for condensed product (e.g. any oxygenates and/or hydrocarbons) and an outlet line 25 for a recycle gas stream. In embodiments, cold trap of condenser 30 serves to remove primarily alcohols from recycle line 17 upstream of recirculation pump or compressor 50. Recycle line 15 may be fluidly connected to line 13 for reintroduction of light gas to HSD 40, as shown in FIG. 1.

Production of Organic Product by Conversion of Light Gas.

Operation of high shear system 100 will now be discussed with reference to FIG. 1. As shown in the embodiment of high shear system 100 in FIG. 1, in embodiments, system 100 comprises two or more dispersible gas streams. For example, in some embodiments, high shear system 100 comprises dispersible gas line 22 and dispersible gas line 23. In operation for the conversion of light gas to organic product, a dispersible light gas stream is introduced into system 100 via line 22 and/or line 23, and combined in line 13 with a liquid stream. Dispersible gas in line 22 and/or line 23, compressed recycle fluid in line 15 and liquid medium in line 21 are introduced separately or as a mixed stream into external high shear device 40. As shown in FIG. 1, in embodiments, dispersible gas stream in line 22 and/or line 23 is introduced into liquid medium (which may comprise hydrogen source or hydrogen source and catalyst) and the combined gas/liquid (or gas/liquid/solid) stream is introduced into HSD 40.

Dispersible gas introduced into HSD 40 comprises light gas. The light gas to be dispersed in HSD 40 may comprise methane, carbon dioxide, or a combination thereof. As sources of natural gas often comprise additional gaseous components, the light gas introduced into line 13 via line 22, and/or line 23 may further comprise up to about 10% of additional gaseous components. The additional gaseous components may be, for example, ethane, propane, butane, pentane, methanol or a combination thereof. In some embodiments, light gas comprises ethane, propane, butane, or a combination thereof, and light gas in line 23 comprises carbon dioxide. In specific embodiments, light gas comprises methane. In embodiments, dispersible light gas comprises carbon dioxide. In embodiments, light gas comprises carbon dioxide and methane. In embodiments, light gas comprises a 2:1 ratio of methane to carbon dioxide. In embodiments, the light gas comprises carbon dioxide, hydrogen, and carbon monoxide. In embodiments, light gas is continuously fed into line 13. In embodiments, the feed rate of dispersible light gas is greater than about 50 cc/min. Alternatively, the feed rate of dispersible light gas is greater than about 80 cc/min. Alternatively, the feed rate of dispersible light gas is greater than about 2300 cc/min.

The liquid medium may be a variety of types. The liquid medium in line 21 may comprise at least one hydrogen source. The at least one hydrogen source may be selected from water, hydrocarbons, and combinations thereof. In embodiments, liquid medium is selected from water, lower molecular weight liquid alkanes, paraffinic oils and combinations thereof. The paraffinic oil may be either hydroprocessed petroleum derived oil, such as the Paralux oils as supplied by Chevron Products Company or synthetic paraffin oils. Suitable synthetic paraffinic oils include, for example, poly-alpha olefins (API) Group IV base oil as well as hydrocracked/hydroisomerized (API) Group III base oils. Such Group (IV) base oil includes oil such as a low weight component of poly-ethylene-propylene. Petrochemical companies have developed processes involving catalytic conversion of feed stocks under pressure in the presence of hydrogen into high quality Group III mineral lubricating oil. Additionally, GTL (Gas-To-Liquid) synthetic Group III base stocks are available. Liquid medium may further comprise lithium bromide. Liquid medium is desirably selected such that the components thereof do not flash to a considerable degree under conditions within high shear device 40, but remain liquid therein. In some embodiments, liquid medium comprises polyethylene glycol (PEG).

In embodiments, the liquid medium and catalyst are mixed prior to introduction into vessel 10. For example, paraffinic oil and catalyst (if used) may be initially charged into vessel 10 prior to sealing units. In embodiments, catalyst is added to liquid medium in a stirred beaker. In other embodiments, the liquid medium and catalyst are introduced separately and mixed within vessel 10 via reactor agitator 31. Additional reactants may be added to vessel 10 if desired for a particular application, for example via feed pump 4 and vessel 10 inlet line 3. Any number of vessel 10 inlet lines is envisioned. High shear system 100 may then be sealed and vessel 10 evacuated. In embodiments, vessel 10 is purged with oxygen. For example, a vacuum may be pulled via reactor gas line 17.

Following evacuation, dispersible light gas may be injected into high shear system 100 until the pressure in vessel 10 reaches a desired range. In embodiments, dispersible light gas is introduced into high shear device 40 until a pressure of 206.8 kPa (30 psi) is attained in vessel 10. Next, high shear device 40 may be placed in operation, reactor agitation via, for example, stirring system 31 continued, and high shear pumping of reactor fluids throughout high shear system 100 commenced. At this point, the system may be a closed loop with no venting.

In embodiments, the dispersible light gas is fed directly into HSD 40, instead of being combined with the liquid medium in line 13. Pump 5 may be operated to pump the liquid medium through line 21, and to build pressure and feed HSD 40, providing a controlled flow throughout high shear device (HSD) 40 and high shear system 100. In some embodiments, pump 5 increases the pressure of the HSD inlet stream to greater than 202.65 kPa (2 atm), alternatively greater than about 303.975 kPa (3 atmospheres). In this way, high shear system 100 may combine high shear with pressure to enhance reactant intimate mixing.

After pumping, the light gas and liquid medium are mixed within HSD 40, which serves to create a fine dispersion of the light gas in the liquid medium. In HSD 40, the light gas and liquid medium are highly dispersed such that nanobubbles, submicron-sized bubbles, and/or microbubbles of the light gas are formed for superior dissolution into solution and enhancement of reactant mixing. For example, disperser IKA® model DR 2000/4, a high shear, three stage dispersing device configured with three rotors in combination with stators, aligned in series, may be used to create the dispersion of dispersible light gas in liquid medium. The rotor/stator sets may be configured as illustrated in FIG. 2, for example. The combined reactants enter the high shear device via line 13 and enter a first stage rotor/stator combination. The rotors and stators of the first stage may have circumferentially spaced first stage rotor teeth and stator teeth, respectively. The coarse dispersion exiting the first stage enters the second rotor/stator stage. The rotor and stator of the second stage may also comprise circumferentially spaced rotor teeth and stator teeth, respectively. The reduced bubble-size dispersion emerging from the second stage enters the third stage rotor/stator combination, which may comprise a rotor and a stator having rotor teeth and stator teeth, respectively. The dispersion exits the high shear device via line 18. In some embodiments, the shear rate increases stepwise longitudinally along the direction of the flow, 260.

For example, in some embodiments, the shear rate in the first rotor/stator stage is greater than the shear rate in subsequent stage(s). In other embodiments, the shear rate is substantially constant along the direction of the flow, with the shear rate in each stage being substantially the same.

The rotor(s) of HSD 40 may be set to rotate at a speed commensurate with the diameter of the rotor and the desired tip speed. As described above, the high shear device (e.g., colloid mill or toothed rim disperser) has either a fixed clearance between the stator and rotor or has adjustable clearance. In some embodiments of the process, the transport resistance of the reactants is reduced by operation of the high shear device such that the velocity of the reaction is increased by greater than about 5%. In some embodiments of the process, the transport resistance of the reactants is reduced by operation of the high shear device such that the velocity of the reaction is increased by greater than a factor of about 5. In some embodiments, the velocity of the reaction is increased by at least a factor of 10. In some embodiments, the velocity is increased by a factor in the range of about 10 to about 100 fold.

In some embodiments, HSD 40 delivers at least 300 L/h at a tip speed of at least 4500 ft/min, and which may exceed 7900 ft/min (40 m/s). The power consumption may be about 1.5 kW. Although measurement of instantaneous temperature and pressure at the tip of a rotating shear unit or revolving element in HSD 40 is difficult, it is estimated that the localized temperature seen by the intimately mixed reactants is in excess of 500° C. and at pressures in excess of 500 kg/cm$^2$ under cavitation conditions. The high shear mixing results in dispersion of the light gas in micron or submicron-sized bubbles. In some embodiments, the resultant dispersion has an average bubble size less than about 1.5 µm. Accordingly, the dispersion exiting HSD 40 via line 18 comprises micron and/or submicron-sized gas bubbles. In some embodiments, the mean bubble size is in the range of about 0.4 µm to about 1.5 µm. In some embodiments, the resultant dispersion has an average bubble size less than 1 µm. In some embodiments, the mean bubble size is less than about 400 nm, and may be about 100 nm in some cases. In many embodiments, the dispersion is able to remain dispersed at atmospheric pressure for at least 15 minutes. In some embodiments, the average bubble size refers to the average bubble diameter under reaction conditions.

Once dispersed, the resulting gas/liquid or gas/liquid/solid dispersion exits HSD 40 via line 18 and feeds into vessel 10, as illustrated in FIG. 1. Dispersion in line 18 may optionally undergo further processing (heating/cooling) as may be desired in a particular application prior to entering vessel 10. As a result of the intimate mixing of the reactants prior to entering vessel 10, a significant portion of the chemical reaction may take place in HSD 40. Accordingly, in some embodiments, reactor/vessel 10 may be used primarily for heating and separation of product liquids from unreacted light gas and any product gas. Alternatively, or additionally, vessel 10 may serve as a primary reaction vessel where most of the organic product is produced. For example, in embodiments, vessel 10 is a fixed bed reactor comprising a fixed bed of catalyst.

Catalyst.

If a catalyst is used to promote the conversion reactions, the catalyst may be introduced as a slurry or catalyst stream into vessel 10, for example via line 3. Alternatively, or additionally, catalyst may be added elsewhere in system 100. For example, catalyst slurry may be injected into line 21. In some embodiments, system 100 comprises a closed slurry loop, and line 21 may contain liquid medium, liquid product, and/or catalyst recycled from line 16. In embodiments the catalyst may be a fixed bed catalyst.

The system and method of this disclosure pair high shear and possibly cavitation to create conditions not only conducive to generating free hydrogen radicals but also having the potential to generate free hydroxyl radicals and perhaps even deoxygenate carbon dioxide directly.

In some embodiments of the disclosed method, light gas and water are contacted with a catalyst for dissociating water and/or a catalyst for dissociating carbon dioxide and/or alkane. Such catalyst are commonly used in water gas shift reactions The water gas shift (WGS) reaction is a well known catalytic reaction which is used, among other things, to generate hydrogen by chemical reaction of CO with water vapor ($H_2O$) according to the following stoichiometry:

$$CO + H_2O \rightarrow CO_2 + H_2, \qquad (1)$$

wherein the reaction typically utilizes a catalyst. Typical catalysts employed in this reaction are based on combinations of iron oxide with chromium at high temperatures (about 350° C.) or mixtures of copper and zinc materials at lower temperatures (about 200° C.).

Dehydrogenation catalysts also include numerous catalytic composites comprising a platinum group component and a modifier metal component selected from the group consisting of a tin component, germanium component, rhenium component, and mixtures thereof are known. For example related U.S. Pat. Nos. 3,632,503, 3,755,481, and 3,878,131 disclose catalysts comprising a platinum group component, a tin component, and a germanium component on a porous carrier material. Compounds comprising rhenium are also well known for their dehydrogenation properties.

Depending on reaction conditions and catalyst selectivity, simple alcohols such as methanol can be produced directly from light gas and water by the method and system of this disclosure. Oxygen released under the high shear conditions is available to react with other radicals created to produce simple alcohols. From methanol, dimethyl ether may be produced. Dimethyl ether can then be utilized as a fuel either directly or mixed with conventional fuels.

The overall chemistry and the energy balance of the process for light gas comprising carbon dioxide is shown in Formulas 2 through 10. The heat of reactions for formulae 2 through 9 is calculated from the corresponding heats of formation. For a (—$CH_2$—) unit, the heat of formation is calculated as ⅛th of the heat of formation of octane.

$$6H_2O(l) \rightarrow 6H_2(g) + 3O_2(g) \quad 1.710 \text{ kJ Electrical energy} \quad (2)$$

$$H_2O(l) \rightarrow H^+ + OH^- \quad (3)$$

$$2CO_2(g) + 2H_2(g) \rightarrow 2CO(g) + 2H_2O(g) \quad 86.2 \text{ kJ Heat} \quad (4)$$

$$2CO(g) + 4H_2(g) \rightarrow 2CH_3OH(g) \quad -181.6 \text{ kJ Heat} \quad (5)$$

$$2CH_3OH(g) \rightarrow CH_3OCH_3(g) + H_2O(g) \quad -24 \text{ kJ Heat} \quad (6)$$

$$CH_3OCH_3(g) \rightarrow 2(-CH_2-)(g) + H_2O(g) \quad -110 \text{ kJ Heat} \quad (7)$$

$$2CO_2(g) + 2H_2(g) \rightarrow 2O_2(g) + 2(-CH_2-)(l) \quad -229 \text{ kJ Heat balance} \quad (8)$$

$$4H_2O(g) \rightarrow 4H_2O(l) \quad -176 \text{ kJ Heat of condensation} \quad (9)$$

$$2H_2O(l) + 2CO_2(g) \rightarrow 3O_2(g) + 2(-CH_2-)(l) \quad 1305 \text{ kJ Energy balance} \quad (10)$$

Without wishing to be limited by theory, formula 8 shows the balanced equation of all the reactions which are believed to occur after the deoxygenating of $CO_2$ step, i.e., steps 4-7, and the total amount of hydrocarbon generated. Formula 9 shows the heat of condensation for the produced water that may be recycled in the process. The overall chemical balance for steps 2-6 and the calculated overall energy consumption of the process is shown in Formula 10.

Vessel/reactor 10 may be operated in either continuous or semi-continuous flow mode, or it may be operated in batch mode. The contents of vessel 10 may be maintained at a specified reaction temperature using heating and/or cooling capabilities (e.g., heater H1) and temperature measurement instrumentation. Pressure in the vessel may be monitored using suitable pressure measurement instrumentation, and the level of reactants in the vessel may be controlled using a level regulator (not shown), employing techniques that are known to those of skill in the art. The contents may be stirred continuously or semi-continuously with, for example stirring system 31.

In embodiments, at least a portion of the reaction mixture in line 16 comprising liquid medium, liquid product, and optional catalyst is recirculated to HSD 40 for multi-pass operation. Line 16 may be fluidly connected to line 21 by line 20, for recycle of at least a portion of line 16 to HSD 40. As shown in FIG. 1, heat transfer device H2 may serve to control the temperature of line 21.

Unreacted light gas along with any other gas in vessel 10 may exit vessel 10 via gas line 17. As shown in FIG. 1, in embodiments, gas recovered from the vessel 10 headspace may be passed through a condenser 30. Extraction of reactor gas from vessel 10 may be aided by, for example, compressor 50. Condenser 30 may comprise a cooling coil and cold trap. Non-condensed gases from condenser 30 may be introduced via line 25 to a compressor 50. Compressed gas may be recycled via, for example, line 15. Line 15 may introduce compressed material from compressor 50 injected into HSD 40, independently, or into line 13, line 22, and/or line 23. Condensed liquid product 24 exiting condenser 30 is extracted from the system. Condensed liquid in line 24 comprises reaction products that may be utilized by any means known in the art, for example sale thereof or conversion into various other chemical products.

Temperature.

In some embodiments, use of the disclosed process comprising reactant mixing via external high shear device 40 permits conversion of light gas to organic product comprising oxygenates, hydrocarbons, or a combination thereof. The temperature within high shear device 40 is desirably below the flash point of the liquid medium. In embodiments, the reaction temperature is less than 220° C. In some embodiments, operating conditions comprise a temperature in the range of from about 100° C. to about 230° C. In some embodiments, the temperature is in the range of about 30° C. to about 40° C. In some embodiments, the temperature is in the range of from about 160° C. to 180° C. In some specific embodiments, the reaction temperature is in the range of from about 155° C. to about 160° C. In embodiments, the product profile changes with temperature in vessel 10, and the reactor temperature may be adjusted to attain the desired product profile. At increased temperatures, a greater quantity of lower molecular weight materials may be produced, while, at lower temperatures, a greater quantity of higher molecular weight materials may be produced.

Pressure.

In some embodiments, the reaction pressure in vessel 10 is in the range of from about 202.65 kPa (2 atm) to about 5.6 MPa-6.1 MPa (55-60 atm). In some embodiments, reaction pressure is in the range of from about 810.6 kPa to about 1.5 MPa (8 atm to about 15 atm). In embodiments, vessel 10 is operated at or near atmospheric pressure. In embodiments, reaction pressure is less than about 6895 kPa (1000 psi). Alternatively, in some embodiments, the operating pressure is less than about 3445 kPa (500 psi). In some embodiments, the operating pressure is less than about 3100 kPa (450 psi). In some embodiments, the operating pressure is less than about 1030 kPa (150 psi).

In some instances, it is desirable to further enhance the degree of light gas conversion. Increasing reaction pressure increases reaction rate, but also increases wear of the materials constituting the reactors, the piping, and the mechanical parts of the plant, as well as the ancillary devices. The superior dissolution and/or dispersion provided by the external high shear mixing may allow a decrease in operating pressure while maintaining or even increasing product production.

Multiple Pass Operation.

As shown in FIG. 1, it may be desirable to pass the contents of vessel 10, or a fraction thereof, through HSD 40 during a second pass. In this case, line 16 may be connected to line 21 as indicated, such that at least a portion of the contents of line 16 is recycled from vessel 10 and pumped by pump 5 into line 13 and thence into HSD 40. Additional light gas may be injected into line 13, or may be added directly into the high shear device (not shown). In other embodiments, product in line 16 may be further treated (for example, liquid product removed therefrom) prior to recycle of a portion of the liquid in line 16 to high shear device 40.

In some embodiments it may be desirable to pass the liquid medium and dispersible gas comprising carbon dioxide and/or alkane through high shear device 40 and then add optional catalyst into line 13 during a second pass through HSD 40.

Multiple High Shear Mixing Devices.

In some embodiments, two or more high shear devices like HSD 40, or configured differently, are aligned in series, and are used to further enhance the reaction. Their operation may be in either batch or continuous mode. In some instances in which a single pass or "once through" process is desired, the use of multiple high shear devices in series may be advantageous. For example, in embodiments, outlet dispersion in line 18 may be fed into a second high shear device. When multiple high shear devices 40 are operated in series, additional light gas may be injected into the inlet feedstream of each device. Although generally less desirable, in embodiments where multiple high shear devices 40 are operated in series, vessel 10 may be omitted. In some embodiments, multiple high shear devices 40 are operated in parallel, and the outlet dispersions therefrom are introduced into one or more vessel 10.

Product/Downstream Processing.

Gas is removed from vessel 10 via gas outlet line 17. The gas in line 17 may comprise unreacted light gas, $H_2$, as well as oxygenate and/or hydrocarbon product. Gas removed via reactor gas outlet 17 may be further treated and its components recycled. For example, cold trap 30 may be used to condense and remove from gas line 17 any product oxygenate and/or hydrocarbon that escapes vessel 10 in recycle gas line 17. Condensate stream exiting condenser 30 via line 24 may comprise primarily alcohols. In embodiments, the liquid product condensate stream in line 24 comprises methanol. In embodiments, liquid product condensate stream in line 24 comprises greater than 50% methanol. In embodiments, liquid product condensate stream in line 24 comprises greater than 65% methanol. In embodiments, liquid product condensate stream in line 24 comprises about 68% methanol. In embodiments, methanol and carbon dioxide are converted into organic oxygenate product comprising ethanol.

In some applications, the unconverted light gas removed from cold trap 30 via line 25 is recovered and injected (directly or indirectly) back into high shear device 40.

A portion of product in line 16 may be removed from vessel 10. Organic product in line 16 comprises liquid oxygenates, hydrocarbons, or a combination thereof in addition to liquid medium. The product stream may comprise primarily hydrocarbons produced during reaction along with liquid medium. For example, in embodiments, product in line 16 comprises hydrocarbons in polyethylene glycol. In applications where ethane, butane, propane, and pentane are present in the light gas, the resulting product in line 16 may comprise product having a higher carbon number than when methane and carbon dioxide are utilized. In such instances, the product removed via line 16 may comprise greater amounts of mixed oxygenates and aldehydes.

The liquid product comprising oxygenate and/or hydrocarbon recovered from product line 16 and/or condensate line 24 may then be used as a fuel or utilized as a feed stock to another chemical processes, as known to those of skill in the art. For instance, methanol produced by the process may serve as a feed to a process for making formaldehyde.

Enhanced Oil Recovery with Liquids Produced from Methane.

Low API (viscous) oil is often difficult to recover due to poor flow properties. Various techniques are used today to help recover low API oil including $CO_2$, steam and water injection. In drilling for oil, the natural gas from the well is often used to re-pressurize the well in order to enhance oil recovery. Natural gas injection, however, may do little to help recover low API oil that is difficult to move in the well space.

The disclosed system and method may be used in the recovery of petroleum crude oil from oil wells, and may be particularly useful for enhancing recovery of oil (e.g., heavy oil) downhole. Methane gas may be converted to liquids in situ at a well site via the disclosed system and methods and used for enhanced oil recovery.

In an embodiment according to this disclosure, natural gas (comprising methane) either from a well head or otherwise available is converted by the disclosed system and method into liquids that are injected into the well to enhance the recovery of heavier oil deposits therein.

In embodiments, organic oxygenates and other liquid product produced from gas comprising methane and exiting system 100 in line 16 and/or 24 is utilized for enhanced oil recovery. System 100 may be assembled on mobile skid mounted units. Such units may permit gas conversion at remote locations, and excess gas may be flared. Larger units may be used where larger deposits of heavy crude are to be recovered.

Conversion of Light Gas.

In embodiments, greater than about 80% of the light gas is converted into product via the disclosed method, and any remaining unconverted light gas is present in the reactor headspace and/or is dissolved in the liquid product. In some embodiments, greater than about 90% of the light gas is converted into organic product. In some embodiments, substantially all of the light gas is converted to product. In embodiments, substantially all of the light gas is converted into product via multi-pass operation of a closed loop system.

In some embodiments, light gas comprises carbon dioxide, and the conversion of carbon dioxide is greater than about 60%. In embodiments, light gas comprises carbon dioxide and the conversion of carbon dioxide, is greater than about 80%. In embodiments, light gas comprises carbon dioxide and the conversion of carbon dioxide, is greater than about 90%. In embodiments, a closed loop system is used, and substantially all of the carbon dioxide fed in dispersible gas via lines 22 and/or 23 is converted to product.

In embodiments, light gas comprises methane and the conversion of methane, is greater than about 60%. In embodiments, light gas comprises methane and the conversion of methane, is greater than about 80%. In embodiments, light gas comprises methane and the conversion of methane, is greater than about 90%. In embodiments, a closed loop system is used, and substantially all of the methane fed into high shear system 100 is converted to product. In certain embodiments, the yield of organic oxygenates is greater than that of hydrocarbon. In embodiments, the yield of organic oxygenates is greater than about 50%. In some embodiments, the yield of oxygenates is greater than about 70%.

Features.

The increased surface area of the micrometer sized and/or submicrometer sized light gas bubbles in the dispersion in line 18 produced within high shear device 40 results in faster and/or more complete conversion of light gas. As mentioned hereinabove, additional benefits are the ability to operate vessel 10 at lower temperatures and pressures resulting in both operating and capital cost savings. The benefits of the present invention include, but are not limited to, faster cycle times, increased throughput, reduced operating costs and/or reduced capital expense due to the possibility of designing smaller reactors, and/or operating the reactor at lower temperature and/or pressure and the possible reduction in catalyst.

The application of enhanced mixing of the reactants by HSD 40 potentially permits significant production of organic product from light gas. In some embodiments, the enhanced mixing potentiates an increase in throughput of the process stream. In some embodiments, the high shear mixing device is incorporated into an established process, thereby enabling an increase in production (i.e., greater throughput). In contrast to some methods that attempt to increase the degree of conversion by simply increasing reactor pressures, the superior dispersion and contact provided by external high shear mixing may allow in many cases a decrease in overall operating pressure while maintaining or even increasing product production.

Without wishing to be limited to a particular theory, it is believed that the level or degree of high shear mixing is sufficient to increase rates of mass transfer and also produces localized non-ideal conditions that permit reactions to occur that would not otherwise be expected to occur based on Gibbs free energy predictions. Localized non ideal conditions are believed to occur within the high shear device resulting in increased temperatures and pressures with the most significant increase believed to be in localized pressures. The increase in pressures and temperatures within the high shear device are instantaneous and localized and quickly revert back to bulk or average system conditions once exiting the high shear device. In some cases, the high shear mixing device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming). An overview of the application of cavitation phenomenon in chemical/physical processing applications is provided by Gogate et al., "Cavitation: A technology on the horizon," *Current Science* 91 (No. 1): 35-46 (2006). Under such non-ideal conditions, carbon dioxide and/or alkane may be dissociated; and water and/or simple alkane molecules converted into free radicals. The free radicals are then allowed to reform into hydrocarbons and oxygenates. In HSD 40, alkane is dehydrogenated and/or carbon dioxide decoupled potentially with the aid of at least one suitable catalyst to form reactive radical compounds. The disclosed system and method may provide for substantially emissions-free conversion of light gas to valuable product(s) by conversion under non-ideal conditions provided by the use of high shear.

In some embodiments, the system and methods described herein permit design of a smaller and/or less capital intensive process than previously possible without the use of external high shear device 40. Potential advantages of certain embodiments of the disclosed methods are reduced operating costs and increased production from an existing process.

Representative data obtained via an embodiment of the disclosed system and method is presented as Examples 1-5 hereinbelow.

Fischer-Tropsch (FT) Conversion.

Fischer-Tropsch (FT) process is utilized for the conversion of carbonaceous feedstock, e.g., coal or natural gas, to higher value liquid fuel or petrochemicals. Large quantities of methane, the main component of natural gas, are available in many areas of the world. Methane may be reformed with water or partially oxidized with oxygen to produce carbon monoxide and hydrogen (i.e., syngas or synthesis gas). Coal and other solid materials may also be used as starting raw materials from which synthesis gas may be produced. In this disclosure, FT process encompasses syngas reforming (production of hydrocarbons from carbon monoxide and hydrogen); it also encompasses the process of converting natural gas or coal into liquid fuels, e.g., syngas production and syngas reforming.

Preparation of hydrocarbons from synthesis gas is well known in the art and is usually referred to as Fischer-Tropsch synthesis, the Fischer-Tropsch process, or Fischer-Tropsch reaction(s). Catalysts for use in such synthesis usually contain a catalytically active metal of Groups 8, 9, 10 (in the new notation for the periodic table of the elements). In particular, iron, cobalt, nickel, and ruthenium may be used as the catalytically active metal. Cobalt and ruthenium have been found to be especially suitable for catalyzing a process in which synthesis gas is converted to primarily hydrocarbons having five or more carbon atoms (i.e., where the $C_5^+$ selectivity of the catalyst is high). A Fischer-Tropsch catalyst may also be promoted with other metals.

Catalytic hydrogenation of carbon monoxide by Fischer-Tropsch may produce a variety of products ranging from methane to higher alkanes and aliphatic alcohols. Fischer-Tropsch synthesis reactions are very exothermic and reaction vessels must be designed for adequate heat exchange capacity. Because the reactants for Fischer-Tropsch are gases while the product streams include liquids and waxes, the system is typically designed to continuously produce and remove therefrom a desired range of liquid and wax hydrocarbon products.

Research continues on developing more efficient Fischer-Tropsch catalyst systems and reaction systems that increase the selectivity for higher-value hydrocarbons in the Fischer-Tropsch product stream. In particular, a number of studies describe the behavior of iron, cobalt or ruthenium based catalysts in various reactor types, together with the development of catalyst compositions and preparations.

There are significant differences in the molecular weight distributions of the hydrocarbon products from Fischer-Tropsch reaction systems. Product distribution and/or product selectivity depends on the type and structure of the catalysts and on the reactor type and operating conditions. In general, however, the Fischer-Tropsch process yields an abundance of higher molecular weight wax-like compounds. Lower temperature Fischer-Tropsch operation generally produces heavier hydrocarbon products. In conventional Fischer-Tropsch processes, the higher molecular weight materials are subsequently cracked to lower molecular weight liquids for use as fuels and chemical feedstocks. Therefore, it is desirable to maximize the selectivity of the Fischer-Tropsch synthesis to the production of high-value liquid hydrocarbons, for example hydrocarbons with five or more carbon atoms per hydrocarbon chain.

High shear systems and methods for Fischer Tropsch conversion of synthesis gas to liquid and gaseous hydrocarbons are disclosed. In accordance with certain embodiments, a method for forming C2+ hydrocarbons is provided, the method comprising forming a dispersion comprising synthesis gas bubbles dispersed in a liquid phase comprising hydrocarbons in a high shear device, wherein the average bubble diameter of the synthesis gas bubbles is less than about 1.5 μm, introducing the dispersion into a reactor, and removing a product stream comprising liquid hydrocarbons from the reactor. The gas bubbles may have a mean diameter of less than 400 nm. The gas bubbles may have a mean diameter of no more than 100 nm. The synthesis gas may be generated via natural gas reforming. The synthesis gas may be generated via solids gasification. In embodiments, the solid is selected from the group consisting of coal, biomass, and bio-renewables. The reactor may comprise Fischer-Tropsch catalyst and the method may further comprise circulating at least a portion of the product stream to the high shear device. The portion of the product stream circulated to the high shear device may comprise Fischer-Tropsch catalyst. The portion of the product stream circulated to the high shear device may be substantially catalyst-free.

In some embodiments, forming the dispersion comprises subjecting a mixture of the synthesis gas and the liquid phase to a shear rate of greater than about 20,000 $s^{-1}$. The high shear device may comprise at least one rotor, wherein the at least one rotor is rotated at a tip speed of at least 22.9 m/s (4,500 ft/min) during formation of the dispersion. In embodiments, the high shear device produces a local pressure of at least about 1034.2 MPa (150,000 psi) at the tip of the at least one rotor. The energy expenditure of the high shear device may be greater than 1000 W/m$^3$. In embodiments of the method, the catalyst comprises a metal selected from the group consisting of iron, cobalt, and combinations thereof.

Also disclosed herein is a method for converting synthesis gas to C2+ hydrocarbons, the method comprising forming a fluid mixture comprising synthesis gas and a liquid comprising hydrocarbons, subjecting the fluid mixture to a shear rate greater than 20,000 $s^{-1}$ to produce a dispersion of carbon monoxide and hydrogen gas bubbles in a continuous phase of the liquid, and introducing the dispersion into a Fischer-Tropsch reactor from which a reactor product is removed. The method may further comprise removing a gas stream comprising unreacted synthesis gas from a top portion of the reactor, and forming additional dispersion with at least a portion of the unreacted synthesis gas. The average bubble diameter of the hydrogen and carbon monoxide gas bubbles in the dispersion may be less than about 5 µm. In embodiments, the dispersion is stable for at least about 15 minutes at atmospheric pressure. Subjecting the fluid mixture to a shear rate greater than 20,000 $s^{-1}$ may comprise introducing the fluid into a high shear device comprising at least two generators.

A system for converting carbon monoxide gas and hydrogen gas into C2+ hydrocarbons is disclosed herein, the system comprising at least one high shear mixing device comprising at least one rotor and at least one stator separated by a shear gap, wherein the shear gap is the minimum distance between the at least one rotor and the at least stator, and wherein the high shear mixing device is capable of producing a tip speed of the at least one rotor of greater than 22.9 m/s (4,500 ft/min), and a pump configured for delivering a fluid stream comprising liquid medium to the high shear mixing device. The system may further comprise a Fischer Tropsch reactor fluidly connected to an outlet of the external high shear device and having an outlet for a product stream comprising liquid hydrocarbons. The at least one high shear mixing device may be configured for producing a dispersion of hydrogen and carbon monoxide gas bubbles in a liquid phase, wherein the dispersion has a mean bubble diameter of less than 5 nm. In embodiments, the at least one high shear mixing device is capable of producing a tip speed of the at least one rotor of at least 20.3 m/s (4000 ft/min). The system may comprise at least two high shear mixing devices. The reactor may be a slurry reactor. In embodiments, the system further comprises a separator, the product stream further comprises catalyst, and the separator comprises an inlet connected to the outlet for the product stream and an outlet for a catalyst slurry stream from which at least a portion of the liquid hydrocarbons have been removed, and an outlet for a stream comprising liquid hydrocarbons. The method may further comprise a recycle line connecting the outlet for the catalyst slurry stream and an inlet to the Fischer-Tropsch reactor.

In a system for converting synthesis gas to C2+ hydrocarbons, including a Fischer Tropsch reactor and a Fischer-Tropsch catalyst that catalyzes the conversion of synthesis gas to hydrocarbons, an improvement is disclosed, the improvement comprising an external high shear device upstream of the reactor, the external high shear device comprising an inlet for a fluid stream comprising synthesis gas and a liquid medium, and at least one generator comprising a rotor and a stator having a shear gap therebetween, wherein the high shear device provides an energy expenditure of greater than 1000 W/m$^3$ of fluid. The high shear device may comprise at least two generators. In embodiments, the shear rate provided by one generator is greater than the shear rate provided by another generator.

In some embodiments, the system further comprises a pump configured for delivering a liquid medium and synthesis gas to the high shear mixing device. The system comprises a reactor configured for receiving a dispersion from the high shear device. Some embodiments of the system potentially make possible the conversion of synthesis gas into hydrocarbons without the need for large volume Fischer-Tropsch reactors, via the use of an external pressurized high shear reactor.

Overview.

The rate of chemical reactions involving liquids, gases and solids depend on time of contact, temperature, and pressure. In cases where it is desirable to react two or more raw materials of different phases (e.g. solid and liquid; liquid and gas; solid, liquid and gas), one of the limiting factors controlling the rate of reaction involves the contact time of the reactants. In the case of heterogeneously catalyzed reactions there is the additional rate limiting factor of having the reacted products removed from the surface of the catalyst to permit the catalyst to catalyze further reactants. Contact time for the reactants and/or catalyst is often controlled by mixing which provides contact with two or more reactants involved in a chemical reaction.

A reactor assembly that comprises an external high shear device or mixer as described herein makes possible decreased mass transfer limitations and thereby allows the reaction to more closely approach kinetic limitations. When reaction rates are accelerated, residence times may be decreased, thereby increasing obtainable throughput. Product yield may be increased as a result of the high shear system and process. Alternatively, if the product yield of an existing process is acceptable, decreasing the required residence time by incorporation of suitable high shear may allow for the use of lower temperatures and/or pressures than conventional processes. Lower temperature Fischer-Tropsch conversion may be used to desirably produce heavier hydrocarbons.

Furthermore, without wishing to be limited by theory, it is believed that the high shear conditions provided by a reactor assembly that comprises an external high shear device or mixer as described herein may permit Fischer-Tropsch conversion of synthesis gas into liquid hydrocarbons generally having five or more carbon atoms (C5+ hydrocarbons) and gaseous hydrocarbons generally having two or more carbon atoms (C2+ hydrocarbons) at global operating conditions under which reaction may not conventionally be expected to occur to any significant extent.

System for Fischer-Tropsch Conversion of Synthesis Gas to Hydrocarbons.

Figure 3:
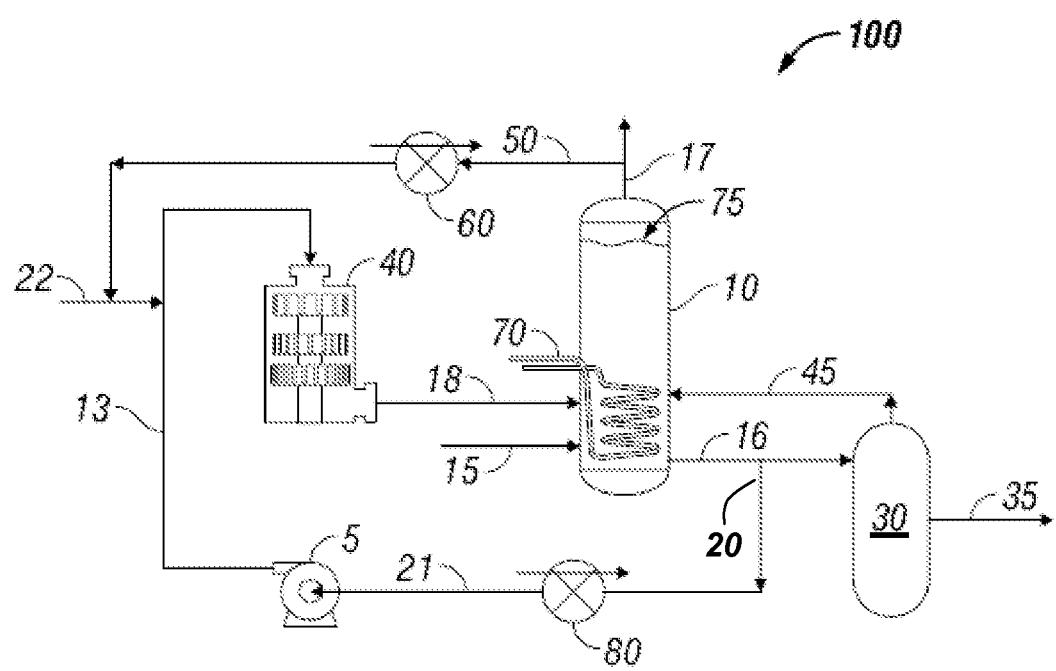
FIG. 3 is a process flow diagram of a high shear Fischer-Tropsch system for conversion of synthesis gas to C2+ hydrocarbons according to an embodiment of this disclosure.

A high shear Fischer-Tropsch conversion system will now be described in relation to FIG. 3, which is a process flow diagram of an embodiment of a high shear system 100 for conversion of synthesis gas into hydrocarbons. The basic components of a representative system include external high shear mixing device (HSD) 40, reactor 10, and pump 5. As shown in FIG. 3, high shear device 40 is located external to reactor 10. Each of these components is further described in more detail below. Line 21 is connected to pump 5 for introducing liquid medium into HSD 40. Line 13 connects pump 5 to HSD 40, and line 18 connects HSD 40 to reactor 10. Line 22 may be connected to line 13 for introducing a gas comprising carbon monoxide and hydrogen (i.e., synthesis gas). Alternatively, line 22 may be connected directly to HSD 40. Line 17 may be connected to reactor 10 for removal of unreacted carbon monoxide, hydrogen and/or other input gas or product gaseous C2+ hydrocarbons. In applications, line 17 may be fluidly connected to line 22 whereby a portion of the gas in line 17 may be recycled to HSD 40. Additional components or process steps may be incorporated between reactor 10 and HSD 40, or ahead of pump 5 or HSD 40, if desired, as will become apparent upon reading the description of the high shear Fischer-Tropsch process described hereinbelow. For example, as indicated in FIG. 3, heat transfer devices such as heat transfer devices 60 and 80 may be positioned throughout system 100 for removing the heat produced during exothermic Fischer-Tropsch conversion. Line 16 may be connected to line 21 or line 13 (e.g., from reactor 10), to provide for multi-pass operation, if desired. As shown in FIG. 3, for example, line 20 may connect line 16 to line 21.

In cases where Fischer-Tropsch catalyst is circulated through HSD 40 (e.g., when reactor 10 is operated as a circulated slurry loop reactor), high shear Fischer-Tropsch system 100 may further comprise separator 30. Separator 30 may be connected to reactor 10 via lines 16 and 45. Product from reactor 10 may be introduced to separator 30 via line 16. Line 45 may connect separator 30 to reactor 10 for return of catalyst slurry to reactor 10.

High shear Fischer-Tropsch system 100 may further comprise downstream processing units for upgrading the liquid and gaseous products from reactor 10 (not shown in FIG. 3).

High Shear Mixing Device.

External high shear mixing device (HSD) 40, also sometimes referred to as a high shear device or high shear mixing device, is configured for receiving an inlet stream, via line 13, comprising liquid medium and synthesis gas. Alternatively, HSD 40 may be configured for receiving the liquid medium and synthesis gas streams via separate inlet lines (not shown). Although only one high shear device is shown in FIG. 3, it should be understood that some embodiments of the system may have two or more high shear mixing devices arranged either in series or parallel flow.

The product dispersion comprising synthesis gas bubbles, and optionally catalyst particles, in a continuous liquid phase may be referred to as an emulsion. The product dispersion has an average gas bubble size less than about 5 µm. In embodiments, HSD 40 produces a dispersion having a mean bubble size of less than about 1.5 µm. In embodiments, HSD 40 produces a dispersion having a mean bubble size of less than 1 µm; preferably the bubbles are sub-micron in diameter. In certain instances, the average bubble size is from about 0.1 µm to about 1.0 µm. In embodiments, HSD 40 produces a dispersion having a mean bubble size of less than 400 nm. In embodiments, HSD 40 produces a dispersion having a mean bubble size of less than 100 nm. High shear device 200 produces a dispersion comprising gas bubbles capable of remaining dispersed at atmospheric pressure for at least about 15 minutes.

Reactor 10.

The Fischer-Tropsch reaction is a heterogeneous catalytic reaction involving a solid catalyst, gaseous carbon monoxide and hydrogen reactants, and liquid product. Reactor 10 may be any type of reactor in which Fischer-Tropsch reaction may be carried out. For instance, a continuous or semi-continuous stirred tank reactor, or one or more batch reactors may be employed in series or in parallel. In embodiments, reactor 10 comprises one or more tank or tubular reactor in series or in parallel. Fischer-Tropsch reactor 10 may be operated as a multitubular fixed bed reactor, a fixed slurry bed reactor, a fixed fluidized bed reactor, or a circulating fluidized bed reactor as known to those of skill in the art.

Any number of reactor inlet lines is envisioned, with three shown in FIG. 3 (lines 15, 18 and 45). Line 18 provides the dispersion of reactant gas comprising carbon monoxide and hydrogen to reactor 10. Line 18 may introduce the dispersion into the bottom half of reactor 10, alternatively, the bottom 25% of reactor 10. Inlet line 15 may be connected to reactor 10 for receiving a catalyst solution or slurry during operation and/or during initiation of the system. When reactor 10 is operated as a circulating slurry reactor, inlet line 45 may be connected with separator 30 for introducing concentrated catalyst slurry from which liquid product has been removed to reactor 10. Reactor 10 may comprise exit line 17 for extracting gas from the top portion of reactor 10. Line 16 is connected to a bottom portion of reactor 10 for removing liquid product from reactor 10. In embodiments where a fixed bed of catalyst is utilized, i.e. where reactor 10 is a multi-tubular fixed bed, a fixed fluidized bed, or a fixed slurry bed, outlet line 16 may comprise no catalyst, and a separator may serve to separate liquid medium from the product hydrocarbons, or separator 30 may be absent in some applications. It is envisaged that reactor 10 may comprise a plurality of reactor product lines 16.

Fischer-Tropsch conversion will occur whenever suitable time, temperature and pressure conditions exist. In this sense synthesis gas conversion could occur at any point in the flow diagram of FIG. 3 if temperature and pressure conditions are suitable. Where a circulating slurry-based catalyst is utilized (i.e., when line 21 contains catalyst particles), reaction is more likely to occur at points outside reactor 10 shown of FIG. 3, than when catalyst is constrained to reactor 10. Nonetheless a discrete reactor 10 is often desirable to allow for increased residence time, agitation and heating and/or cooling.

Reactor 10 may include one or more of the following components: stirring system, temperature control system, pressure measurement instrumentation, temperature measurement instrumentation, one or more injection points, and level regulator (not shown), as are known in the art of reaction vessel design. For example, a stirring system may include a motor driven mixer. A temperature control system may comprise, for example, a heat exchanger 70 with cooling coils or heat transfer tubes. Alternatively, as much of the conversion reaction may occur within HSD 40 in some embodiments, reactor 10 may serve primarily as a storage vessel in some cases. Although generally less desired, in some applications reactor 10 may be omitted, particularly if multiple high shear devices 40 are employed in series, as further described below.

Separator 30.

Separator 30 may be any apparatus suitable for separating a concentrated catalyst slurry from the liquid hydrocarbon products produced in system 100 and any liquid medium charged to the system. Separator 30 may be, for example, selected from hydrocyclones, gravity separators, filters, and magnetic separators. In some embodiments, separator 30 may be a distillation column, whereby liquid hydrocarbons and liquid charge may be separated from Fischer-Tropsch catalyst. In embodiments where gas is removed with liquid hydrocarbon product in line 16, an additional separator may serve to separate gaseous product and unreacted carbon monoxide and hydrogen from liquid hydrocarbon product and liquid medium. Unreacted carbon monoxide and hydrogen may be separated from low-boiling gaseous hydrocarbon and recycled to HSD 40. If the product in line 16 comprises catalyst, the separated liquid hydrocarbon product may then be introduced into separator 30 for removal of a concentrated catalyst stream from the liquid hydrocarbon product.

Heat Transfer Devices.

In addition to the above-mentioned heating/cooling capabilities of reactor 10, other external or internal heat transfer devices for heating or cooling a process stream are also contemplated in variations of the embodiments illustrated in FIG. 3. As Fischer-Tropsch conversion is highly exothermic, heat may be removed from reactor 10 via any method known to one skilled in the art. For example, reactor 10 may comprise one or more internal heat transfer devices 70. The use of external heating and/or cooling heat transfer devices is also contemplated. Some suitable locations for one or more such heat transfer devices are between pump 5 and HSD 40, between HSD 40 and reactor 10, and upstream of pump 5. In the embodiment of FIG. 3, heat transfer device 60 is positioned on gas recycle line 50. In embodiments, heat transfer device 60 is a condenser. The embodiment of FIG. 3 also comprises a heat transfer device 80 positioned on line 21. Heat transfer device 80 may be, for example, a condenser. Some non-limiting examples of such heat transfer devices are condensers, and shell, tube, plate, and coil heat exchangers, as are known in the art.

Pumps.

Pump 5 is configured for either continuous or semi-continuous operation. The capabilities and configuration of pump 5 are described herein above. In addition to pump 5, one or more additional, high pressure pump (not shown) may be included in the system illustrated in FIG. 3. For example, a booster pump, which may be similar to pump 5, may be included between HSD 40 and reactor 10 for boosting the pressure into reactor 10. Such a booster pump may be capable of pressures of from about 500 kPa (72.5 psi) to about 1500 kPa (725 psi), from about 1500 kPa (218 psi) to about 3500 kPa (508 psi), or from about 2000 kPa (290 psi) to about 3000 kPa (435 psi). As another example, a supplemental feed pump, which may be similar to pump 5, may be included for introducing additional reactants or catalyst into reactor 10, for example, via line 15.

Production of Hydrocarbons by Fischer-Tropsch Conversion of Synthesis Gas.

Operation of high shear synthesis gas conversion system 100 will now be discussed with reference to FIG. 3. The system is initially charged with a suitable liquid medium within which the Fischer-Tropsch reactant gases will be dispersed. The initial liquid medium charge may be a variety of types. Suitable hydrocarbon liquids include any aliphatic or aromatic low viscosity organic liquid. Any inert carrier such as silicone oil may also be utilized. Other fluids such as water may also be utilized; however, the resulting dissociation of water may cause co-products of alcohols and aldehydes to be formed. In general the presence of any source of oxygen is undesirable due to the possible oxidation of CO to $CO_2$. Selection of the liquid will be dependent on the desired reaction products from the Fischer-Tropsch process and their solubility in the selected organic liquid. Desirably, the initial charge of liquid medium comprises one or more liquid hydrocarbon product produced by the Fischer-Tropsch reaction such that no separation is needed to separate liquid hydrocarbon products produced in high shear system 100 from the initial charge of liquid medium.

Dispersible gas line 22 comprises synthesis gas to be converted via Fischer Tropsch conversion to C2+ hydrocarbons. The synthesis gas may be prepared or obtained using any method known in the art, including partial oxidation of hydrocarbons, steam reforming, and autothermal reforming. The length of the hydrocarbon chain produced via Fischer-Tropsch conversion is affected by the composition (or ratio of hydrogen to carbon monoxide) of the synthesis gas, the reaction conditions, and the catalyst selectivity. In embodiments, the $H_2$:CO ratio of the dispersible synthesis gas stream introduced via line 22 is from about 1:1 to about 5:1. In embodiments, the $H_2$:CO ratio of the dispersible synthesis gas stream introduced via line 22 is from about 1.7:1 to about 3:1. In embodiments, the $H_2$:CO ratio is about 2. Typically, synthesis gas is produced via gas reformation or gasification of solids, depending on the raw material or feedstock available. In embodiments, carbon monoxide and hydrogen gas in dispersible line 22 is produced via reforming or partial oxidation of natural gas. In embodiments, synthesis gas in line 22 is obtained via gasification of a solid material such as, but not limited to, coal, biomass, and bio-renewables.

In embodiments, the dispersible gas is fed directly into HSD 40, instead of being combined with the liquid reactant stream (i.e., liquid medium) in line 13. Pump 5 may be operated to pump the liquid stream (which will comprise liquid medium and may also comprise product hydrocarbons for multiple cycle operation and which may comprise product hydrocarbons and catalyst, for circulated slurry operation) through line 21, and to build pressure and feed HSD 40, providing a controlled flow throughout HSD 40 and high shear system 100. In some embodiments, pump 5 increases the pressure of the HSD inlet stream to greater than 200 kPa (29 psi), greater than about 300 kPa (43.5 psi), greater than about 500 kPa (72.5 psi), greater than about 1000 kPa (145 psi), or greater than 1500 kPa (218 psi). In this way, high shear system 100 may combine high shear with pressure to enhance reactant intimate mixing.

A heat exchange device may be positioned on line 21 or line 13 for cooling the liquid medium. In the embodiment of FIG. 3, heat exchange device 80 is positioned on line 21.

After pumping, the dispersible gas from line 22 and the liquid from line 13 are mixed within HSD 40, which serves to create a fine dispersion of the carbon monoxide and hydrogen gas in the liquid. In enclosed, external, HSD 40, the synthesis gas and the liquid are highly dispersed such that nanobubbles, submicron bubbles, and/or microbubbles of the gaseous reactants in liquid medium are formed for superior dissolution into solution and enhancement of reactant mixing. For example, disperser IKA® model DR 2000/4, a high shear, three stage dispersing device configured with three rotors in combination with stators, aligned in series, may be used to create the dispersion of dispersible carbon monoxide and hydrogen gas reactants in liquid medium comprising hydrocarbons. The rotor/stator sets may be configured as illustrated in FIG. 2, for example. The dispersed reactants enter the high shear device via line 13 and enter a first stage rotor/stator combination. The rotors and stators of the first stage may have circumferentially spaced first stage rotor teeth and stator teeth, respectively. The coarse dispersion exiting the first stage enters the second rotor/stator stage. The rotor and stator of the second stage may also comprise circumferentially spaced rotor teeth and stator teeth, respectively. The reduced bubble-size dispersion emerging from the second stage enters the third stage rotor/stator combination, which may comprise a rotor and a stator having rotor teeth and stator teeth, respectively. The dispersion exits the high shear device via line 18. The dispersion may further catalyst particles in embodiments in which catalyst is circulated through HSD 40. In some embodiments, the shear rate increases stepwise longitudinally along the direction of the flow, 260.

For example, in some embodiments, the shear rate in the first rotor/stator stage is greater than the shear rate in subsequent stage(s). In other embodiments, the shear rate is substantially constant along the direction of the flow, with the shear rate in each stage being substantially the same.

If the high shear device 40 includes a PTFE seal, the seal may be cooled using any suitable technique that is known in the art. For example, fresh catalyst slurry or optional injected low-boiling hydrocarbon streams (not shown in FIG. 3) may be used to cool the seal and in so doing be preheated as desired prior to entering high shear system 100, for example before entering high shear device 40.

The rotor(s) of HSD 40 may be set to rotate at a speed commensurate with the diameter of the rotor and the desired tip speed. As described above, the high shear device (e.g., colloid mill or toothed rim disperser) has either a fixed clearance between the stator and rotor or has adjustable clearance. HSD 40 serves to intimately mix the synthesis gas and the liquid medium (i.e., fluid stream in line 13 comprising liquid medium, and optionally comprising product hydrocarbons and/or catalyst). In some embodiments of the process, the transport resistance of the reactants is reduced by operation of the high shear device such that the velocity of the reaction is increased by greater than about 5%. In some embodiments of the process, the transport resistance of the reactants is reduced by operation of the high shear device such that the velocity of the reaction is increased by greater than a factor of about 5. In some embodiments, the velocity of the reaction is increased by at least a factor of 10. In some embodiments, the velocity is increased by a factor in the range of about 10 to about 100 fold.

Once dispersed, the resulting gas/liquid or gas/liquid/solid dispersion exits HSD 40 via line 18 and feeds into reactor 10, as illustrated in FIG. 3. Optionally, the dispersion may be further processed (e.g., cooled) prior to entering reactor 10, if desired. In reactor 10, Fischer-Tropsch conversion occurs/continues via contact with Fischer-Tropsch catalyst.

In embodiments, liquid medium, and catalyst are first mixed in reactor 10. Liquid medium and catalyst may enter reactor 10 as a slurry via, for example, inlet line 15. Any number of reactor inlet lines is envisioned, with three shown in FIG. 3 (lines 15, 18 and 45). In an embodiment, reactor 10 is charged with catalyst and the catalyst if required, is activated according to procedures recommended by the catalyst vendor(s), prior to introduction of dispersible gas comprising carbon monoxide and hydrogen into HSD 40.

In embodiments, as shown in FIG. 3, reactor 10 catalyst slurry is circulated through HSD 40. In such embodiments, product in line 16 comprises catalyst, along with liquid product hydrocarbons, and liquid medium (which was used during start-up, for example). In some embodiments, reactor 10 comprises a fixed catalyst bed (e.g., a fixed slurry bed), and catalyst is not removed with liquid product in line 16 and catalyst is not circulated through HSD 40. In fixed catalyst embodiments, wherein catalyst is not circulated through HSD 40, product in line 16 comprises product hydrocarbon and liquid medium. Such product may be sent directly for further processing, or may be recycled, via line 21 for example, to HSD 40 for multi-pass operation.

In the embodiment of FIG. 3, gas stream is removed via line 17 from a gas cap above the level 75 of catalyst suspension or catalyst bed within reactor 10. In other instances, unreacted synthesis gas and product gases (e.g., hydrocarbons with less than 6 carbons) are removed from reactor 10 via line 16 as a mixed stream with liquid hydrocarbon product. In such applications, gaseous and liquid hydrocarbon products may be separated from unreacted carbon monoxide and hydrogen gas in apparatus external to reactor 10. In such embodiments, product removed via line 16 may comprise gaseous hydrocarbon product and unreacted reactant synthesis gas in addition to liquid hydrocarbon product and optionally catalyst. As mentioned above, in such instances, a separator (not shown) may be used to separate unreacted synthesis gas for recycle to HSD 40.

As a result of the intimate mixing of the gaseous reactants prior to entering reactor 10, a significant portion of the chemical reaction may take place in HSD 40, when catalyst is circulated throughout system 100. Accordingly, in some embodiments, reactor 10 may be used primarily for heating/cooling and separation of product hydrocarbons from unreacted reactant and product gases. Alternatively, or additionally, reactor 10 may serve as a primary reaction vessel, especially in cases where catalyst is not circulated throughout system 100 but is associated with reactor 10, where most of the product hydrocarbon is produced. For example, in embodiments, reactor 10 is a fixed bed reactor (e.g., a fixed fluidized bed reactor, a fixed slurry bed reactor, or a multitubular fixed bed reactor) comprising catalyst, and the catalyst is not circulated through HSD 40. In such embodiments, although catalyst may not circulate through HSD 40, catalyst (or slurry) may still be added to or removed from reactor 10 or may be looped about reactor 10. That is, although in some embodiments catalyst is not circulated through HSD 40, catalyst may still be circulated internally within reactor 10 or may be looped, introduced, or removed from reactor 10.

Reactor 10 may be operated in either continuous or semi-continuous flow mode, or it may be operated in batch mode. The contents of reactor 10 may be maintained at a specified reaction temperature using heating and/or cooling capabilities (e.g., cooling coils) and temperature measurement instrumentation. As Fischer-Tropsch is highly exothermic, reactor 10 may comprise an internal heat exchanger 70. Internal heat exchanger 70 may be, for example, one or more cooling coils/heat transfer tubes positioned within reactor 10. Pressure in reactor 10 may be monitored using suitable pressure measurement instrumentation, and the level of catalyst suspension in reactor 10 may be controlled using a level regulator (not shown), employing techniques that are known to those of skill in the art. The contents may be stirred continuously or semi-continuously.

Catalyst.

High shear system 100 comprises a suitable Fischer-Tropsch catalyst, as known in the art. In embodiments, the catalyst is circulated throughout the system, via lines 16, 21, 13, and 18. In other embodiments, a fixed catalyst is utilized, and the catalyst remains within reactor 10. In any event, a suitable Fischer-Tropsch catalyst is utilized. For example, the Fischer-Tropsch catalyst may comprise a supported or unsupported Group 8, 9, or 10 metal. In embodiments, the Group VIII metal is selected form iron, cobalt, ruthenium, nickel, and combinations thereof. The activity of nickel and ruthenium catalysts is conventionally not great enough for commercial use and the price of ruthenium often makes it an unattractive option. Typically, iron is much less costly, while cobalt has the advantage of higher activity and longer life. Because the incorporation of high shear may permit operation at lower temperature and more effective catalyst utilization, the disclosed system and method may make the use of ruthenium and nickel more attractive. The catalyst metal may be supported on an inorganic refractory oxide, such as alumina, silica, silica-alumina, titania, zinc oxide, and Group 4 oxides. The catalyst may further comprise a promoter metal selected from ruthenium, platinum, palladium, rhenium, cerium, halfnium, zirconium, lanthanum, copper and combinations thereof.

Suitable Fischer-Tropsch catalyst may be introduced into reactor 10 via line 15, as a slurry of catalyst in liquid medium or as a catalyst stream. In some embodiments, the catalyst is added continuously to reactor 10 via line 15. In embodiments, reactor 10 comprises a fixed bed of suitable catalyst. In embodiments, catalyst is introduced into reactor 10 and activated according to manufacturer's protocol prior to initiating synthesis gas conversion. Alternatively, or additionally, fresh catalyst may be added elsewhere in high shear Fischer-Tropsch system 100. For example, fresh catalyst slurry may be injected into line 21 or into line 45. Spent catalyst may be removed from system 100 and replaced with fresh catalyst as needed. For example, a portion of catalyst in line 45 may be removed and new catalyst introduced into reactor 10, for example via line 15. Thus, in some embodiments, line 21 comprises hydrocarbon product, liquid medium (which may be hydrocarbon product) and catalyst, and in other embodiments, line 21 carries a fluid stream comprising hydrocarbon product and liquid medium, with no catalyst.

Synthesis gas in dispersible gas line 22 is converted into gaseous and liquid hydrocarbons (e.g., olefins, paraffins, and oxygenated products) via contact with a Fischer-Tropsch catalyst. The Fischer-Tropsch process may be performed either as a high temperature Fischer-Tropsch (HTFT) process, or, perhaps more desirably, a low temperature Fischer-Tropsch (LTFT) process. In embodiments, the Fischer-Tropsch conversion is operated as a LTFT process, and the operating temperature is in the range of from about 180° C. to about 240° C. In embodiments, the Fischer-Tropsch conversion is operated as a HTFT process, and the temperature is in the range of from about 300° C. to 350° C. In embodiments, HTFT is selected, and the catalyst comprises iron. In embodiments, LTFT is selected, and the catalyst comprises iron or cobalt. In embodiments, the temperature of reactor 10 is maintained in the range of from about 180° C. to about 280° C., alternatively, in the range of from 190° C. to 240° C.

In embodiments, the reactor 10 pressure may be from about 500 kPa (72.5 psi) to about 1500 kPa (725 psi). In embodiments, the reactor 10 pressure may be from about 1500 kPa (218 psi) to about 3500 kPa (508 psi). In embodiments, the reactor 10 pressure may be from about 2000 kPa (290 psi) to about 3000 kPa (435 psi). In embodiments, reactor 10 is operated at near atmospheric pressure.

Product hydrocarbons may be produced either continuously, semi-continuously or batch wise, as desired for a particular application. Unreacted gas and product gas may exit reactor 10 via gas line 17. This gas stream may comprise unreacted carbon monoxide and hydrogen, as well as low-boiling product hydrocarbons, vaporized water, and inert gas. The reaction gas removed via line 17 may be further treated, and the components may be recycled, as desired. For example, a portion of the gas in line 17 may be removed as purge. Gaseous C2+ hydrocarbons (generally having less than 6 carbon atoms) may be separated from the purge stream and recycled to high shear system 100 or sent for downstream processing. A portion of the gas in line 17 may be recycled as reactant to HSD 40 via line 50. Heat produced by the exothermic Fischer-Tropsch reaction may desirably be removed from the portion of gas in line 17 recycled to HSD 40. In embodiments, low-boiling product hydrocarbons and vaporized water may be removed from the reactant gas and gaseous hydrocarbons having from one to three carbon atoms (e.g., methane, ethane, propane) by introducing the gas into a condenser 60. The condensed liquids comprising water and low boiling hydrocarbons may thus be separated (and exit high shear system 100) from a gas stream comprising carbon monoxide, hydrogen, and gaseous hydrocarbons having from one to three carbon atoms. The gas stream from condenser 60 may be recycled to reactor 10 via line 22. If gaseous reactants in line 22 have not been pre-cooled, line 22 may be introduced into line 50 such that fresh gaseous reactants are cooled in heat exchanger 60.

Liquid hydrocarbon products of $C5^+$ are extracted from high shear Fischer-Tropsch system 100 via product outlet line 16. Product outlet line 16 may be positioned within the lower 50% of reactor 10, alternatively, within the lower 20% of reactor 10. Fluid may be continuously circulated via line 21 and the Fischer-Tropsch conversion continued over a time period sufficient to produce a desired hydrocarbon product, after which the reaction is terminated as known to those of skill in the art. Catalyst reactivation may be accomplished by means known to those experienced in the art.

In embodiments, product stream in line 16 comprises product hydrocarbons, liquid medium, and catalyst. In embodiments, product in line 16 comprises product hydrocarbons and liquid medium. When a circulating catalyst slurry is utilized, hydrocarbon product stream comprising product hydrocarbons, liquid medium, and catalyst may be introduced into a separator 30 for separation of the product from the catalyst. Separated concentrated catalyst slurry may be recycled to reactor 10 via, for example, line 45. Catalyst-free product may be sent for further processing, for example, via line 35.

In embodiments, at least a portion of reactor discharge in line 16 is introduced to line 21 pump 5 and circulated to HSD 40. In such embodiments, heat exchange device 80 may be used to reduce the temperature in line 21. In embodiments, reactor 10 comprises catalyst slurry and a portion of slurry exits reactor 10 via line 16 and enters pump 5 via pump inlet line 21. Water may be removed from the portion of the reactor discharge in line 16 which is recycled to system 100, as known in the art. Condenser 80 may be used to remove water and reaction heat from fluid in line 21. After pumping, the pressurized slurry is mixed with synthesis gas via dispersible gas line 22 in high shear device 40, which serves to intimately mix the reactants and catalyst. In embodiments, the reactor 10 comprises an uncirculated bed (slurry, fixed, or fluidized) of catalyst, and line 21 comprises liquid catalyst-free hydrocarbon stream from reactor 10 discharge line 16.

The hydrocarbon product produced via the high shear system and process may comprise a mixture of hydrocarbons having a chain length of greater than 5 carbon atoms. The hydrocarbon liquid product may comprise a mixture of hydrocarbons having chain lengths from 5 to about 90 carbon atoms. In embodiments, the majority of the hydrocarbons in the hydrocarbon liquid product have a chain length in the range of from 5 to about 30 carbon atoms. Product upgrading may produce a wide range of commercial products, for example, gasoline, candle wax, and middle distillate fuels including diesel, naphtha, and kerosene.

Single Pass Operation.

In the embodiment shown in FIG. 3, the system is configured for multiple pass operation, wherein a portion of the output from reactor 10 is directed back to HSD 40. In embodiments, single pass operation may be desired. In this case, product in line 16 (for fixed catalyst bed operation) or line 35 (for circulated catalyst operation) may be directed directly to further processing for recovery of desired products. In some embodiments it may be desirable to pass the contents of line 16, or a liquid fraction thereof, through HSD 40 during multiple passes, as described above. In this case, line 16 may be connected to line 21 as indicated by line 20 in FIG. 3, such that at least a portion of the contents of line 16 is recycled from reactor 10 and pumped by pump 5 into line 13 and thence into HSD 40. Additional synthesis gas may be injected via line 22 into line 13, or it may be added directly into the high shear device (not shown).

Multiple High Shear Mixing Devices.

In some embodiments, two or more high shear devices like HSD 40, or configured differently, are aligned in series, and are used to further enhance the reaction. Operation of serial high shear devices 40 may be in either batch or continuous mode. In some instances wherein catalyst is circulated through HSD 40 via line 21, the use of multiple high shear devices in series may permit fewer passes through the system to attain a desired product profile. For example, in embodiments, outlet dispersion 18 may be fed into a second high shear device. When multiple high shear devices 40 are operated in series, additional synthesis gas may be injected into the inlet feedstream of each high shear device. In some embodiments, multiple high shear devices 40 are operated in parallel, and the outlet dispersions therefrom are introduced into one or more reactor 10.

Downstream Processing.

The product liquid hydrocarbons separated from product line 16 or separated and condensed out of gas line 17 may be hydrocracked. The hydrocracking may be catalytic hydrocracking, wherein the liquid hydrocarbon product is contacted with a hydrocracking catalyst. Suitable hydrocracking catalyst may comprise a metal selected from nickel, molybdenum, cobalt, tungsten, or a combination thereof. The catalyst metal may be supported on a support selected from silica, silica-alumina, and zeolites.

The increased surface area of the micrometer sized and/or submicrometer sized synthesis gas bubbles in the dispersion in line 18 produced within high shear device 40 results in faster and/or more complete reaction of hydrogen and carbon monoxide within reactor 10 and, if circulating catalyst operation is chosen, throughout high shear system 100. As mentioned hereinabove, potential benefits are the ability to operate reactor 10 at lower temperatures and pressures resulting in both operating and capital cost savings. Operation of Fischer-Tropsch reactor 10 at lower temperature may increase production of heavier hydrocarbons. The benefits of the present invention may include, but are not limited to, faster cycle times, increased throughput, reduced operating costs and/or reduced capital expense due to the possibility of designing a smaller Fischer-Tropsch reactor 10, operating reactor 10 at lower temperature and/or pressure of Fischer-Tropsch conversion, and/or the possible reduction in the amount of catalyst.

The application of enhanced mixing of the reactants by HSD 40 potentially permits enhanced Fischer-Tropsch conversion of synthesis gas. In some embodiments, the enhanced mixing potentiates an increase in throughput of the process stream. In some embodiments, the high shear mixing device is incorporated into an established process, thereby enabling an increase in production (i.e., greater throughput). Potential advantages of certain embodiments of the disclosed methods are reduced operating costs and increased production from an existing process. Certain embodiments of the disclosed processes additionally offer the advantage of reduced capital costs for the design of new processes. In embodiments, dispersing synthesis gas in liquid medium within high shear device 40 decreases the amount of unreacted synthesis gas in line 17.

Without wishing to be limited to a particular theory, it is believed that the high shear mixing device of certain embodiments of the present system and methods induces cavitation whereby hydrogen and carbon monoxide are dissociated into free radicals, which then react to produce product hydrocarbons.

The present methods and systems for conversion of synthesis gas into C2+ hydrocarbons via Fischer-Tropsch reactions employ an external high shear mechanical device to provide rapid contact and mixing of chemical ingredients in a controlled environment in the reactor/high shear device. The high shear device reduces the mass transfer limitations on the reaction and thus increases the overall reaction rate, and may allow substantial reaction of carbon monoxide and hydrogen under global operating conditions under which substantial reaction may not be expected to occur.

In embodiments, the system and process of the present disclosure provide for a higher selectivity to $C5^+$ hydrocarbons than conventional Fischer-Tropsch processes comprising an absence of external high shear mixing. In embodiments, the degree of mixing in external high shear device 40 is varied to attain a desired outlet product profile. For Fischer-Tropsch conversion, lowering the operating temperature increases the production of heavier hydrocarbons. Because Fischer-Tropsch conversion is highly exothermic, it is often challenging to sufficiently cool Fischer-Tropsch reactor 10 such that longer chain hydrocarbons are produced. A certain amount of energy (i.e., thermal energy) is required to initiate and maintain the Fischer-Tropsch reaction. Typically, the operating temperature will be greater than about 180° C. In embodiments, the high shear Fischer-Tropsch process of the present disclosure allows operation of Fischer-Tropsch reactor 10 at a lower temperature whereby longer hydrocarbons are produced. In embodiments, the use of the present system and method for the Fischer-Tropsch production of C2+ hydrocarbons makes economically feasible the use of ruthenium and/or nickel catalysts on a commercial scale, by increasing contact with catalyst (by decreasing mass transfer resistance).

Gasification of Carbonaceous Materials.

Synthesis gas or 'syngas' is a mixture of hydrogen and carbon monoxide utilized in many industrial processes. For example, synthesis gas may be burned directly in internal combustion engines, used to produce methanol and hydrogen, or converted via the Fischer-Tropsch process into synthetic fuel.

Carbon monoxide, CO, and hydrogen, $H_2$ (i.e. synthesis gas), are the initial reactants used in the Fischer-Tropsch process. The resulting hydrocarbon products are refined to produce the desired synthetic fuel. The utility of the FT process is primarily in its role in producing fluid hydrocarbons from natural gas or solid feedstock. Various feedstocks are utilized including natural gas, lignite, peat, coal or solid carbon-containing wastes of various types. Non-oxidative pyrolysis of the hydrocarbon feedstock may be used to produce syngas which can be used directly as a fuel without being taken through Fischer-Tropsch transformations. If liquid petroleum-like fuel, lubricant, or wax is sought, the Fischer-Tropsch conversion of synthesis gas can be utilized.

Synthesis gas is usually produced by one of two methods. Synthesis gas may be produced by the partial combustion of a hydrocarbon, as indicated in Eq. 1:

$$C_nH_{(2n+2)} + \tfrac{1}{2}nO_2 \rightarrow (n+1)H_2 + nCO. \tag{1}$$

When n=1 (methane), for example, the equation becomes:

$$CH_4 + \tfrac{1}{2}O_2 \rightarrow 2H_2 + CO, \tag{2a}$$

which may also be written as:

$$2CH_4 + O_2 \rightarrow 4H_2 + 2CO. \tag{2b}$$

Synthesis gas may also be produced by the gasification (also called steam reforming) of carbonaceous material, such as coal, biomass, or natural gas:

$$CH_x + H_2O \rightarrow (1+0.5x)H_2 + CO. \tag{3}$$

The value of x depends on the type of fuel. For example, natural gas has a greater hydrogen content (from x=4 to x~2.5) than coal (x<1). The energy needed for the endothermic gasification reaction (3) is usually provided by the (exothermic) combustion of the hydrocarbon source with oxygen.

Gasification is a process that converts carbonaceous materials, such as coal, petroleum, biofuel, and biomass, into hydrogen and carbon monoxide by reacting the raw material at high temperatures with a controlled amount of oxygen and/or steam. The resulting gas mixture is called synthesis gas or syngas and is itself a fuel. Gasification may be used to extract energy from a variety of organic materials.

The advantage of gasification lies in the potential that using the syngas may be more efficient than direct combustion of the original carbonaceous material because it can be combusted at higher temperatures or even in fuel cells. Gasification can also utilize materials that are not otherwise particularly suitable as fuel, for example organic waste or biomass. In addition, the high-temperature combustion refines out corrosive ash elements such as chloride and potassium, providing clean gas from otherwise potentially problematic fuels.

Gasification of fossil fuels is currently widely used on industrial scales to generate electricity. However, almost any type of organic material can be used as the raw material for gasification, such as wood, biomass, or even plastic waste.

Gasification relies on chemical processes at elevated temperatures (generally greater than 700° C.), which distinguishes it from biological processes such as anaerobic digestion that produce biogas.

Gasification may be carried out in a gasifier. In a gasifier, the carbonaceous material undergoes several different processes. The pyrolysis (or devolatilization) process occurs as the carbonaceous particles are heated. Volatiles are released and char is produced. This may result in up to 70% weight loss for coal. The process is, of course, dependent on the properties of the carbonaceous material being processed which determines the structure and composition of the char, which will then undergo gasification reactions.

The combustion process occurs as the volatile products and some of the char react with oxygen to form carbon dioxide and carbon monoxide. The combustion process provides heat for the subsequent gasification reactions. Letting C represent a carbon-containing organic compound, the basic reaction here is:

$$C + \tfrac{1}{2}O_2 \rightarrow CO. \tag{4}$$

The gasification process occurs as the char reacts with carbon dioxide and steam to produce carbon monoxide and hydrogen, via gasification reaction (3), which for x approaching zero becomes:

$$C + H_2O \rightarrow H_2 + CO. \tag{5}$$

In addition, the reversible gas phase water gas shift reaction reaches equilibrium very fast at the temperatures conventionally utilized in a gasifier. This balances the concentrations of carbon monoxide, steam, carbon dioxide and hydrogen, as per the equation:

$$CO + H_2O \leftrightarrow CO_2 + H_2. \tag{6}$$

Essentially, a limited amount of oxygen or air is introduced into the gasifier to allow some of the organic material to be 'burned' to produce carbon monoxide and heat energy, which drives a second reaction that converts further organic material to hydrogen and carbon dioxide.

Gasification of carbonaceous materials tends to produce undesirably high amounts of carbon dioxide, for example greater than 50 mole percent $CO_2$.

Therefore, a carbonaceous feedstock may be used as a source for producing synthesis gas. The produced synthesis gas may have a desired mole ratio of hydrogen to carbon monoxide and/or comprises a desired amount of carbon dioxide. In some embodiments, the system and method may be adjusted depending on the carbonaceous feedstock and/or downstream processes (e.g., FT using a specific FT catalyst) to alter the mole ratio of the product synthesis gas as desired for a given application.

A method of producing synthesis gas from carbonaceous material is described. The method comprises: (a) providing a slurry comprising carbonaceous material and slurry liquid; (b) subjecting the slurry to high shear under gasification conditions whereby a high shear-treated stream comprising synthesis gas is produced; and (c) separating a product comprising synthesis gas from the high shear-treated stream. In embodiments, (c) further comprises separating slurry liquid from the high shear treated stream. In embodiments, (b) subjecting the slurry to high shear to produce a high shear-treated stream comprising synthesis gas further comprises contacting the slurry with at least one gas or vapor selected from steam, hydrogen, air, oxygen, and associated gas. In embodiments, the method further comprises recycling separated unreacted carbonaceous material, separated slurry liquid or both from (c) to (a). In embodiments, (b) subjecting the slurry to high shear to produce a high shear-treated stream comprising synthesis gas comprises subjecting the slurry to a shear rate of at least 20,000 s$^{-1}$. In embodiments, the carbonaceous material comprises coke, coal, peat or a combination thereof. In embodiments, the carbonaceous material comprises coal, peat or a combination thereof. The coal can be selected from bituminous, anthracite, and lignite. In embodiments, (a) providing a slurry further comprises comminuting the carbonaceous material to an average powder size of less than about 75 μm. In embodiments, the slurry liquid is aqueous. In embodiments, the slurry liquid is non-aqueous.

In embodiments, the method further comprises (c) utilizing at least a portion of the produced synthesis gas to produce a different product. In embodiments, (c) utilizing at least a portion of the synthesis gas to produce a different product comprises separating the at least a portion of the synthesis gas from the high shear-treated stream. In embodiments, liquid hydrocarbons are produced during (b) and at least a portion of the liquid hydrocarbons produced in (b) are used in (c). In embodiments, (c) utilizing at least a portion of the synthesis gas to produce a liquid product comprises forming a dispersion of synthesis gas in a liquid phase. In embodiments, (c) utilizing at least a portion of the synthesis gas to produce a different product comprises catalytically reacting the at least a portion of the synthesis gas to produce Fischer-Tropsch hydrocarbons. In embodiments, the liquid product comprises liquid hydrocarbons and alcohols. In embodiments, the liquid product comprises primarily liquid hydrocarbons, primarily alcohols, or substantially equivalent amounts of alcohols and liquid hydrocarbons. In embodiments, the liquid phase comprises one or more liquid hydrocarbon produced by Fischer-Tropsch, one or more alcohol, or a combination thereof. In embodiments, the dispersion comprises synthesis gas bubbles having an average particle diameter of less than or equal to about 5, 4, 3, 2 or 1 μm. In embodiments, the synthesis gas bubbles have an average diameter of less than or equal to about 100 nm.

In embodiments of the method, forming a dispersion comprises subjecting the synthesis gas and liquid carrier to a shear rate of at least about 20,000 $s^{-1}$ in a high shear device comprising at least one rotor and at least one stator, wherein the shear rate is defined as the tip speed divided by the shear gap, and wherein the tip speed is defined as $\pi Dn$, where D is the diameter of the at least one rotor and n is the frequency of revolution. Subjecting the synthesis gas and liquid carrier to a shear rate of at least 20,000 $s^{-1}$ may produce a local pressure of at least about 1034.2 MPa (150,000 psi) at a tip of the at least one rotor. In embodiments, forming a dispersion comprises introducing the synthesis gas and liquid carrier into a high shear device comprising at least one rotor and at least one stator and providing a tip speed of at least about 23 m/sec, wherein the tip speed is defined as $\pi Dn$, where D is the diameter of the at least one rotor and n is the frequency of revolution. The method may further comprise introducing the dispersion into a reactor comprising a fixed bed of catalyst or a fluidized bed of catalyst. The method may further comprise separating unreacted synthesis gas from liquid product. The method may further comprise recycling the unreacted synthesis gas to produce additional dispersion. In embodiments, the slurry comprises powdered coal and coalbed methane.

Also disclosed is a method of producing liquid product comprising alcohol from synthesis gas, the method comprising: introducing synthesis gas and liquid carrier into a high shear device comprising at least one rotor and at least one complementarily-shaped stator; and subjecting the contents of the high shear device to a shear rate of at least 10,000 $s^{-1}$, wherein the shear rate is defined as the tip speed divided by the shear gap, wherein the tip speed is defined as $\pi Dn$, where D is the diameter of the at least one rotor and n is the frequency of revolution. In embodiments, the synthesis gas is obtained via the high shear method of producing synthesis gas from carbonaceous materials described above. In embodiments, (a) the synthesis gas further comprises carbon dioxide; (b) carbon dioxide, $H_2O$, or both is introduced into the high shear device with the synthesis gas and liquid carrier; or both (a) and (b). The liquid product may comprise both liquid hydrocarbons and alcohols. In embodiments, the liquid product comprises liquid hydrocarbons, alcohols and water. In embodiments, the liquid product comprises less than 10% water. In embodiments, the liquid product comprises more liquid hydrocarbons than alcohols or substantially equal amounts of liquid hydrocarbons and alcohols.

The method may further comprise separating the liquid hydrocarbons from the alcohols. The method may further comprise contacting the synthesis gas and liquid carrier with a catalyst. The catalyst may be a Fischer-Tropsch catalyst. In embodiments, the catalyst promotes the production of alcohols. in embodiments, more than 28 moles of liquid produced are produced from 100 moles of gas introduced into the high shear device.

Also disclosed is a system for producing synthesis gas from carbonaceous material, the system comprising: apparatus for providing a slurry comprising carbonaceous material and slurry liquid; at least one high shear device comprising at least one rotor and at least one complementarily-shaped stator and configured to subject the slurry to high shear and produce a high shear-treated stream comprising synthesis gas, wherein the at least one rotor is configured to provide a tip speed of at least about 23 m/sec, wherein the tip speed is defined as $\pi Dn$, where D is the diameter of the at least one rotor and n is the frequency of revolution; and a pump configured for delivering the slurry to the at least one high shear device. In embodiments, the system further comprises a vessel coupled to the at least one high shear device, the vessel configured for receiving a high shear-treated stream from the at least one high shear device. The at least one rotor may be rotatable at a tip speed of at least 40 m/sec. The at least one rotor may be separated from the at least one stator by a shear gap in the range of from in the range of from about 0.02 mm to about 5 mm, wherein the shear gap is the minimum distance between the at least one rotor and the at least one stator. In embodiments, the shear rate provided by rotation of the at least one rotor during operation is at least 20,000 $s^{-1}$, wherein the shear rate is defined as the tip speed divided by the shear gap. In embodiments, the at least one high shear device comprises two or more rotors and two or more stators.

The system may further comprise a line for introducing a dispersible gas or vapor into the slurry upstream of the at least one high shear device or into the at least one high shear device. The dispersible gas or vapor can be selected from air, oxygen, hydrogen, associated gas and steam. In embodiments, the at least one high shear device is configured for producing a dispersion comprising bubbles of synthesis gas, bubbles of dispersible gas or vapor, particles of carbonaceous material, or a combination thereof in a liquid phase comprising slurry liquid, wherein the dispersion has a mean bubble diameter, a mean particle size, or both, of less than about 5, 4, 3, 2, 1, 0.5, 0.4, 0.3, 0.2, or 0.1 μm.

In embodiments, the system comprises more than one high shear device. In embodiments, the at least one high shear device comprises at least two generators, wherein each generator comprises a rotor and a complementarily-shaped stator. The shear rate provided by one generator may be greater than the shear rate provided by another generator.

The system may further comprise apparatus for the production of liquid hydrocarbons, alcohols or a combination thereof wherein the apparatus for producing liquid hydrocarbons, alcohols or a combination thereof is fluidly connected with an outlet of the at least one high shear device.

In embodiments, the apparatus for the production of liquid hydrocarbons, alcohols or a combination thereof comprises at least one high shear device. The at least one high shear device of the apparatus for the production of liquid hydrocarbons, alcohols or a combination thereof may comprise at least one rotor and at least one complementarily-shaped stator. In embodiments, the at least one rotor of the high shear device for the production of liquid hydrocarbons, alcohols or a combination thereof is separated from the at least one stator by a shear gap in the range of from about 0.02 mm to about 5 mm, wherein the shear gap is the minimum distance between the at least one rotor and the at least one stator.

Also disclosed is a system for the production of liquid product comprising hydrocarbons and alcohols from synthesis gas, the system comprising: at least one high shear device comprising at least one rotor and at least one complementarily-shaped stator and configured to subject synthesis gas and liquid carrier to high shear and produce a high shear-treated stream comprising liquid product, wherein the at least one rotor is configured to provide a tip speed of at least about 23 m/sec, wherein the tip speed is defined as πDn, where D is the diameter of the at least one rotor and n is the frequency of revolution; and a pump configured for delivering the liquid carrier to the at least one high shear device via a high shear device inlet line. In embodiments, the at least one high shear device is configured to produce a dispersion comprising bubbles of synthesis gas dispersed in the liquid carrier. The bubbles may have an average bubble diameter of less than 5, 4, 3, 2, or 1 μm. In embodiments, the bubbles have an average bubble diameter in the submicron range. The system may further comprise a catalyst. The system can be configured to produce primarily hydrocarbons, primarily alcohols, or substantially equivalent amounts of liquid hydrocarbons and alcohols.

The system may further comprise a vessel having an inlet fluidly attached to an outlet of the at least one high shear device. In embodiments, the system further comprises a separation device operable to separate alcohols from liquid hydrocarbons, wherein an inlet of the separation device is directly or indirectly connected with an outlet of the at least one high shear device. In embodiments, the system further comprises a line connected to the high shear inlet line for the introduction of synthesis gas into the at least one high shear device. In embodiments, (a) the synthesis gas comprises carbon dioxide in addition to carbon monoxide and hydrogen, (b) the system further comprises a line connected to the high shear inlet line for the introduction of carbon dioxide into the at least one high shear device; or both (a) and (b).

Overview.

Herein disclosed are a system and process for producing synthesis gas. The system comprises an external high shear mechanical device to provide rapid contact and mixing of reactants in a controlled environment in the reactor/mixer device. A reactor assembly that comprises an external high shear device (HSD) or mixer as described herein may decrease mass transfer limitations and thereby allow the reaction, which may be catalytic, to more closely approach kinetic limitations. Enhanced mixing may also homogenize the temperature within the reaction zone(s). Enhancing contact via the use of high shear may permit increased throughput and/or the use of a decreased amount of catalyst (e.g. FT catalyst in certain embodiments) relative to conventional processes and/or may enable reactions to occur that would otherwise not be expected to occur.

High Shear System for Production of Synthesis Gas.

A high shear system 100 for production of synthesis gas will now be described with reference to FIG. 5, which is a process flow diagram of a high shear system 100 according to an embodiment of this disclosure. The basic components of a representative system include external high shear device (HSD) 40 and pump 5. Each of these components is further described in more detail below. Line 21 is connected to pump 5 for introducing feed comprising carbonaceous materials into pump 5. Line 13 connects pump 5 to HSD 40, and line 19 carries a high shear-treated stream out of HSD 40. Synthesis gas production system 100 may further comprise a vessel 10. Vessel 10 may be fluidly connected to HSD 40 via high shear-treated product flow line 19. Vessel 10 may comprise one or more outlet lines. For example, in the embodiments of FIG. 5, vessel 10 comprises first vessel—10 outlet 16, second vessel—10 outlet 17, and third vessel—10 outlet 20.

Additional components or process steps can be incorporated between HSD 40 and vessel 10 or ahead of pump 5 or HSD 40, if desired, as will become apparent upon reading the description of the high shear process hereinbelow. For example, line 20 can be connected to line 21 or line 13 from flow line 19 or reactor 10, such that material (e.g. slurry liquid and/or unreacted carbonaceous material) in flow line 19 or from vessel 10 may be recycled to HSD 40. Product may be removed from system 100 via flow line 19. Flow line 19 is any line into which the high shear-treated stream from HSD 40 (comprising at least liquids and gases and any unreacted solids from HSD 40) flow.

System 100 may further comprise slurry production apparatus 15 for the production of a slurry comprising carbonaceous material, as described further hereinbelow. In embodiments, first dispersible gas line 22 is configured to introduce dispersible gas (or vapor), e.g. hydrogen, oxygen, air, associated gas, steam, into HSD 40. Line 22 may introduce dispersible gas into HSD 40 directly or may introduce dispersible gas into line 13.

The synthesis gas production system may further comprise synthesis gas utilization apparatus 30. For example, in the embodiment of FIG. 5, synthesis gas utilization apparatus 30 comprises a second high shear device 40a and a second pump 5a. Line 21a is connected to pump 5a for introducing liquid carrier into pump 5a. Line 13a connects pump 5a to HSD 40a, and line 19a carries a dispersion out of HSD 40a. Additional components or process steps can be incorporated after HSD 40a, or ahead of pump 5a or HSD 40a, if desired, as will become apparent upon reading the description of the high shear process hereinbelow. Dispersible gas line 22a fluidly connects first outlet line 16 of vessel 10 with second HSD 40a, whereby a portion of the synthesis gas produced in HSD 40 may be used as dispersible gas in HSD 40a. Synthesis gas utilization apparatus 30 may further comprise second vessel 10a. Second vessel 10a may be connected to HSD 40a via dispersion outlet line 19a. Second vessel 10a may comprise one or more outlets, for example first vessel 10a outlet line 16a and second vessel 10a outlet line 17a.

High Shear Device.

External high shear device (HSD) 40 (and second HSD 40a, when present), also sometimes referred to as a high shear mixer, is configured for receiving an inlet stream, via line 13 (13a). Line 22 (22a) may be configured to introduce dispersible gas (or vapor) into HSD 40 (HSD 40a). Alternatively, HSD 40 may be configured for receiving dispersible gas and carbonaceous slurry (or dispersible gas and liquid carrier in the case of HSD 40a) via separate inlet lines.

Figure 5:
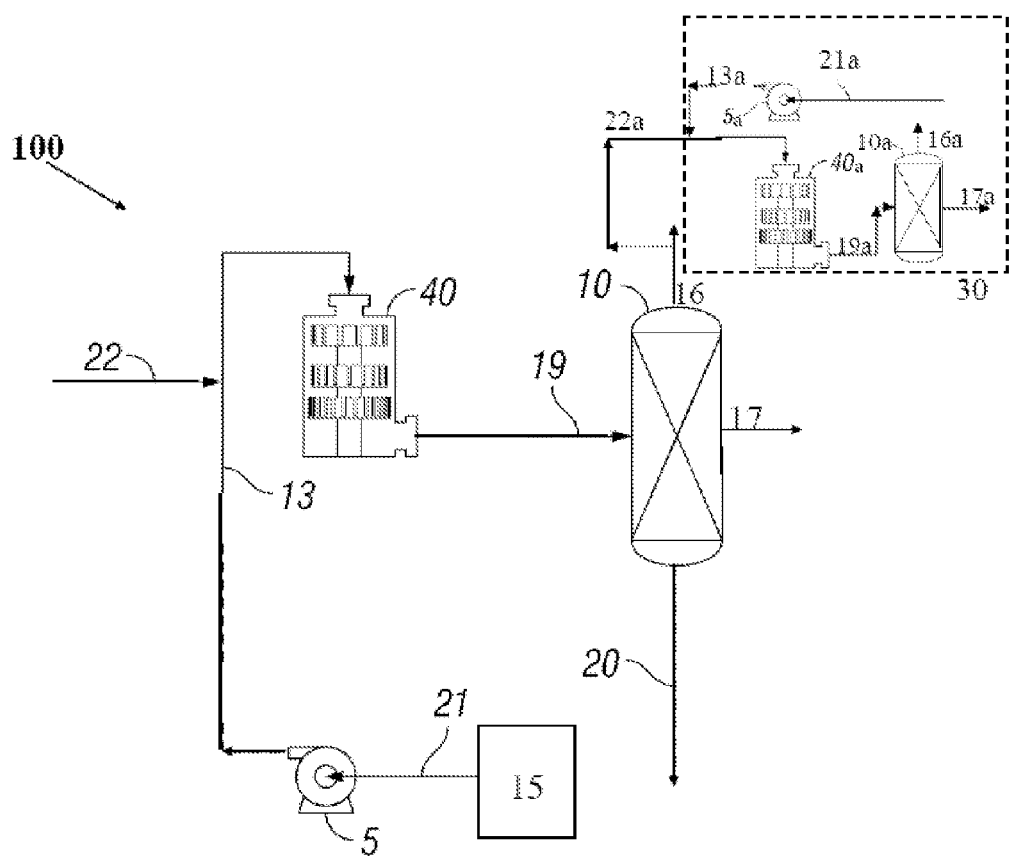
FIG. 5 is a schematic of a high shear system comprising external high shear mixing/dispersing according to an embodiment of this disclosure.

Although only one HSD is shown for producing synthesis gas in the embodiment of FIG. 5 (i.e., prior to synthesis gas utilization apparatus 30), it should be understood that some embodiments of the system can comprise two or more HSDs upstream of synthesis gas utilization apparatus 30. The two or more HSDs can be arranged in either series or parallel flow.

In embodiments, both the rotor and stator comprise a plurality of circumferentially-spaced rings having complementarily-shaped tips. A ring may comprise a solitary surface or tip encircling the rotor or the stator. In embodiments, both the rotor and stator comprise more than 2 circumferentially-spaced rings, more than 3 rings, or more than 4 rings. For example, in embodiments, each of three generators comprises a rotor and stator each having 3 complementary rings, whereby the material processed passes through 9 shear gaps or stages upon traversing HSD 40/40a. Alternatively, each of three generators may comprise four rings, whereby the processed material passes through 12 shear gaps or stages upon passing through HSD 40/40a. In some embodiments, the stator(s) are adjustable to obtain the desired shear gap between the rotor and the stator of each generator (rotor/stator set). Each generator may be driven by any suitable drive system configured for providing the desired rotation.

In some embodiments, HSD 40/40a comprises a single stage dispersing chamber (i.e., a single rotor/stator combination; a single high shear generator). In some embodiments, HSD 40/40a is a multiple stage inline disperser and comprises a plurality of generators. In certain embodiments, HSD 40/40a comprises at least two generators. In other embodiments, HSD 40/40a comprises at least 3 generators. In some embodiments, HSD 40/40a is a multistage mixer whereby the shear rate (which varies proportionately with tip speed and inversely with rotor/stator gap width) varies with longitudinal position along the flow pathway, as further described hereinbelow.

According to this disclosure, at least one surface within HSD 40/40a may be made of, impregnated with, or coated with a catalyst suitable for catalyzing a desired reaction, as described in U.S. patent application Ser. No. 12/476,415 (now U.S. Pat. No. 9,067,859), which is hereby incorporated herein by reference for all purposes not contrary to this disclosure. For example, in embodiments, all or a portion of at least one rotor, at least one stator, or at least one rotor/stator set (i.e., at least one generator) is made of, coated with, or impregnated with a suitable catalyst. In some applications, it may be desirable to utilize two or more different catalysts. In such instances, a generator may comprise a rotor made of, impregnated with, or coated with a first catalyst material, and the corresponding stator of the generator may be made of, coated with, or impregnated by a second catalyst material. Alternatively one or more rings of the rotor may be made from, coated with, or impregnated with a first catalyst, and one or more rings of the rotor may be made from, coated with, or impregnated by a second catalyst. Alternatively one or more rings of the stator may be made from, coated with, or impregnated with a first catalyst, and one or more rings of the stator may be made from, coated with, or impregnated by a second catalyst. All or a portion of a contact surface of a stator, rotor, or both can be made from or coated with catalytic material.

A contact surface of HSD 40/40a can be made from a porous sintered catalyst material, such as platinum. In embodiments, a contact surface is coated with a porous sintered catalytic material. In applications, a contact surface of HSD 40/40a is coated with or made from a sintered material and subsequently impregnated with a desired catalyst. The sintered material can be a ceramic or can be made from metal powder, such as, for example, stainless steel or pseudoboehmite. The pores of the sintered material may be in the micron or the submicron range. The pore size can be selected such that the desired flow and catalytic effect are obtained. Smaller pore size may permit improved contact between fluid comprising reactants and catalyst. By altering the pore size of the porous material (ceramic or sintered metal), the available surface area of the catalyst can be adjusted to a desired value. The sintered material may comprise, for example, from about 70% by volume to about 99% by volume of the sintered material or from about 80% by volume to about 90% by volume of the sintered material, with the balance of the volume occupied by the pores.

In embodiments, the rings defined by the tips of the rotor/stator contain no openings (i.e. teeth or grooves) such that substantially all of the reactants are forced through the pores of the sintered material, rather than being able to bypass the catalyst by passing through any openings or grooves which are generally present in conventional dispersers. In this manner, for example, a reactant will be forced through the sintered material, thus forcing contact with the catalyst.

In embodiments, the sintered material of which the contact surface is made comprises stainless steel or bronze. The sintered material (sintered metal or ceramic) may be passivated. A catalyst may then be applied thereto. The catalyst may be applied by any means known in the art. The contact surface may then be calcined to yield the metal oxide (e.g. stainless steel). The first metal oxide (e.g., the stainless steel oxide) may be coated with a second metal and calcined again. For example, stainless steel oxide may be coated with aluminum and calcined to produce aluminum oxide. Subsequent treatment may provide another material. For example, the aluminum oxide may be coated with silicon and calcined to provide silica. Several calcining/coating steps may be utilized to provide the desired contact surface and catalyst(s). In this manner, the sintered material which either makes up the contact surface or coats the contact surface may be impregnated with a variety of catalysts. Another coating technique, for example, is metal vapor deposition or chemical vapor deposition, such as typically used for coating silicon wafers with metal.

In embodiments, a sintered metal contact surface (e.g., of the rotor or the stator) is treated with a material. For example, tetra ethyl ortho silicate (TEOS). Following vacuum evaporation, TEOS may remain in surface pores. Calcination may be used to convert the TEOS to silica. This impregnation may be repeated for all desired metal catalysts. Upon formation, coating, or impregnation, the catalyst(s) may be activated according to manufacturer's protocol. For example, catalysts may be activated by contacting with an activation gas, such as hydrogen. The base material may be silicon or aluminum which, upon calcination, is converted to alumina or silica respectively. Suitable catalysts, including without limitation, rhenium, palladium, rhodium, etc. can subsequently be impregnated into the pores. The catalyst may be a catalyst effective for catalyzing FT reactions, as discussed further hereinbelow.

In some embodiments, the minimum clearance (shear gap width) between the stator and the rotor is in the range of from about 0.025 mm (0.001 inch) to about 3 mm (0.125 inch). In some embodiments, the minimum clearance (shear gap width) between the stator and the rotor is in the range of from about 1 μm (0.00004 inch) to about 3 mm (0.012 inch). In some embodiments, the minimum clearance (shear gap width) between the stator and the rotor is less than about 10 µm (0.0004 inch), less than about 50 µm (0.002 inch), less than about 100 µm (0.004 inch), less than about 200 µm (0.008 inch), less than about 400 µm (0.016 inch). In certain embodiments, the minimum clearance (shear gap width) between the stator and rotor is about 1.5 mm (0.06 inch). In certain embodiments, the minimum clearance (shear gap width) between the stator and rotor is about 0.2 mm (0.008 inch). In certain configurations, the minimum clearance (shear gap) between the rotor and stator is at least 1.7 mm (0.07 inch). The shear rate produced by the HSD may vary with longitudinal position along the flow pathway. In some embodiments, the rotor is set to rotate at a speed commensurate with the diameter of the rotor and the desired tip speed. In some embodiments, the HSD has a fixed clearance (shear gap width) between the stator and rotor. Alternatively, the HSD has adjustable clearance (shear gap width). The shear gap may be in the range of from about 5 micrometers (0.0002 inch) and about 4 mm (0.016 inch).

The frequency of revolution of the HSD rotor may be greater than 250 rpm, greater than 500 rpm, greater than 1000 rpm, greater than 5000 rpm, greater than 7500 rpm, greater than 10,000 rpm, greater than 13,000 rpm, or greater than 15,000 rpm. The rotational frequency, flow rate, and temperature may be adjusted to get a desired product profile. If channeling should occur, and some reactants pass through unreacted, the rotational frequency may be increased to minimize undesirable channeling. Alternatively or additionally, unreacted reactants may be introduced into a second or subsequent HSD 40, or a portion of the unreacted reactants may be separated from the products and recycled to HSD 40.

HSD 40/40a may provide a tip speed in excess of 22.9 m/s (4500 ft/min) and may exceed 40 m/s (7900 ft/min), 50 m/s (9800 ft/min), 100 m/s (19,600 ft/min), 150 m/s (29,500 ft/min), 200 m/s (39,300 ft/min), or even 225 m/s (44,300 ft/min) or greater in certain applications. For the purpose of this disclosure, the term 'high shear' refers to mechanical rotor stator devices (e.g., colloid mills or rotor-stator dispersers) that are capable of tip speeds in excess of 5.1 m/s (1000 ft/min) or those values provided above and require an external mechanically driven power device to drive energy into the stream of products to be reacted. By contacting the reactants with the rotating members, which can be made from, coated with, or impregnated with stationary catalyst, significant energy is transferred to the reaction. Especially in instances where the reactants are gaseous, the energy consumption of the HSD 40/40a will be very low. The temperature may be adjusted to control the product profile and to extend catalyst life.

An approximation of energy input into the fluid (kW/L/min) can be estimated by measuring the motor energy (kW) and fluid output (L/min). As mentioned above, tip speed is the velocity (ft/min or m/s) associated with the end of the one or more revolving elements that is creating the mechanical force applied to the fluid. In embodiments, the energy expenditure is at least about 1000 W/m$^3$, 5000 W/m$^3$, 7500 W/m$^3$, 1 kW/m$^3$, 500 kW/m$^3$, 1000 kW/m$^3$, 5000 kW/m$^3$, 7500 kW/m$^3$, or greater. In embodiments, the energy expenditure of HSD 40/40a is greater than 1000 watts per cubic meter of fluid therein. In embodiments, the energy expenditure of HSD 40/40a is in the range of from about 3000 W/m$^3$ to about 7500 kW/m$^3$. In embodiments, the energy expenditure of HSD 40 is in the range of from about 3000 W/m$^3$ to about 7500 W/m$^3$. The actual energy input needed is a function of what reactions are occurring within the HSD, for example, endothermic and/or exothermic reaction(s), as well as the mechanical energy required for dispersing and mixing feedstock materials. In some applications, the presence of exothermic reaction(s) occurring within the HSD mitigates some or substantially all of the reaction energy needed from the motor input. When dispersing a gas in a liquid, the energy requirements are significantly less.

The shear rate is the tip speed divided by the shear gap width (minimal clearance between the rotor and stator). The shear rate generated in HSD 40/40a may be in the greater than 20,000 s$^{-1}$. In some embodiments the shear rate is at least 30,000 s$^{-1}$ or at least 40,000 s$^{-1}$. In some embodiments the shear rate is greater than 30,000 s$^{-1}$. In some embodiments the shear rate is at least 100,000 s$^{-1}$. In some embodiments the shear rate is at least 500,000 s$^{-1}$. In some embodiments the shear rate is at least 1,000,000 s$^{-1}$. In some embodiments the shear rate is at least 1,600,000 s$^{-1}$. In some embodiments the shear rate is at least 3,000,000 s$^{-1}$. In some embodiments the shear rate is at least 5,000,000 s$^{-1}$. In some embodiments the shear rate is at least 7,000,000 s$^{-1}$. In some embodiments the shear rate is at least 9,000,000 s$^{-1}$. In embodiments where the rotor has a larger diameter, the shear rate may exceed about 9,000,000 s$^{-1}$. In embodiments, the shear rate generated by HSD 40/40a is in the range of from 20,000 s$^{-1}$ to 10,000,000 s$^{-1}$.

In embodiments, a scaled-up version of the DISPAX® reactor is utilized. For example, in embodiments HSD 40/40a comprises a SUPER DISPAX REACTOR® DRS 2000. The HSD unit may be a DR 2000/50 unit, having a flow capacity of 125,000 liters per hour, or a DRS 2000/50 having a flow capacity of 40,000 liters/hour. Because residence time is increased in the DRS unit, the fluid therein is subjected to more shear.

First generator 220 comprises rotor 222 and stator 227. Second generator 230 comprises rotor 223, and stator 228. Third generator 240 comprises rotor 224 and stator 229. For each generator the rotor is rotatably driven by input 250 and rotates about axis 260 as indicated by arrow 265. The direction of rotation may be opposite that shown by arrow 265 (e.g., clockwise or counterclockwise about axis of rotation 260). Stators 227, 228, and 229 may be fixably coupled to the wall 255 of HSD 200. As mentioned hereinabove, each rotor and stator may comprise rings of complementarily-shaped tips, leading to several shear gaps within each generator.

As discussed above, a contact surface of the HSD 40/40a/200 may be made from, coated with, or impregnated by a suitable catalyst which catalyzes the desired reaction. In embodiments, a contact surface of one ring of each rotor or stator is made from, coated with, or impregnated with a different catalyst than the contact surface of another ring of the rotor or stator. Alternatively or additionally, a contact surface of one ring of the stator may be made from coated with or impregnated by a different catalyst than the complementary ring on the rotor. The contact surface may be at least a portion of the rotor, at least a portion of the stator, or both. The contact surface may comprise, for example, at least a portion of the outer surface of a rotor, at least a portion of the inner surface of a stator, or at least a portion of both.

HSD 200 may be configured so that the shear rate remains the same or increases or decreases stepwise longitudinally along the direction of the flow 260.

Generators 220, 230, and 240 may comprise a coarse, medium, fine, and super-fine characterization, having different numbers of complementary rings or stages on the rotors and complementary stators. Although generally less desirable, rotors 222, 223, and 224 and stators 227, 228, and 229 may be toothed designs. Each generator may comprise two or more sets of complementary rotor-stator rings. In embodiments, rotors 222, 223, and 224 comprise more than 3 sets of complementary rotor/stator rings. In embodiments, the rotor and the stator comprise no teeth, thus forcing the reactants to flow through the pores of a sintered material.

HSD 40/40a may be a large or small scale device. In embodiments, HSD 40/40a is used to process from less than 10 tons per hour to 50 tons per hour. In embodiments, HSD 40/40a processes 10 tons/h, 20 tons/h, 30 ton/hr, 40 tons/h, 50 tons/h, or more than 50 tons/h. Large scale units may produce 1000 gal/h (24 barrels/h). The inner diameter of the rotor may be any size suitable for a desired application. In embodiments, the inner diameter of the rotor is from about 12 cm (4 inch) to about 40 cm (15 inch). In embodiments, the diameter of the rotor is about 6 cm (2.4 inch). In embodiments, the outer diameter of the stator is about 15 cm (5.9 inch). In embodiments, the diameter of the stator is about 6.4 cm (2.5 inch). In some embodiments the rotors are 60 cm (2.4 inch) and the stators are 6.4 cm (2.5 inch) in diameter, providing a clearance of about 4 mm. In certain embodiments, each of three stages is operated with a superfine generator comprising a number of sets of complementary rotor/stator rings.

HSD 200 is configured for receiving at inlet 205 a fluid mixture from line 13. The mixture comprises reactants. In embodiments, the reactants comprise carbon and oxygen and/or steam. In embodiments, the reactants comprise hydrogen and carbon monoxide. In embodiments, at least one reactant is gaseous. In embodiments, at least one reactant is solid. Feed stream entering inlet 205 is pumped serially through generators 220, 230, and then 240, such that product is formed. Product exits HSD 200 via outlet 210 (and line 19 of FIG. 5). The rotors 222, 223, 224 of each generator rotate at high speed relative to the fixed stators 227, 228, 229, providing a high shear rate. The rotation of the rotors pumps fluid, such as the feed stream entering inlet 205, outwardly through the shear gaps (and, if present, through the spaces between the rotor teeth and the spaces between the stator teeth), creating a localized high shear condition. High shear forces exerted on fluid in shear gaps 225, 235, and 245 (and, when present, in the gaps between the rotor teeth and the stator teeth) through which fluid flows process the fluid and create product. The product may comprise a dispersion of unreacted or product gas and/or unreacted carbonaceous material in a continuous phase of liquid (e.g., liquid hydrocarbon product and/or slurry liquid and/or carrier liquid). The high shear-treated stream 19 may comprise unreacted solid carbonaceous material. Product exits HSD 200 via high shear outlet 210 (lines 19/19a of FIG. 5).

As mentioned above, in certain instances, HSD 200 comprises a DISPAX REACTOR® of IKA® Works, Inc. Wilmington, N.C. and APV North America, Inc. Wilmington, Mass. Several models are available having various inlet/outlet connections, horsepower, tip speeds, output rpm, and flow rate. Selection of the HSD will depend on throughput selection and desired particle, droplet or bubble size in dispersion in line 19/19a (FIG. 5) exiting outlet 210 of HSD 200. IKA® model DR 2000/4, for example, comprises a belt drive, 4M generator, PTFE sealing ring, inlet flange 25.4 mm (1 inch) sanitary clamp, outlet flange 19 mm (¾ inch) sanitary clamp, 2 HP power, output speed of 7900 rpm, flow capacity (water) approximately 300-700 L/h (depending on generator), a tip speed of from 9.4-41 m/s (1850 ft/min to 8070 ft/min). Scale up may be performed by using a plurality of HSDs, or by utilizing larger HSDs. Scale-up using larger models is readily performed, and results from larger HSD units may provide improved efficiency in some instances relative to the efficiency of lab-scale devices. The large scale unit may be a DISPAX® 2000/unit. For example, the DRS 2000/5 unit has an inlet size of 51 mm (2 inches) and an outlet of 38 mm (1.5 inches).

In embodiments HSD 40/40a or portions thereof are manufactured from refractory/corrosion resistant materials. For example, sintered metals, INCONEL® alloys, HASTELLOY® materials may be used. For example, ash from the coal may be very abrasive, so the rotors, stators, and/or other components of HSD 40 may be manufactured of abrasion resistant materials (e.g. sintered metal) in applications wherein carbonaceous material comprises coal. The HSD utilized for significant gas production will be designed as known in the art to withstand any increase in pressure anticipated therein during operation.

Vessel.

Vessel or reactor 10 (and 10a) can be any type of vessel in which a multiphase reaction can be propagated to carry out the above-described conversion reaction(s) or can be a separation vessel configured to separate gas, liquid, and/or solids introduced thereto via high shear-treated line 19/19a. In embodiments, vessel 10 is a separation vessel. Vessel 10/10a may be a continuous or semi-continuous stirred tank reactor, or one or more batch reactors may be employed in series or in parallel. In some applications vessel 10/10a may be a tower reactor, and in others a tubular reactor or multi-tubular reactor. Vessel 10/10a may be a fluidized bed reactor a fixed bed reactor or a slurry bed reactor. In embodiments, vessel 10a is a fixed bed reactor, a slurry bed reactor, or a fluidized bed reactor, as discussed further hereinbelow. A catalyst inlet line may be connected to vessel 10/10a for receiving a catalyst solution or slurry during operation of the system. In embodiments where a significant reaction occurs in HSD 40, vessel 10 may comprise one or more fractionators suitable for separating components. In embodiments, the components separated in vessel 10 are selected from synthesis gas, unreacted carbonaceous material, liquid hydrocarbon product, slurry liquid, or any combination thereof. In the embodiment of FIG. 5, vessel 10 comprises first vessel—10 outlet line 16, second vessel—10 outlet line 17 and third vessel—10 outlet line 20. In the embodiment of FIG. 5, vessel 10a comprises first vessel—10a outlet line 16a and second vessel—10a outlet line 17a.

Vessel 10/10a may include one or more of the following components: stirring system, heating and/or cooling capabilities, pressure measurement instrumentation, temperature measurement instrumentation, one or more injection points, and level regulator, as are known in the art of reaction vessel design. For example, a stirring system may include a motor driven mixer. A heating and/or cooling apparatus may comprise, for example, a heat exchanger. Alternatively, as much of the desired reaction may occur within the HSD in some embodiments, vessel 10/10a may serve primarily as a storage vessel in some cases. Although generally less desired, in some applications vessel 10/10a may be omitted, particularly if multiple high shears/reactors are employed in series, as further described below.

Slurry Production Apparatus.

System 100 may further comprise slurry production apparatus 15. Slurry production apparatus is any apparatus suitable for providing a slurry of carbonaceous material in suitable slurry liquid or diluent. The diluent (slurry liquid) may be aqueous, non-aqueous. The slurry liquid may comprise one or more component selected from oils, water, and alcohols. The carbonaceous material may be coal, coke, or a combination thereof. In embodiments, the carbonaceous material is selected from lignite, anthracite, bituminous, and sub-bituminous coals.

The term "coal" is used herein to describe a variety of fossilized plant materials. No two coals are exactly alike. Heating value, ash melting temperature, sulfur and other impurities, mechanical strength, and many other chemical and physical properties must be considered when matching specific coals to a particular application.

Coal is classified into four general categories, or 'ranks.' They range from lignite through sub-bituminous and bituminous to anthracite, reflecting the progressive response of individual deposits of coal to increasing heat and pressure. The carbon content of coal supplies most of its heating value, but other factors also influence the amount of energy it contains per unit of weight. The amount of energy in coal is expressed in British thermal units (BTU) per pound. A BTU is the amount of heat required to raise the temperature of one pound of water one degree Fahrenheit.

In embodiments, the carbonaceous material comprises lignite. Lignite ranks the lowest and is the youngest of the coals. Lignite is a geologically young coal which has the lowest carbon content, 25-35 percent, and a heat value ranging between 4,000 and 8,300 BTU/lb. In embodiments, the carbonaceous material comprises lignite which has a carbon content of around 25-35% and a high inherent moisture content (may be, e.g., as high as 66%). The ash content of lignite may be in the range of from about 6% to 19%, compared with 6% to 12% for bituminous coal. The heat content of the lignite may range from 10 to 20 MJ/kg (9 to 17 million BTU per short ton) on a moist, mineral-matter-free basis. The heat content of the lignite may average about 13 million BTU/ton (15 MJ/kg), on the as-received basis (i.e., containing both inherent moisture and mineral matter).

Lignite has a high content of volatile matter which may make it easier to convert into gas and liquid petroleum products than higher ranking coals. However, its high moisture content and susceptibility to spontaneous combustion can cause problems in transportation, storage, and handling.

In embodiments, the carbonaceous material comprises anthracite. Anthracite is the highest of the metamorphic rank, having the highest carbon content. In embodiments, the carbonaceous material comprises anthracite containing between 86 and 98 percent carbon content. The anthracite may have a heat value of nearly 15,000 BTU/lb. In embodiments, the anthracite has a carbon content in the range of between 92% and 98%. The term 'anthracite' is applied to those varieties of coal which do not give off tarry or other hydrocarbon vapors when heated below their point of ignition.

Anthracite differs from ordinary bituminous coal by its greater hardness, its higher relative density of 1.3-1.4, and luster, which is often semi-metallic with a mildly brown reflection. It contains a high percentage of fixed carbon and a low percentage of volatile matter. It is also free from included soft or fibrous notches and does not soil the fingers when rubbed. Anthracitization is the transformation of bituminous into anthracite.

The moisture content of fresh-mined anthracite generally is less than 15 percent. The heat content of the anthracite used as carbonaceous material may range from 22 to 28 million BTU per short ton (26 to 33 MJ/kg) on a moist, mineral-matter-free basis. The heat content of the anthracite coal may average 25 million BTU/ton (29 MJ/kg), on the as-received basis (i.e., containing both inherent moisture and mineral matter).

In embodiments, the carbonaceous material comprises bituminous and/or sub-bituminous coals, which rank below anthracite and, for the most part, contain less energy per unit of weight.

In embodiments, the carbonaceous material comprises bituminous coal. Bituminous coal has a carbon content ranging from 45 to 86 percent carbon and a heat value of 10,500 to 15,500 BTU/lb. In embodiments, the carbonaceous material comprises bituminous coal having a carbon content in the range of from about 60% to about 80%; the rest is balance being water, air, hydrogen, and/or sulfur. The heat content of the bituminous coal used as carbonaceous material may range from 21 million to 30 million BTU/ton (24 to 35 MJ/kg) on a moist, mineral-matter-free basis.

In embodiments, the carbonaceous material comprises sub-bituminous coal. Ranking below bituminous is sub-bituminous coal with 35-45 percent carbon content and a heat value between 8,300 and 13,000 BTU/lb. Although its heat value is lower, this coal generally has a lower sulfur content than other types, which may make it attractive for use herein. In embodiments, the sub-bituminous coal has a sulfur content less than 1% by weight, making it attractive to reduce $SO_2$ production. Sub-bituminous coal is a type of coal whose properties range from those of lignite to those of bituminous coal and is primarily used as fuel for steam-electric power generation. In embodiments, the sub-bituminous coal contains 15-30% inherent moisture by weight. The heat content of the sub-bituminous coal used as carbonaceous material may be in the range of from 8300 to 11,500 BTU/lb or 19,306 to 26,749 kJ/kg. The relatively low density and high water content renders some types of sub-bituminous coals susceptible to spontaneous combustion if not packed densely during storage in order to exclude free air flow, so handling should be adjusted accordingly, as known in the art.

In embodiments, the carbonaceous material comprises coke. Slurry production apparatus 15 may thus comprise coke-producing apparatus. Pyrolysis is the chemical decomposition of a condensed substance by heating. Pyrolysis is a special case of thermolysis, most commonly used for organic materials. Pyrolysis is used on a massive scale to turn coal into coke for metallurgy, especially steelmaking. Coke can also be produced from the solid residue left from petroleum refining. The pyrolysis production apparatus may be configured for producing coke from starting materials typically contain hydrogen, nitrogen or oxygen atoms combined with carbon into molecules of medium to high molecular weight. The coke may be produced by a coking process comprising heating the material in closed vessel(s) to very high temperatures (up to 2000° C.), so that those molecules are broken down into lighter volatile substances, which leave the vessel, and a porous but hard residue that is mostly carbon and inorganic ash. The amount of volatiles varies with the source material, but is typically 25-30% of it by weight.

The slurry production apparatus 15 may comprise crushing/grinding/pulverizing devices for comminuting the carbonaceous material to a desired size. The carbonaceous material may be processed to a powder having an average particle size of less than 80 μm, less than 60 μm, or less than 40 μm, for example. In embodiments, the carbonaceous comprises coal and the coal powder has a particle size such that 70 to 80% of the powder passes through a 200-mesh sieve (74μ). In embodiments, the slurry is a coal slurry having a particle size distribution (PSD) with 10, 20, 30, 40, 50, 60, 70, 80, or 90% of the particles smaller than about 80, 70, 60, 50, 40, 30, or 20 microns. A coal slurry may be prepared by any methods known in the art, for example, as described in the book Alternative Fuels by Sunggyu Lee; CRC Press, 1996, ISBN 1560323612, 9781560323617. In embodiments the coal can first be crushed and classified to a powder by means of devices such as, but not limited to, roller mills and cyclone separators. This processing may be followed by direct conversion to a slurry via means known in the art, such as via wet milling devices, including, but not limited to, attritor mills and ultrasonic mills. Alternatively various colloid mills can be used to prepare slurries from coal.

The slurry production apparatus 15 may further comprise mixing apparatus for combining powdered carbonaceous material with slurry liquid. In embodiments, the slurry liquid is aqueous. In embodiments, the slurry liquid is non-aqueous based. The composition of the slurry may be adjusted depending on the carbonaceous material, the dispersible gas or vapor 22 utilized and the operating conditions within HSD 40 such that synthesis gas having a desired composition is produced.

Heat Transfer Devices.

Internal or external heat transfer devices for heating the fluid to be treated are also contemplated in variations of the system. For example, the reactants may be preheated via any method known to one skilled in the art. Some suitable locations for one or more such heat transfer devices are between pump 5 (5a) and HSD 40 (40a), between HSD 40 (40a) and flow line 19 (19a), and between flow line 19 (19a) and pump 5 (5a) when fluid in flow line 19 (19a) is recycled to HSD 40 (40a). HSD may comprise an inner shaft which may be cooled, for example water-cooled, to partially or completely control the temperature within the HSD. Some non-limiting examples of such heat transfer devices are shell, tube, plate, and coil heat exchangers, as are known in the art.

Pumps.

Pump 5 (5a) is configured for either continuous or semi-continuous operation. The capabilities and configuration of pump 5 are described herein above. In addition to pump 5/5a, one or more additional, high pressure pumps may be included in the system illustrated in FIG. 5. For example, a booster pump, which may be similar to pump 5/5a, may be included between HSD 40 (40a) and flow line 19 (19a) for boosting the pressure into flow line 19 (19a).

Synthesis Gas Utilization Apparatus.

System 100 may further comprise synthesis gas utilization apparatus 30. Synthesis gas utilization apparatus 30 can be any apparatus known in the art for utilization of synthesis gas for producing value-added product, or may comprise a product sales line. In embodiments, synthesis gas utilization apparatus 30 comprises apparatus for the production of hydrocarbon liquids (e.g. FT hydrocarbons) and/or alcohols from synthesis gas. The synthesis gas utilization apparatus 30 can comprise apparatus for reacting synthesis gas in the presence of FT catalyst to produce FT product comprising liquid hydrocarbons. In embodiments, the synthesis gas utilization apparatus comprises a slurry bed reactor operated with a circulating slurry of FT catalyst, a fixed bed reactor comprising a fixed bed of FT catalyst, or a fluidized bed comprising a fluidized bed of FT catalyst. In embodiments, synthesis gas production apparatus 30 comprises apparatus for the production of methanol from synthesis gas. In embodiments, both liquid hydrocarbons and alcohols are produced in synthesis gas utilization apparatus 30.

In embodiments, as indicated in FIG. 5, synthesis gas utilization apparatus 30 comprises a second HSD 40a and a second pump 5a. HSD 40a and pump 5a are similar or identical respectively to HSD 40 and pump 5 described above. Line 21a is connected to pump 5a for introducing liquid carrier into pump 5a. Line 13a connects pump 5a to HSD 40a, and line 19a carries a dispersion out of HSD 40a. Synthesis gas utilization apparatus 30 may further comprise a vessel 10a. As mentioned hereinabove, vessel 10a may be an FT reactor. In embodiments, vessel 10 may be a fluidized, slurry, or fixed bed reactor. Vessel 10a may be fluidly connected to HSD 40a via dispersion flow line 19a. Vessel 10a may comprise one or more outlet lines. For example, in the embodiment of FIG. 5, vessel 10a comprises first vessel—10a outlet line 16a, second vessel—10a outlet line 17a.

Synthesis gas utilization apparatus 30 may contain or utilize an FT catalyst. A variety of catalysts can be used to catalyze Fischer-Tropsch reactions, but the most common are the transition metals cobalt, iron, and ruthenium. Nickel can also be used, but tends to favor methane formation. Cobalt seems to be the most active catalyst, although iron also performs well and can be more suitable for low-hydrogen-content synthesis gases such as those derived from coal due to its promotion of the water-gas-shift reaction. In addition to the active metal the catalysts can contain a number of promoters, including potassium and copper, as well as high-surface-area binders/supports such as silica, alumina, and/or zeolites.

Unlike the other metals used for this process (Co, Ni, Ru) which remain in the metallic state during synthesis, iron catalysts tend to form a number of chemical phases, including various iron oxides and iron carbides during the reaction. Control of these phase transformations can be important in maintaining catalytic activity and preventing breakdown of the catalyst particles.

The Fischer-Tropsch catalysts are notoriously sensitive to the presence of sulfur-containing compounds among other poisons. The sensitivity of the catalyst to sulfur is higher for cobalt-based catalysts than for their iron counterparts. In embodiments in which the synthesis gas produced via the disclosed method comprises a substantial amount of sulfur, cleanup apparatus may be inserted in system 100 upstream of the FT production apparatus. For example, one or more AGRU (acid gas removal unit) or scrubber may be configured to remove sulfur and sulfur-compounds from the produced synthesis gas prior to FT reaction. Additionally, one or more $CO_2$ removal units may be positioned upstream of one or more FT reactors for removing at least a portion of the carbon dioxide from the synthesis gas prior to FT reaction. For example, one or more AGRU (acid gas removal unit) may be configured to remove carbon dioxide from the produced synthesis gas prior to FT reaction. In embodiments, alcohols are desired liquid product along with liquid hydrocarbons, and removal of carbon dioxide is unnecessary and undesired. In such embodiments, no $CO_2$ removal units are incorporated.

Generally, if the synthesis gas has a high hydrogen to carbon ratio, and the water-gas-shift is not needed, the FT catalyst may comprise cobalt, due to the higher activity of the cobalt catalyst. Iron catalysts may be preferred when water gas shift is desirable. While iron catalysts are also susceptible to sulfur poisoning from coal with high sulfur content, the lower cost of iron makes sacrificial catalyst at the front of a reactor bed economical. Also, as mentioned earlier, iron can catalyze the water-gas-shift to increase the hydrogen to carbon ratio to make the reaction more favorably selective, in some embodiments.

System for Utilization of Synthesis Gas.

Also disclosed is a system for the utilization of synthesis gas to produce liquid product comprising hydrocarbons and alcohols. Such a system comprises synthesis gas utilization apparatus 30, but may or may not include high shear device 40, pump 5, and/or vessel 10 for the production of the synthesis gas. That is, the synthesis gas utilization apparatus 30 may be combined with apparatus for the production of synthesis gas other than that described above or may be utilized with synthesis gas from any source (e.g., purchased synthesis gas, synthesis gas obtained via natural gas splitting, etc).

High Shear Process for Producing Synthesis Gas.

Figure 6:
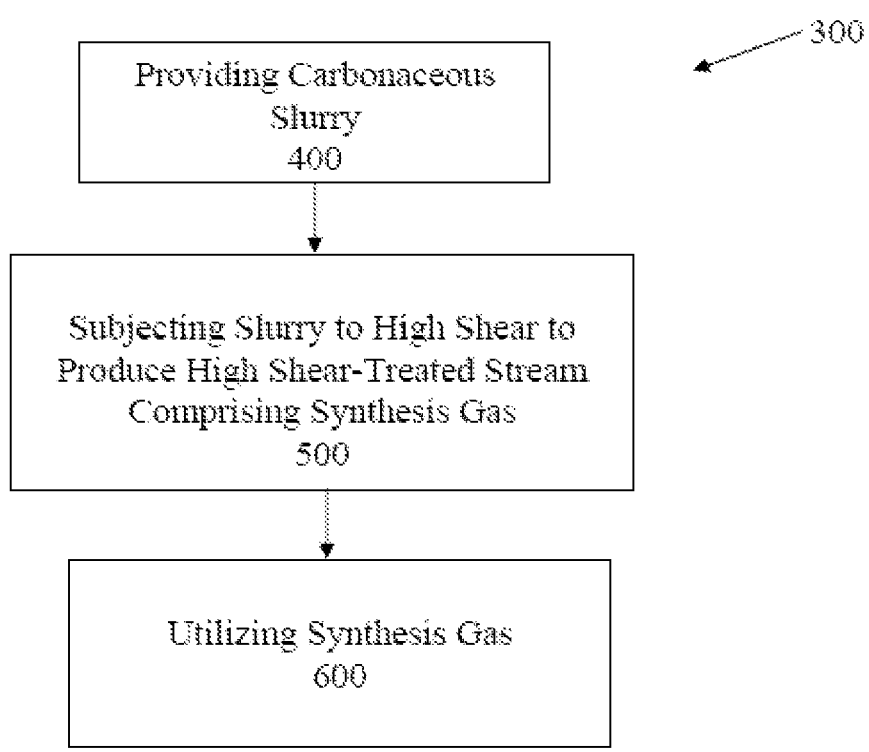
FIG. 6 is a schematic of a method of producing synthesis gas according to an embodiment of this disclosure.

A process for producing synthesis gas from slurry comprising carbonaceous material will now be described with respect to FIG. 6 which is a schematic of a method 300 of producing synthesis gas according to an embodiment of this disclosure. Process 300 comprises providing carbonaceous slurry 400; subjecting the slurry to high shear to produce a high shear-treated stream comprising synthesis gas 500; and utilizing synthesis gas 600.

Providing Carbonaceous Slurry 400.

Providing a carbonaceous slurry 400 may comprise mixing one or more carbonaceous material with a suitable liquid or diluent to form a slurry thereof. The liquid may be any liquid known in the art to be suitable for producing a slurry. The liquid may be aqueous or nonaqueous. For example, the liquid of the slurry may be selected from water, oils, alcohols, and combinations thereof. The carbonaceous material may be selected from coal and coke. In embodiments, the coke is produced by pyrolyzing coal. In embodiments, coke is produced or obtained from coking of residuum in a refinery. In embodiments the carbonaceous material comprises lignite, anthracite, bituminous, or a combination thereof. Providing carbonaceous slurry may further comprise obtaining coal and comminuting the coal to provide a powder having an average powder size less than a desired size. Providing a slurry may further comprise comminuting a carbonaceous material to powdered form. In embodiments, the carbonaceous material powder has an average particle size of less than about 40, less than about 500, or less than about 1000 microns. The ultimate particle size of the carbonaceous material remaining in the dispersion will be determined by the shear gap of the HSD and/or the pore size of the sintered metal coated rotor and/or stator of the HSD.

Subjecting Slurry to High Shear to Produce High Shear-Treated Stream Comprising Synthesis Gas 500.

Process 300 further comprises subjecting the slurry to high shear to produce a high shear-treated stream comprising synthesis gas 500. Subjecting the slurry to high shear 500 may comprise subjecting the slurry to a shear rate of at least 20,000 s$^{-1}$, above 30,000 s$^{-1}$, or greater, as further discussed hereinbelow. In embodiments, subjecting the slurry to high shear 500 comprises introducing the slurry into a HSD 40, as indicated in FIG. 5. Subjecting the slurry to high shear may comprise forming a dispersion comprising bubbles of dispersible gas or synthesis gas or particles of carbonaceous material dispersed in the slurry liquid. In embodiments, the bubbles and/or particles in the dispersion have an average diameter of less than or about 5, 4, 3, 2, or 1 μm. In embodiments, the bubbles and/or particles in the dispersion have an average particle diameter in the nanometer range, the micron range, or the submicron range.

Referring now to FIG. 5, subjecting the slurry to high shear 500 may comprise introducing the slurry from slurry production apparatus 15 into HSD 40. Pump 5 is used to pump the slurry into HSD 40. If desired, gas (or water vapor) may be introduced into pressurized slurry line 13 or directly into HSD 40 via dispersible gas (or vapor) line 22. The composition and utilization of dispersible gas can be selected according to the carbonaceous materials to be converted to synthesis gas, the operating conditions and/or the desired H$_2$:CO mole ratio in the resulting synthesis gas product. For example, when the slurry comprises carbonaceous material having high carbon and insufficient hydrogen content (e.g., anthracite and/or bituminous), hydrogen may be introduced into HSD 40 via dispersible gas line 22. In embodiments, oxygen may be added via dispersible gas line 22. In embodiments, associated gas may be added via dispersible gas line 22. In embodiments, water vapor (steam) is introduced via dispersible gas line. HSD 40 may be a rotor-stator device as described hereinabove. In other embodiments, the dispersible gas or vapor is present in the slurry as provided in slurry production apparatus 15 or is introduced directly into HSD 40.

In embodiments, associated gas is combined with the slurry upstream or within the HSD 40. For example, if system 100 is incorporated into a coal mining operation, and associated gas is recovered from a coal deposit with the coal to be used as carbonaceous material, the associated gas may be introduced into HSD 40 along with the carbonaceous material. The associated gas may be incorporated into the slurry in slurry production apparatus 15, introduced separately via dispersible gas line 22, or introduced directly into HSD 40. Addition of associated gas in this manner may be used to increase the H$_2$:CO mole ratio in the resulting synthesis gas produced in HSD 40. As mentioned herein with regard to Eq. (3), natural gas has a greater hydrogen content (from x=4 to x~2.5) than coal. The term 'associated gas is used herein to refer to gas found deposited in or above coal, e.g. coalbed methane or coal seam gas. The associated gas comprises methane and may comprise various other gases, as known in the art. Coalbed methane may be 'sweet gas' comprising little hydrogen sulfide. Coalbed methane may contain very little heavier hydrocarbons such as propane or butane, and no natural gas condensate. The associated gas may contain up to a few percent carbon dioxide.

An inert gas such as nitrogen may be used to fill reactor 10 and purge it of any air and/or oxygen prior to operation of system 100. Pump 5 is operated to pump the slurry through line 21, and to build pressure and feed HSD 40, providing a controlled flow throughout high shear (HSD) 40 and high shear system 100. In some embodiments, pump 5 increases the pressure of the HSD inlet stream in line 13 to greater than 200 kPa (2 atm) or greater than about 300 kPa (3 atmospheres). In this way, high shear system 100 may combine high shear with pressure to enhance production of synthesis gas.

In embodiments, dispersible gas is continuously fed into the slurry stream 13 to form the high shear feed stream (e.g. a gas-liquid-solid feed stream). Within high shear device 40, dispersible gas and/or product synthesis gas and/or carbonaceous material may be highly dispersed such that nanobubbles and/or microbubbles of gas and/or nanoparticles and/or microparticles of the carbonaceous material are formed. The temperature and shear within HSD 40 are controlled to produce synthesis gas having a desired composition. For example, the temperature and shear to which the HSD contents are subjected may be selected/adjusted to produce synthesis gas comprising hydrogen and carbon monoxide in a desired ratio. The desired synthesis gas H$_2$:CO mole ratio may be in the range of from about 0.5 to 2, in the range of from 0.5 to 1.5, in the range of from about 0.7 to 1.5, in the range of from about 0.9 to 1.3. The desired synthesis gas may have a $H_2$:CO mole ratio of about 1:1.

Within HSD 40, the contents are subjected to high shear. It is also envisaged that a catalyst may additionally be present in the HSD 40 in certain embodiments. Components of the carbonaceous material (e.g. metals in the coal ash) may serve to catalyze production on synthesis gas and/or production of liquid hydrocarbons from the synthesis gas. In embodiments, additional solid, gaseous or liquid phase catalyst may be introduced to HSD 40 via inlet line 13, line 21, or line 22. In an exemplary embodiment, the high shear device comprises a commercial disperser such as IKA® model DR 2000/4, a high shear, three stage dispersing device configured with three rotors in combination with stators, aligned in series, as described above. The disperser is used to subject the slurry to high shear. The rotor/stator sets may be configured as illustrated in FIG. 2, for example. In such an embodiment, the feed enters the high shear device via line 13 and enter a first stage rotor/stator combination having circumferentially spaced first stage shear openings. The coarse dispersion (comprising solid carbonaceous materials and/or gas, i.e. dispersible gas from line 22 or product synthesis gas, dispersed in liquid carrier of slurry) exiting the first stage enters the second rotor/stator stage, which has second stage shear openings. The reduced particle-size dispersion emerging from the second stage enters the third stage rotor/stator combination having third stage shear openings. The rotors and stators of the generators may have circumferentially spaced complementarily-shaped rings. A high shear-treated stream exits the high shear device via line 19. In some embodiments, the shear rate increases stepwise longitudinally along the direction of the flow 260, or going from an inner set of rings of one generator to an outer set of rings of the same generator. In other embodiments, the shear rate decreases stepwise longitudinally along the direction of the flow, 260, or going from an inner set of rings of one generator to an outer set of rings of the same generator (outward from axis 200). For example, in some embodiments, the shear rate in the first rotor/stator stage is greater than the shear rate in subsequent stage(s). For example, in some embodiments, the shear rate in the first rotor/stator stage is greater than or less than the shear rate in a subsequent stage(s). In other embodiments, the shear rate is substantially constant along the direction of the flow, with the stage or stages being the same. If HSD 40 includes a PTFE seal, for example, the seal may be cooled using any suitable technique that is known in the art. The HSD 40 may comprise a shaft in the center which may be used to control the temperature within HSD 40. For example, the slurry stream flowing in line 13 (or the liquid used to create the slurry of carbonaceous material) may be used to cool the seal and in so doing be preheated as desired prior to entering the high shear device. Heat may be added to HSD 40 (via the shaft or elsewhere, such as external to HSD 40) to promote production of synthesis gas, in embodiments.

The rotor(s) of HSD 40 may be set to rotate at a speed commensurate with the diameter of the rotor and the desired tip speed. As described above, the HSD (e.g., colloid mill or toothed rim disperser) has either a fixed clearance between the stator and rotor or has adjustable clearance.

HSD 40 serves to subject the slurry to high shear. In some embodiments of the process, the transport resistance of the reactants is reduced by operation of the high shear device such that the velocity of the one or more reaction (i.e. production of synthesis gas) is increased by greater than a factor of about 5. In some embodiments, the velocity of the reaction is increased by at least a factor of 10. In some embodiments, the velocity is increased by a factor in the range of about 10 to about 100 fold. In some embodiments, HSD 40 delivers at least 300 L/h at a nominal tip speed of at least 22 m/s (4500 ft/min), 40 m/s (7900 ft/min), and which may exceed 225 m/s (45,000 ft/min) or greater. The power consumption may be about 1.5 kW or higher as desired. Although measurement of instantaneous temperature and pressure at the tip of a rotating shear unit or revolving element in HSD 40 is difficult, it is estimated that the localized temperature seen by the intimately mixed reactants may be in excess of 500° C. and at pressures in excess of 500 kg/cm$^2$ under high shear conditions.

Conditions of temperature, pressure, space velocity, dispersible gas (line 22) composition, and slurry composition may be adjusted to produce a desired product profile (and maintain safety). The use of HSD 40 may allow for production of synthesis gas having a desirable $H_2$:CO ratio. In some embodiments, the operating conditions of system 100 comprise a temperature of at or near ambient temperature and global pressure of at or near atmospheric pressure. If the carrier fluid/source of $H_2$ is liquefied, for example associated gas (natural gas), it may be more desirable to operate the system at conditions under which the carrier fluid (e.g. the associated gas) remains a liquid and maintains a liquid/solid slurry with the solid (e.g., with the coal or other hydrocarbonaceous material). Because the HSD 40 provides high pressure (e.g. 150,000 psi) at the tips of the rotors, the temperature of the reaction may be reduced relative to conventional gasification systems in the absence of high shear. In embodiments, the operating temperature is less than about 70% of the conventional operating temperature, or less than about 60% of the conventional operating temperature, or less than about 50% of the conventional operating temperature for the same reaction(s)

The residence time within HSD 40 is typically low. For example, the residence time can be in the millisecond range, can be about 10, 20, 30, 40, 50, 60, 70, 80, 90 or about 100 milliseconds, can be about 100, 200, 300, 400, 500, 600, 700, 800, or about 900 milliseconds, can be in the range of seconds, or can be any range thereamong.

Utilizing Synthesis Gas 600.

Process 300 may further comprise utilizing synthesis gas 600. Utilizing synthesis gas 600 may comprise utilizing the synthesis gas or a component thereof (e.g. hydrogen) directly as a fuel or producing a value product from the synthesis gas. It is noted that the method of utilizing synthesis gas 601 may be utilized for the production of product from any synthesis gas, not only for the production of product from synthesis gas obtained via high shear gasification of carbonaceous materials as described hereinabove. That is, another aspect of this disclosure is a method of producing product (e.g., comprising one or more components selected from liquid hydrocarbons and alcohols) from synthesis gas obtained via any system and/or process. For example, the synthesis gas may be provided by the herein disclosed gasification of carbonaceous materials via high shear, may be obtained via conventional gasification (also called steam reforming) of carbonaceous material (e.g. coal, biomass, or natural gas), may be obtained via splitting of natural gas, may be obtained via partial combustion of hydrocarbons, or may be obtained by some combination thereof.

Figure 7:
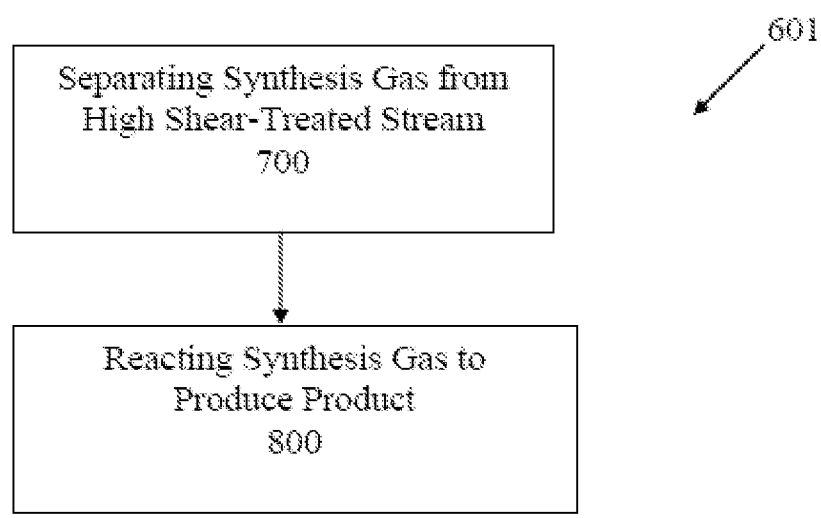
FIG. 7 is a schematic of a method of utilizing synthesis gas according to an embodiment of this disclosure.

In embodiments, synthesis gas produced in HSD 40 and/or obtained from another source/method is burned directly in internal combustion engines, used to produce methanol and hydrogen, or converted into product comprising liquid hydrocarbons and/or alcohols. As indicated in FIG. 7, which is a schematic of a method of utilizing synthesis gas 601 according to an embodiment of this disclosure, utilizing synthesis gas may comprise separating synthesis gas from the high shear-treated stream 700 and reacting the synthesis gas (which may further comprise carbon dioxide) to produce products 800.

Separating Synthesis Gas from High Shear-Treated Stream 700.

A high shear-treated stream exits high shear device 40 at high shear outlet line 19. High shear-treated stream 19 will typically comprise synthesis gas; unreacted carbonaceous material; slurry liquid; and co-products including hydrocarbons that may be formed by reaction of carbonaceous material, e.g. by reaction of carbon monoxide and hydrogen (and catalysis by components of carbonaceous material), such co-products including but not limited to C1-C4 compounds, CO, $O_2$, $H_2O$, and sulfur compounds such as $H_2S$. Utilizing synthesis gas may comprise at step 700 separating synthesis gas from high shear-treated stream 19. Utilizing synthesis gas may comprise separating a product comprising synthesis gas from the high shear-treated stream. Separating a product comprising synthesis gas from the high shear-treated stream at 700 may comprise separating synthesis gas and one or more co-products from the high shear-treated stream. Separating a product comprising synthesis gas from the high shear-treated stream at 700 may comprise separating carbonaceous material, slurry liquid, one or more co-products, or a combination thereof from the high shear-treated stream, leaving a product comprising synthesis gas.

Stream 19 may optionally enter vessel 10. Synthesis gas may be separated from other components of high shear-treated stream 19 by any means known in the art. Separating synthesis gas from high shear-treated stream in line 19 may comprise introducing the high shear-treated stream into vessel 10. As mentioned hereinabove, vessel 10 may be a separation unit, or may be more than one separation unit. Various components of high shear-treated stream 19 (e.g. product synthesis gas, one or more co-products such as hydrocarbon products that may have formed within HSD 40, slurry liquid, and unreacted carbonaceous material, e.g. coal) may be extracted from vessel(s) 10 or can be extracted from one or more separation units downstream of vessel 10. Any suitable separation method known in the art may be used to separate the various components of high shear-treated stream 19. For example, one or more selected from vapor/liquid separations, solid/liquid separations, distillations, and other separation means may be used to separate the desired components exiting HSD 40 and/or vessel 10.

In embodiments, synthesis gas product is removed via first vessel—10 outlet line 16. The gas removed from vessel 10 via first vessel—10 outlet line 16 may comprise other components in addition to synthesis gas, e.g. various amounts of carbon dioxide, methane, alcohols, hydrogen sulfide and/or diesel. Slurry liquid and hydrocarbon product may be removed via second vessel—10 outlet line 17. Unreacted carbonaceous material may be removed from vessel 10 via third vessel—10 outlet line 20. Alternatively, slurry liquid and unreacted carbonaceous material may be removed together, e.g. via third vessel—10 outlet line 20. Vessel 10 may comprise more than one separation unit as known in the art. For example, a liquid stream comprising liquid hydrocarbons produced in HSD 40 and slurry liquid may be removed from vessel 10 or a first separation vessel and a second separation vessel may be used to separate the slurry liquid from the liquid hydrocarbons, in certain embodiments.

Separated slurry liquid and/or unreacted carbonaceous material may be recycled to HSD 40, for example by introduction into line 21, line 13, or HSD 40 via second vessel—10 outlet line 17 and/or third vessel—10 outlet line 20.

Product synthesis gas, which may be extracted from vessel 10 via first vessel—10 outlet line 16, may comprise hydrogen and carbon monoxide in a desired molar ratio, as discussed above. The synthesis gas may further comprise carbon dioxide and lower molecular weight hydrocarbons, e.g. methane. In embodiments, the product synthesis gas comprises less than about 50 mole percent, 40%, 30%, or 20% carbon dioxide. If hydrogen and sulfur are present in the HSD, $H_2S$ can be formed. In embodiments, the product synthesis gas comprises less than about 20 mole percent, 10%, or 5% hydrogen sulfide. As discussed hereinbelow, in embodiments (e.g., for use with $CO_2$ sensitive FT catalyst) $CO_2$, $H_2S$, or other component of the synthesis-gas containing stream removed from HSD 40 and/or vessel 10 can be removed.

Reacting Synthesis Gas to Produce Products 800.

Utilizing synthesis gas may further comprise reacting synthesis gas under suitable conditions to produce product 800. Step 800 may be catalytic and may comprise operating at Fischer-Tropsch (FT) operating conditions. In embodiments, reacting synthesis gas to produce product 800 comprises any means known in the art for reacting synthesis gas from HSD 40 to produce FT hydrocarbons. The FT products may be formed as known in the art, or may be produced utilizing a HSD, as described hereinbelow, and/or as described in U.S. patent application Ser. No. 12/138,269 (now U.S. Pat. No. 8,133,925), which is hereby incorporated herein in its entirety for all purposes not inconsistent with this disclosure.

A variety of synthesis gas compositions can be used for FT. For cobalt-based catalysts the optimal $H_2$:CO ratio is around 1.8-2.1. Iron-based catalysts promote the water-gas-shift reaction and thus can tolerate significantly lower ratios. If the synthesis gas has a relatively low $H_2$:CO ratio (<1), iron catalyst may be desirable. Depending on the composition of the synthesis gas (produced in HSD 40 or obtained via other means), utilizing synthesis gas 601 may further comprise removing at least a portion of the sulfur and/or sulfur-containing compounds from the synthesis gas prior to step 800 and/or removing at least a portion of the carbon dioxide from the synthesis gas prior to step 800. For example, scrubbing (via one or more scrubbers) may be utilized to reduce the sulfur content of the resulting syngas. Acid gas removal (via one or more acid gas removal units or AGRUs) may be utilized to reduce the carbon dioxide and/or hydrogen sulfide content of the synthesis gas.

The Fischer-Tropsch process (or Fischer-Tropsch synthesis) is a catalyzed chemical reaction in which synthesis gas, a mixture of carbon monoxide and hydrogen, is converted into liquid hydrocarbons of various forms. The most common catalysts are based on iron and cobalt, although nickel and ruthenium have also been used. The principal purpose of this process is to produce a synthetic petroleum substitute, typically from coal, natural gas or biomass, for use as synthetic lubrication oil or as synthetic fuel. This synthetic fuel runs trucks, cars, and some aircraft engines. The use of diesel is increasing in recent years.

The Fischer-Tropsch process involves a variety of competing chemical reactions, which lead to a series of desirable products and undesirable byproducts. The most important reactions are those resulting in the formation of alkanes. These can be described by chemical equations of the form:

$$(2n+1)H_2 + nCO \rightarrow C_nH_{(2n+2)} + nH_2O \quad (7)$$

where n is a positive integer. The simplest of these (n=1), results in formation of methane, which is generally considered an unwanted byproduct (particularly when methane is the primary feedstock used to produce the synthesis gas). Process conditions and catalyst composition are usually chosen to favor higher order reactions (n>1) and thus minimize methane formation. Most of the alkanes produced tend to be straight-chained, although some branched alkanes are also formed. In addition to alkane formation, competing reactions result in the formation of alkenes, as well as alcohols and other oxygenated hydrocarbons. Usually, only relatively small quantities of these non-alkane products are formed, although catalysts favoring some of these products have been developed.

Another important reaction is the water gas shift reaction, WGSR, (6) hereinabove. Although the WGS reaction results in formation of unwanted $CO_2$, it can be used to shift the $H_2$:CO ratio of the incoming synthesis gas. This will be desirable if the synthesis gas utilized in step 800 has a ratio of about 0.7. If the mole ratio of hydrogen to carbon monoxide is higher, e.g. about 2, catalyst that does not promote WGSR may be utilized. The water gas shift reaction is sensitive to temperature, with the tendency to shift towards reactants as temperature increases due to Le Chatelier's principle.

It should be noted that, according to published data on the current commercial implementations of the coal-based Fischer-Tropsch process, these plants can produce as much as 7 metric tons of $CO_2$ per metric ton of liquid hydrocarbon products (excluding the reaction water product). This is due in part to the high energy demands required by the gasification process, and in part by the design of the process as implemented. Utilization of the process disclosed herein may allow production of reduced amounts of $CO_2$ and/or conversion of the $CO_2$ to product (e.g., alcohols).

In embodiments, step 800 comprises catalytically reacting synthesis gas under FT operating conditions to produce FT product and utilizes typical FT operating temperatures in the temperature range of 150-300° C. (302-572° F.). Generally, higher temperatures lead to faster reactions and higher conversion rates, but also tend to favor methane production. The use of an HSD 40a, as described below, may allow the use of lower than conventional FT operating temperatures, and reduced undesirable methane production. The temperature for catalytically reacting synthesis gas under FT operating conditions to produce FT product may be maintained at the low to middle part of the above range. Increasing the pressure generally leads to higher conversion rates and also favors formation of long-chained alkanes both of which are desirable. Typical pressures are in the range of one to several tens of atmospheres. Chemically, even higher pressures would be favorable, but the benefits may not justify the additional costs of high-pressure equipment. The use of HSD 40a, as discussed below, may enable more desirable product distribution, due to the high local pressure provided by the HSD.

In general the product distribution of hydrocarbons formed during the Fischer-Tropsch process follows an Anderson-Schulz-Flory distribution, which can be expressed as:

$$W_n/n = (1-\alpha)^2 \alpha^{n-1}. \quad (8)$$

where $W_n$ is the weight fraction of hydrocarbon molecules containing n carbon atoms, α is the chain growth probability or the probability that a molecule will continue reacting to form a longer chain. In general, alpha, α, is largely determined by the catalyst and the specific process conditions.

Examination of Eq. (8) reveals that methane will typically be the largest single product, however by having α approach one, the total amount of methane formed can be minimized compared to the sum of all of the various long-chained products. Increasing α increases the formation of long-chained hydrocarbons. The very long-chained hydrocarbons are waxes, which are solid at room temperature. Therefore, for production of liquid transportation fuels it may be necessary to crack some of the Fischer-Tropsch products, via downstream processing. In order to avoid this, zeolites or other catalyst substrates with fixed sized pores that can restrict the formation of hydrocarbons longer than some characteristic size (usually n<10) may be utilized.

Figure 8:
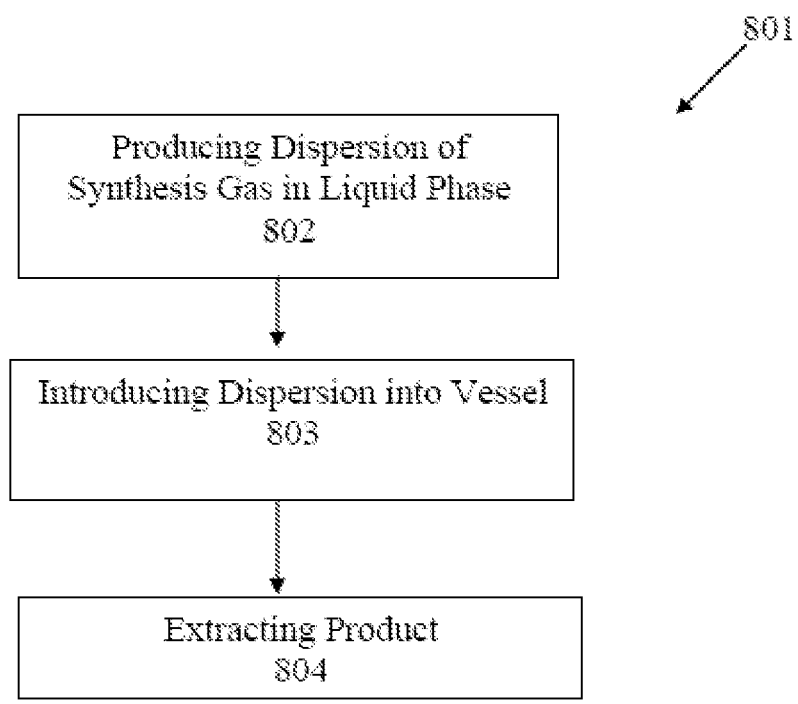
FIG. 8 is a schematic of a method of catalytically reacting synthesis gas to produce FT products according to an embodiment of this disclosure.

In embodiments, conventional FT is used to produce FT products from the synthesis gas produced in HSD 40. Alternatively, FIG. 8 is a schematic of a method of reacting synthesis gas from HSD 40 or obtained by any other means known in the art to produce products comprising hydrocarbons and/or alcohols 801 according to an embodiment of this disclosure. Reacting synthesis gas to produce products 801 comprises producing a dispersion of synthesis gas in a liquid phase 802, introducing the dispersion into a vessel 803, and extracting product 804.

Producing Dispersion of Synthesis Gas in Liquid Phase 802.

Reacting synthesis gas to produce products 801 may be used in conjunction with the method 300 of producing synthesis gas from carbonaceous slurry or may be a standalone method suitable to form product comprising one or more of liquid hydrocarbons and/or alcohols from synthesis gas (which may comprise other gaseous components, e.g. carbon dioxide, as discussed further hereinbelow) obtained by any means known in the art. Method 801 comprises producing a dispersion of synthesis gas in a liquid phase 802. Producing a dispersion of synthesis gas in liquid phase 802 may comprise introducing the product synthesis gas from HSD 40 and/or synthesis gas from another source/method into a HSD 40a. In embodiments, vessel 10 (or additional separation units downstream vessel 10) serves to separate product synthesis gas from liquid hydrocarbons produced in HSD 40, unreacted carbonaceous materials, and slurry liquid. In such embodiments a portion 22a of the synthesis gas removed from vessel 10 via first vessel—10 outlet line 16 can be combined with liquid carrier in line 21a and pumped via line 13a and pump 5a into (second) HSD 40a. In embodiments, product hydrocarbons from HSD 40 and synthesis gas produced in HSD 40 are removed together from vessel 10 via first vessel—10 outlet line 16. In such embodiments, the hydrocarbons produced in HSD 40 may serve as liquid carrier and little or no additional liquid carrier may be introduced via line 21a.

Producing dispersion of synthesis gas in liquid phase 802 comprises introducing product synthesis gas from HSD 40 and/or synthesis gas obtained via another method or source into HSD 40a along with liquid carrier. The liquid carrier and synthesis gas may be introduced separately to HSD 40a, or may be combined prior to introduction thereto (e.g. when removed from vessel 10 together). HSD 40a serves to produce a dispersion of synthesis gas in the liquid carrier, operating as discussed above with respect to operation of HSD 40, but at conditions suitable for conversion of synthesis gas rather than at conditions suitable for gasification of carbonaceous materials as in HSD 40. The high shear produced within HSD 40a results in dispersion of the synthesis gas (and optionally carbon dioxide) in micron or submicron-sized bubbles or droplets within a continuous liquid phase. The liquid phase may comprise liquid FT hydrocarbons, alcohols, or other suitable liquid carrier. In some embodiments, the resultant dispersion produced in HSD 40a has an average bubble size less than about 5, 4, 3, 2, 1.5, or 1 μm. Accordingly, the dispersion exiting HSD 40a via line 19a comprises micron and/or submicron-sized synthesis gas bubbles. In some embodiments, the mean bubble size is in the range of about 0.4 μm to about 1.5 μm. In some embodiments, the resultant dispersion has an average bubble or droplet size less than or about 1 μm. In some embodiments, the mean bubble size is less than about 400 nm, and may be less than or about 100 nm in some cases. In many embodiments, the microbubble dispersion is able to remain dispersed at atmospheric pressure for at least 15 minutes.

Introducing Dispersion into Vessel 803.

Reacting synthesis gas to produce product 801 may further comprise introducing the dispersion into a vessel 802. Once dispersed, the resulting dispersion exits HSD 40a via line 19a and may be introduced into a second vessel 10a, as illustrated in FIG. 5. As a result of the intimate mixing of the reactants prior to entering vessel 10a, a significant portion of the reactions may take place in HSD 40a. Catalyst, e.g. FT catalyst and/or catalyst designed to promote the production of alcohol, may be present within synthesis gas utilization apparatus 30. In embodiments, FT catalyst, as described above, may be coated onto portions of HSD 40a or may be introduced into HSD 40a with liquid carrier, e.g. via line 21a. Accordingly, in some embodiments, reactor/vessel 10a may be used primarily for heating and separation of products from unreacted synthesis gas. In embodiments, vessel 10a is absent. Alternatively, or additionally, vessel 10a may serve as a primary reaction vessel where most of the product is produced. Vessel/reactor 10a may be operated in either continuous or semi-continuous flow mode, or it may be operated in batch mode. The contents of vessel 10 may be maintained at a specified reaction temperature using heating and/or cooling capabilities (e.g., cooling coils) and temperature measurement instrumentation, employing techniques that are known to those of skill in the art. Pressure in the vessel may be monitored using suitable pressure measurement instrumentation, and the level of reactants in the vessel may be controlled using a level regulator, employing techniques that are known to those of skill in the art. Vessel 10a may be configured as a slurry bed reactor, a fluidized bed reactor, or a fixed bed reactor.

Extracting Product 804.

Reacting synthesis gas to produce product 801 may further comprise extracting product(s) 804. The reaction product(s) may be extracted directly from HSD 40a (e.g., when HSD 40a or liquid carrier 21a contains catalyst). Alternatively or additionally, product may be extracted from vessel 10a or a separation vessel downstream thereof. For example, unreacted synthesis gas (and lighter hydrocarbon products, such as, but not limited to, methane, alcohols and diesel) may be removed from vessel 10a via first vessel—10a outlet line 16a and liquid product may be removed from vessel 10a via second vessel—10a outlet line 17a. In embodiments, catalyst is circulated about production apparatus 30 (and HSD 40a), and catalyst may be separated from the product and recycled, for example, by introduction into liquid carrier line 21a or recycle directly into vessel 10a. The unreacted synthesis gas and other light gas extracted via first vessel—10a outlet line 16a may be recycled to HSD 40a, for example, via dispersible synthesis gas line 22a. Product exiting system 100 via line 19a or second vessel—10a outlet line 17a may be upgraded, sold, and or utilized as known in the art.

HSD 40a may be operated such that the reaction product extracted at 804 comprises alcohols and/or liquid hydrocarbons. In embodiments, the reaction product comprises substantially equal amounts of liquid hydrocarbons and alcohols. In such embodiments, product hydrocarbons and alcohols can be separated as known in the art. Conventional GTL typically produces significant amounts of water and relatively low amounts (e.g., 3-5%) of alcohol. In embodiments, product extracted (from HSD 40a and/or vessel 10a) comprises less water and/or more alcohols than conventional GTL product. The disclosed high shear synthesis gas utilization method may allow production of significant amounts of alcohol and low amounts (e.g., 3-5% or less than about 10%) of water.

In embodiments, synthesis gas from HSD 40 (produced from high shear gasification of carbonaceous material as described herein) and/or synthesis gas from another source/method is converted as described above to product comprising alcohols and hydrocarbons. In embodiments, the product from HSD 40a comprises hydrocarbons as a major component, alcohols as a secondary component, and water as a minor component. In embodiments, the product comprises greater than about 90% of components selected from alcohols and liquid hydrocarbons and less than about 10% water (for example, about 97% alcohols and/or hydrocarbons and about 3% water). Without wishing to be limited by theory, due to the conditions to which the gas is subjected within the HSD, significant amounts of alcohols may be produced in HSD 40a, with concomitant production of less water than conventional GTL. Carbon dioxide in the gas fed to HSD 40a may be converted to alcohols, rather than reacting with hydrogen to produce excess water. In this manner, value may be obtained from $CO_2$ in the feed synthesis gas. Thus, removal of carbon dioxide from synthesis gas prior to HSD 40a may thus be unnecessary and/or undesirable. In embodiments, available $CO_2$ may even be fed into the HSD 40a along with synthesis gas. Without wishing to be limited by theory, the extreme pressures/shear produced at the tips of the rotor/stator is believed to force the reaction away from the thermodynamically expected production of water toward the production of alcohols.

Conventional GTL processes typically produce a maximum of 27-28 moles of liquid product per 100 moles of gas fed. In embodiments, greater than 28 mole of liquid product comprising alcohols and/or liquid hydrocarbons is produced by high shear utilization of synthesis gas (and optionally carbon dioxide) as disclosed herein.

Liquid hydrocarbons and/or alcohols removed from vessel 10 may be combined with liquid product comprising liquid hydrocarbons and/or alcohols in line 17. A portion of the product in line 17a may be separated and utilized as liquid carrier upon recycle to HSD 40a via line 21a. Line 21a may thus contain a flowing fresh carrier stream and/or a recycle stream from vessel 10a. As mentioned above with respect to conventional FT hydrocarbon production, the product distribution will be dependent on operating conditions, any catalyst utilized, and feed gas (synthesis gas and/or carbon dioxide) composition. In embodiments, the product comprises hydrocarbons having primarily C5+ hydrocarbon products (i.e., hydrocarbons having five or more carbons).

Catalyst (e.g., FT catalyst and/or catalyst designed to promote production of alcohols from synthesis gas comprising carbon dioxide) may be introduced directly into vessel 10*a*, as a hydrocarbon slurry or stream. Alternatively, or additionally, catalyst may be added elsewhere in system 100. For example, catalyst slurry may be injected into line 21*a*.

Commonly known FT operating conditions may be utilized in HSD 40*a* and vessel 10*a*. Alternatively, less severe operating conditions (i.e. lower temperature and/or pressure) may be utilized in product production apparatus 30.

Multiple Pass Operation.

In the embodiment shown in FIG. 5, the system is configured for single pass operation. The output of HSD 40 may be run through a subsequent HSD. In some embodiments, it may be desirable to pass the contents of flow line 19, or a fraction thereof, through HSD 40 during a second pass. In this case, at least a portion of the contents of flow line 19 may be recycled from flow line 19 and pumped by pump 5 into line 13 and thence into HSD 40. Additional reactants may be injected via line 22 into line 13, or may be added directly into the HSD. In other embodiments, product is further treated prior to recycle of a portion thereof to HSD 40. Similarly, where suitable, multiple pass operation may be utilized for stand-alone or integrated HSD 40*a* (i.e., whether HSD 40*a* is utilized along with HSD 40 or for conversion of gas obtained by means other than high shear gasification of carbonaceous materials via HSD 40).

Multiple HSDs.

In some embodiments, two or more HSDs like HSD 40, or configured differently, are aligned in series, and are used to promote further reaction. Operation of the mixers may be in either batch or continuous mode. In some instances in which a single pass or "once through" process is desired, the use of multiple HSDs in series may also be advantageous. In embodiments, the reactants pass through multiple HSDs 40 in serial or parallel flow. For example, in embodiments, product in outlet line 19 is fed into a second HSD. When multiple HSDs 40 are operated in series, additional reactants (liquid, gaseous or solid) may be injected into the inlet feedstream of each HSD. For example, additional dispersible gas or vapor, such as hydrogen, oxygen, air, associated gas or steam may be introduced into a second or subsequent HSD 40. In some embodiments, multiple HSDs 40 are operated in parallel, and the outlet products therefrom are introduced into one or more flow lines 19. Similarly, multiple HSDs 40*a* may be utilized, where suitable, and additional reactants (e.g., synthesis gas and/or carbon dioxide) or carrier may be introduced, as desired, into additional HSDs 40*a*.

Features.

The rate of chemical reactions involving liquids, gases and solids depend on time of contact, temperature, and pressure. In cases where it is desirable to react two or more raw materials of different phases (e.g. solid and liquid; liquid and gas; solid, liquid and gas; solid and gas), one of the limiting factors controlling the rate of reaction involves the contact time of the reactants. When reaction rates are accelerated, residence times may be decreased, thereby increasing obtainable throughput.

In the case of heterogeneously catalyzed reactions there is the additional rate limiting factor of having the reacted products removed from the surface of the solid catalyst to permit the catalyst to catalyze further reactants. Contact time for the reactants and/or catalyst is often controlled by mixing which provides contact with reactants involved in a chemical reaction. The use of the disclosed HSD(s) may increase rates of reaction relative to conventional systems and methods. For example, gasification of carbonaceous material and/or the rate of FT reaction may be increased via the disclosed system and method.

Not to be limited by theory, it is known in emulsion chemistry that sub-micron particles, or bubbles, dispersed in a liquid undergo movement primarily through Brownian motion effects. Such sub-micron sized particles or bubbles may have greater mobility through boundary layers of solid catalyst particles, thereby facilitating and accelerating the catalytic reaction through enhanced transport of reactants.

The intimate contacting of reactants provided by the HSDs may result in faster and/or more complete reaction of reactants [e.g., $CH_x$ and $H_2O$ via Eqs. (3)/(5) and/or the reaction of CO and $H_2$ according to Eq. (7)]. In embodiments, use of the disclosed process comprising reactant mixing via external HSD allows use of reduced quantities of catalyst (e.g. FT catalyst) than conventional configurations and methods and/or increases the product yield and/or the conversion of reactants (e.g. carbon in the carbonaceous material of the slurry in HSD 40 and synthesis gas within HSD 40*a*). In embodiments, the method comprises incorporating an external HSD into an established process thereby reducing the amount of catalyst required to effect desired reaction and/or enabling an increase in production throughput from a process operated without a HSD. For example, incorporation of one or more HSDs 40 into an existing FT production plant may reduce costs and/or increase production of liquid hydrocarbon products by allowing more economical production of synthesis gas having a desired composition. The incorporation of a HSD for production of synthesis gas may reduce the amount of processing of the synthesis gas required upstream of a conventional FT reactor (e.g., reduce or eliminate the need for removal of $CO_2$ from the synthesis gas prior to FT). In embodiments, the disclosed method reduces operating costs and/or increases production from an existing process. Alternatively, the disclosed method may reduce capital costs for the design of new processes.

Without wishing to be limited to a particular theory, it is believed that the HSD of certain embodiments of the present system and methods may induce cavitation whereby one or more reactant is dissociated into free radicals, which then react. In embodiments, the extreme pressure at the tips of the rotors/stators leads to liquid phase reaction, and no cavitation is involved.

Use of Multifunctional Catalysts.

In some embodiments, multifunctional catalyst is used in the processes described herein. In an embodiment, the multifunctional catalyst is able to promote both dehydrogenation reactions and alcohol forming (AF) reactions. In another embodiment, the multifunctional catalyst is capable of promoting both FT reactions and alcohol forming (AF) reactions. In some embodiments, the multifunctional catalyst is a blend of dehydrogenation catalyst and AF catalyst. In some other embodiments, the multifunctional catalyst is a blend of FT catalyst and AF catalyst. Catalysts for dehydrogenation reactions, FT reactions, and alcohol forming (AF) reactions are disclosed herein and are also known in the art. The disclosures of U.S. Patent Application Pub. No. 2008/0281136 (U.S. patent application Ser. No. 12/109,587, now U.S. Pat. No. 8,129,305) and U.S. Pat. Nos. 5,659,090 and 4,551,444 are hereby incorporated herein by reference for further details concerning dehydrogenation catalysts, FT catalysts, and AF catalysts.

Depending on the feedstock and desired end products, various multifunctional catalysts may be used. Such catalysts are capable of promoting catalytic processes such as dehydrogenation, water dissociation, carbon dioxide dissociation, syngas reforming, and alcohol synthesis. For example, a multifunctional catalyst is used in a FT process, wherein said catalyst promotes dissociation/oxidation of a fuel to produce syngas and also syngas reforming reactions. In some cases, such multifunctional catalyst is a blend formed by intimate mixing of several suitable and compatible catalysts. In some other cases, such multifunctional catalyst is a mixture, comprising separate catalyst particles. Combinations of inorganic and organic catalysts (including biocatalysts) can also be used.

In some embodiments, the use of multifunctional catalyst for FT reactions and AF reactions reduces the production of unwanted by-products (e.g., water, carbon monoxide, carbon dioxide). In some embodiments, the use of multifunctional catalyst for FT reactions and AF reactions enhances the production of C2+ hydrocarbons and oxygenates (e.g., alcohols). In some embodiments, the use of multifunctional catalyst for dehydrogenation reactions and AF reactions reduces the production of unwanted by-products (e.g., water, carbon monoxide, carbon dioxide). In some embodiments, the use of multifunctional catalyst for dehydrogenation reactions and AF reactions enhances the production of C2+ hydrocarbons and oxygenates (e.g., alcohols).

In an embodiment, a multifunctional catalyst is utilized, wherein said multifunction catalyst is capable of (1) splitting methane (dehydrogenating or partially oxidizing methane); (2) syngas reforming; (3) alcohol synthesis; and (4) dissociating water and/or carbon dioxide. In some cases, such multifunctional catalyst is a blend formed by intimate mixing of several suitable and compatible catalysts. In some other cases, such multifunctional catalyst is a mixture, comprising separate catalyst particles. Multiple HSD's may be utilized in series to perform different reactions. Some HSD's use suitable catalysts; some HSD's do not need the presence of catalysts. In the reactions that involve carbon dioxide, in some cases, carbon dioxide is dissolved in water to become carbonic acid ($H_2CO_3$) before dissociation.

In some embodiments, the multifunctional catalyst is applied in a fixed bed reactor. For example, the fixed bed reactor is downstream of the HSD. After the reactants are intimately mixed in the HSD, the reactant mixture is introduced into the fixed bed reactor comprising the multifunctional catalyst and reactions are allowed to propagate in the fixed bed reactor. In some other embodiments, the multifunctional catalyst is applied as a slurry. For example, multifunctional catalyst slurry and reactants may be mixed in the HSD and then the reactant mixture with the catalyst slurry is introduced into a suitable vessel. Reactions may take place in both the HSD and the vessel. In some further embodiments, the multifunctional catalyst is applied by being constructed as a catalytic surface in the HSD. For example, reactants are introduced into a HSD comprising a catalytic surface containing multifunctional catalyst. Reactions are initiated in the HSD and allowed to propagate in a suitable vessel fluidly connected to the HSD downstream.

In some embodiments, additional carbon dioxide and/or water is needed in the processes utilizing multifunctional catalysts so that desired products are obtained. For example, when multiple HSD's are used (in parallel or in series), carbon dioxide and/or water may be added inter-stage where necessary. It is contemplated that one of ordinary skill in the art, provided this disclosure, is able to make such judgments as to where additional reactants (e.g., carbon dioxide and/or water) are needed.

EXAMPLES

Various dimensions, sizes, quantities, volumes, rates, and other numerical parameters and numbers have been used for purposes of illustration and exemplification of the principles of the invention, and are not intended to limit the invention to the numerical parameters and numbers illustrated, described or otherwise stated herein. Likewise, unless specifically stated, the order of steps is not considered critical. The different teachings of the embodiments discussed below may be employed separately or in any suitable combination to produce desired results.

Example 1

High Shear Reaction of 2:1 Methane:Carbon Dioxide with Ruthenium Carbonyl

A cold trap was positioned within system 100 as shown in FIG. 1. Five (5) grams of triruthenium carbonyl was dissolved at 125° C. in ½ L of PEG. This ruthenium carbonyl/PEG was added to 1 L PEG. Three hours after initiation of the test, ruthenium carbonyl/PEG solution was injected into vessel 10 for a period of one hour.

Liquid product MBM-33-B (Liquid) was recovered from cold trap liquid 24 and analyzed for glycols. The results are presented in Table 2.

TABLE 2

| Test Method | Component | Amount, mg/L |
|---|---|---|
| SW-846 8015D Non Purgeable Organic Compounds | Ethanol | 484 |
| | Methanol | 4637 |
| | n-Propyl Alcohol | 44.7 |
| | t-Butyl Alcohol | 7.08 |
| SW-846 8015M Glycols | Ethylene Glycol | 27264 |
| | Diethylene Glycol | 68170 |
| | Triethylene Glycol | 123207 |
| | Tetraethylene glycol | 142359 |
| | 1,2,4-Trimethylbenzene | 0.826 |
| | 1,3,5-Trimethylbenzene | 0.574 |
| SW-846 8260B Volatile Organic Compounds | Ethylbenzene | 0.193 |
| | m- & p-Xylenes | 1.04 |
| | MEK | 18.6 |
| | Naphthalene | 0.601 |
| | n-Butylbenzene | 0.143 |
| | o-Xylene | 0.570 |
| | Xylenes | 1.61 |
| TX 1005 Total Petroleum Hydrocarbons | $C_6$-$C_{12}$ | 407 |
| | >C12-C28 | 343 |
| | >C28-C35 | BRL* |
| | Total C6-C35 | 750 |
| TX 1006 Total Petroleum Hydrocarbons | Aliphatic (>C06-C08) | BRL |
| | Aliphatic (>C08-C10) | BRL |
| | Aliphatic (>C10-C12) | BRL |
| | Aliphatic (>C12-C16) | 139.656 |
| | Aliphatic (>C16-C21) | 53.404 |
| | Aliphatic (>C21-C35) | BRL |
| | Aromatic (C06-C08) | BRL |
| | Aromatic (C08-C10) | 478.062 |
| | Aromatic (C10-C12) | 54.089 |
| | Aromatic (C12-C16) | 50.074 |
| | Aromatic (C16-C21) | 61.368 |
| | Aromatic (C21-C35) | BRL |

*BRL: Below Recordable Limits

Example 2

High Shear Reaction of 2:1 Methane:Carbon Dioxide with Ruthenium Carbonyl

Sample MBM 34-2 was taken from cold trap gas 25, sample 34-1 from vessel 10 product liquid 16, and sample 34-PEG was a sample of virgin polyethylene glycol. The results were analyzed for hydrocarbons and glycols, and the results are presented in Table 3.

TABLE 3

MBM 34-1, MBM 34-2, and MBM 34 PEG

| Test Method | Component | MBM 34-1 Reactor Liquid | MBM 34-2 Cold Trap Gas | MBM 34-PEG Virgin PEG |
|---|---|---|---|---|
| EPA TO-15 Volatile Organic Compounds in Air by GCMS, nL | Benzene | — | 2.72 | — |
| | Toluene | — | 3.51 | — |
| | Ethylbenzene | — | 7.55 | — |
| | m- & p-Xylenes | — | 8.81 | — |
| | Styrene | — | 1.09 | — |
| | o-Xylene | — | 9.17 | — |
| | 1,3,5-Trimethylbenzene | — | 2.68 | — |
| | 1,2,4-Trimethylbenzene | — | 5.74 | — |
| SW-846 8015D Non Purgeable Organic Compounds, mg/kg | Ethanol | BRL* | — | BRL |
| | Methanol | BRL | — | BRL |
| | n-Propyl Alcohol | BRL | — | BRL |
| | t-Butyl Alcohol | BRL | — | BRL |
| SW-846 8015M Glycols, mg/kg | Ethylene Glycol | 2780 | — | BRL |
| | Diethylene Glycol | 27216 | — | 27353 |
| | Triethylene Glycol | 152328 | — | 165424 |
| | Tetraethylene glycol | 402944 | — | 430688 |
| | 1,2,4-Trimethylbenzene | 0.460 | — | 0.163 |
| | 1,3,5-Trimethylbenzene | 0.128 | — | 0.097 |
| | Ethylbenzene | 0.139 | — | 0.329 |
| SW-846 8260B Volatile Organic Compounds, mg/kg | m- & p-Xylenes | 0.574 | — | 0.509 |
| | MEK | 0.210 | — | 0.490 |
| | Naphthalene | BRL | — | BRL |
| | n-Butylbenzene | BRL | — | BRL |
| | n-Propylbenzene | — | — | 0.059 |
| | o-Xylene | 0.249 | — | 0.097 |
| | Xylenes | — | — | — |
| | Toluene | 0.131 | — | 0.701 |
| TX 1005 Total Petroleum Hydrocarbons, mg/kg | $C_6$-$C_{12}$ | 1457 | — | 497 |
| | >C12-C28 | 3531 | — | 1950 |
| | >C28-C35 | BRL | — | BRL |
| | Total C6-C35 | 4988 | — | 2447 |
| TX 1006 Total Petroleum Hydrocarbons, mg/kg | Aliphatic (>C12-C16) | BRL | — | BRL |
| | Aliphatic (>C16-C21) | BRL | — | BRL |
| | Aromatic (C8-C10) | 342.049 | — | 339.020 |
| | Aromatic (C10-C12) | 1569.564 | — | 1229.302 |
| | Aromatic (C12-C16) | 994.041 | — | 866.937 |
| | Aromatic (C16-C21) | 1566.368 | — | BRL |

*BRL: Below Recordable Limits

Samples MBM-34D and MBM-34F were taken from the cold trap liquid 24, as described in Appendix A attached herewith. The results of the analysis thereof are presented in Table 4.

TABLE 4

MBM 34-1, MBM 34-2, and MBM 34

| Test Method | Component | MBM 34-D Cold Trap | MBM 34-F Cold Trap |
|---|---|---|---|
| SW-846 8015D Non Purgeable Organic Compounds, mg/L | Ethanol | 146 | 125 |
| | Methanol | 2020 | 2884 |
| | n-Propyl Alcohol | 13.9 | 20.9 |
| | t-Butyl Alcohol | BRL* | BRL |
| SW-846 8015M Glycols, mg/L | Ethylene Glycol | 11363 | 13147 |
| | Diethylene Glycol | 34752 | 31944 |
| | Triethylene Glycol | 51417 | 54701 |
| | Tetraethylene glycol | 64274 | 104596 |
| | 1,2,4-Trimethylbenzene | 0.258 | BRL |
| | 1,3,5-Trimethylbenzene | BRL | BRL |
| | Ethylbenzene | BRL | BRL |
| SW-846 8260B Volatile Organic Compounds, mg/L | m- & p-Xylenes | 0.260 | BRL |
| | MEK | 11.6 | 4.29 |
| | Naphthalene | 0.156 | BRL |
| | n-Butylbenzene | BRL | BRL |
| | n-Propylbenzene | BRL | BRL |
| | o-Xylene | 0.142 | BRL |
| | Xylenes | 0.402 | BRL |
| | Toluene | BRL | BRL |
| TX 1005 Total Petroleum Hydrocarbons, mg/L | $C_6$-$C_{12}$ | 231 | 354 |
| | >C12-C28 | 116 | 3156 |
| | >C28-C35 | BRL | BRL |
| | Total C6-C35 | 347.583 | 3510 |
| TX 1006 Total Petroleum Hydrocarbons, mg/L | Aliphatic (>C6-C8) | BRL | BRL |
| | Aliphatic (>C8-C10) | BRL | BRL |
| | Aliphatic (>C10-C12) | BRL | BRL |
| | Aliphatic (>C12-C16) | 54.754 | 1447.8 |
| | Aliphatic (>C16-C21) | 36.737 | 774.1 |
| | Aliphatic (>C21-C35) | BRL | 533.8 |
| | Aromatic (C6-C8) | BRL | BRL |
| | Aromatic (C8-C10) | 112.049 | BRL |
| | Aromatic (C10-C12) | 37.385 | BRL |

TABLE 4-continued

MBM 34-1, MBM 34-2, and MBM 34

| Test Method | Component | MBM 34-D Cold Trap | MBM 34-F Cold Trap |
|---|---|---|---|
| | Aromatic (C12-C16) | 35.599 | 251.4 |
| | Aromatic (C16-C21) | 47.699 | 403.0 |
| | Aromatic (C21-C35) | BRL | BRL |

*BRL: Below Recordable Limits

Example 4

High Shear Reaction of 2:1 Methane:Carbon Dioxide and Methane Alone in Paraffinic Oil with Palladium Silica Catalyst Samples MBM-35B Water and 35-TagA Water were taken from the cold trap 24 as indicated in Appendix A hereinbelow. The results of the analysis thereof are presented in Table 5.

TABLE 5

MBM 35-B Water and MBM 35-TagA Water

| Test Method | Component | MBM 35-B Cold Cold Trap Liquid | MBM 35-TagA Cold Trap Liquid |
|---|---|---|---|
| SW-846 8015D Non-Purgeable Organic Compounds, mg/L | 2-Propanol | BRL* | BRL |
| | Ethanol | 2648 | 2036 |
| | Isobutyl Alcohol | 66.9 | 41.4 |
| | Methanol | 1147 | 1602 |
| | n-Butanol | 881 | 828 |
| | n-Propyl Alcohol | 1488 | 1180 |
| | sec-Butyl Alcohol | 474 | 447 |
| | t-Butyl Alcohol | 58.4 | 72.5 |
| SW-846 8015M Glycols, mg/L | Ethylene Glycol | 2761 | 2846 |
| | Diethylene Glycol | 2842 | 4747 |
| | Triethylene Glycol | 2568 | 4367 |
| | Tetraethylene glycol | 774 | 1644 |
| | 1,2,4-Trimethylbenzene | BRL | BRL |
| | 1,3,5-Trimethylbenzene | BRL | BRL |
| | Ethylbenzene | BRL | BRL |
| SW-846 8260B Volatile Organic Compounds, mg/L | m- & p-Xylenes | BRL | BRL |
| | MEK | 386 | 783 |
| | Naphthalene | BRL | BRL |
| | n-Butylbenzene | BRL | BRL |
| | n-Propylbenzene | BRL | BRL |
| | o-Xylene | BRL | BRL |
| | Xylenes | BRL | BRL |
| | Toluene | BRL | BRL |
| TX 1005 Total Petroleum Hydrocarbons, mg/L | $C_6$-$C_{12}$ | 1556 | 1255 |
| | >C12-C28 | 3655 | 2460 |
| | >C28-C35 | 931 | 1418 |
| | Total C6-C35 | 6142 | 5133 |
| TX 1006 Total Petroleum Hydrocarbons, mg/L | Aliphatic (>C6-C8) | BRL | BRL |
| | Aliphatic (>C8-C10) | 38.4 | 61.7 |
| | Aliphatic (>C10-C12) | 92.2 | 121.7 |
| | Aliphatic (>C12-C16) | 549.3 | 387.7 |
| | Aliphatic (>C16-C21) | 733.7 | 561.9 |
| | Aliphatic (>C21-C35) | 3281.5 | 3759.2 |
| | Aromatic (C6-C8) | 456.5 | 414.8 |
| | Aromatic (C8-C10) | 617.1 | 321 |
| | Aromatic (C10-C12) | 690.8 | 248 |
| | Aromatic (C12-C16) | 701.4 | 118.6 |
| | Aromatic (C16-C21) | 162.5 | BRL |
| | Aromatic (C21-C35) | 87.7 | BRL |

*BRL: Below Recordable Limits

Samples MBM-35B Oil and MBM-35TagA Oil both were taken from vessel 10 liquid. The results of the analysis thereof are presented in Table 6.

TABLE 6

MBM 35-B Oil and MBM 35-TagA Oil

| Test Method | Component | MBM 35-B Oil-Vessel 10 Liquid | MBM 35-TagA Oil Vessel 10 Liquid |
|---|---|---|---|
| SW-846 8015D Non-Purgeable Organic Compounds, mg/kg | 2-Propanol | BRL* | BRL |
| | Ethanol | 450 | 202 |
| | Isobutyl Alcohol | 71.8 | 38.9 |
| | Methanol | 132 | 173 |
| | n-Butanol | 1611 | 818 |
| | n-Propyl Alcohol | 867 | 378 |
| | sec-Butyl Alcohol | 361 | 174 |
| | t-Butyl Alcohol | BRL | BRL |
| SW-846 8015M Glycols, mg/kg | Ethylene Glycol | BRL | BRL |
| | Diethylene Glycol | BRL | BRL |
| | Triethylene Glycol | BRL | BRL |
| | Tetraethylene glycol | BRL | BRL |
| | 1,2,4-Trimethylbenzene | BRL | BRL |
| | 1,3,5-Trimethylbenzene | BRL | BRL |
| | Ethylbenzene | BRL | BRL |
| SW-846 8260B Volatile Organic Compounds, mg/kg | m- & p-Xylenes | BRL | BRL |
| | MEK | 462 | 545 |
| | Naphthalene | BRL | BRL |
| | n-Butylbenzene | BRL | BRL |
| | n-Propylbenzene | BRL | BRL |
| | o-Xylene | BRL | BRL |
| | Xylenes | BRL | BRL |
| | Toluene | BRL | BRL |
| TX 1005 Total Petroleum Hydrocarbons, mg/kg | $C_6$-$C_{12}$ | 160598 | 19135 |
| | >C12-C28 | 534858 | 60488 |
| | >C28-C35 | 128928 | 47059 |
| | Total C6-C35 | 824384 | 126682 |
| TX 1006 Total Petroleum Hydrocarbons, mg/kg | Aliphatic (>C6-C8) | BRL | BRL |
| | Aliphatic (>C8-C10) | 14144 | BRL |
| | Aliphatic (>C10-C12) | 24985 | 3160.8 |
| | Aliphatic (>C12-C16) | 78792 | 8115.5 |
| | Aliphatic (>C16-C21) | 100170 | 11078.6 |
| | Aliphatic (>C21-C35) | 484242 | 78233.2 |
| | Aromatic (C06-C08) | 15842 | 10369.9 |
| | Aromatic (C08-C10) | 55048 | 11291.5 |
| | Aromatic (C10-C12) | 67800 | 8445.2 |
| | Aromatic (C12-C16) | 73365 | 6187.8 |
| | Aromatic (C16-C21) | 25389 | 3866.2 |
| | Aromatic (C21-C35) | BRL | BRL |

*BRL: Below Recordable Limits

Example 5

High Shear Ethane Conversion

For this example, the same equipment configuration as used in examples 2-4 was utilized. The agitator on vessel 10 was operated at 1000 RPM. The High Shear unit 40 was operated at 13,500 RPM. The vessel 10 was held at 150° C. and 345 kPa (50 psi).

Six liters of melted polyethylene glycol having a number average molecular weight, $M_n$, of 850-950 (Sigma Aldrich) was placed in vessel 10 along with 2 kilograms of Palladium Catalyst (0.5 wt. % Pd on $SiO_2$) and 5 grams of Triruthenium Dodecacarbonyl (Sigma Aldrich). All 3 heaters (H1, H2, H3), gear pump 5 and HSD 40 were turned on.

System 100 was closed and purged with $CO_2$ three times and the gas compressor (extracting gas from the top of vessel 10 to inlet line 22 of HSD 40) was turned on. Gas feed comprising ethane and $CO_2$ at an approximate flow ratio of 2:1 was introduced into top of vessel 10. Similar runs were conducted with and without injection of 1 L of water into vessel 10. After 12 hours, the experiment was terminated and samples were taken from cold trap 30 and analyzed.

Results are presented in Table 7, MBM 39-A results are without water injection, and MBM 39-AW are with water injection.

TABLE 7

MBM 39-A and MBM 39-AW Cold Trap Liquid

| Test Method | Component | MBM 39-A | MBM 39-AW |
|---|---|---|---|
| SW-846 8015D Non-Purgeable Organic Compounds, mg/L | 2-Propanol | BRL* | BRL |
| | Ethanol | 3876 | 77.9 |
| | Isobutyl Alcohol | BRL | BRL |
| | Methanol | 3938 | 180 |
| | n-Butanol | BRL | BRL |
| | n-Propyl Alcohol | 339 | BRL |
| | sec-Butyl Alcohol | BRL | BRL |
| | t-Butyl Alcohol | 44.4 | BRL |
| SW-846 8015M Glycols, mg/L | Ethylene Glycol | 2142 | 156 |
| | Diethylene Glycol | 2785 | 94.2 |
| | Triethylene Glycol | 284 | BRL |
| | Tetraethylene glycol | 707 | BRL |
| SW-846 8260B Volatile Organic Compounds, mg/L | MEK | 176 | 4.47 |
| TX 1005 Total Petroleum Hydrocarbons, mg/L | $C_6$-$C_{12}$ | BRL | 70.1 |
| | >C12-C28 | 14609 | 1031 |
| | >C28-C35 | BRL | BRL |
| | Total C6-C35 | 14609 | 1101.1 |

*BRL: Below Recordable Limits

Example 6

High Shear Propane Conversion

A run with conditions and equipment similar to Example 5 was conducted with propane gas substituted for ethane. Similar runs were conducted with and without injection of 1 L of water into vessel 10. After 12 hours, the experiment was terminated and samples were taken from cold trap 30 and analyzed. Results are presented in Table 8, MBM 39-B results are without water injection, and MBM 39-BW are with water injection.

TABLE 8

MBM 39-B and MBM 39-BW Cold Trap Liquid

| Test Method | Component | MBM 39-B | MBM 39-BW |
|---|---|---|---|
| SW-846 8015D Non-Purgeable Organic Compounds, mg/L | 2-Propanol | BRL* | BRL |
| | Ethanol | 569 | 47.1 |
| | Isobutyl Alcohol | BRL | BRL |
| | Methanol | 5949 | 482 |
| | n-Butanol | BRL | BRL |
| | n-Propyl Alcohol | 96.5 | BRL |
| | sec-Butyl Alcohol | BRL | BRL |
| | t-Butyl Alcohol | BRL | BRL |
| SW-846 8015M Glycols, mg/L | Ethylene Glycol | 15229 | 1282 |
| | Diethylene Glycol | 22270 | 2937 |
| | Triethylene Glycol | 7112 | 2679 |
| | Tetraethylene glycol | 5137 | 1648 |
| | 1,2,4-Trimethylbenzene | 1.38 | BRL |
| SW-846 8260B Volatile Organic Compounds, mg/L | m- & p-Xylenes | 0.606 | BRL |
| | MEK | 19.9 | 53.6 |
| | Methyl Acetate | 3.408 | BRL |
| | Naphthalene | 1.79 | BRL |
| | o-Xylene | 0.527 | BRL |
| | Xylenes | 1.133 | BRL |
| TX 1005 Total Petroleum Hydrocarbons, mg/L | $C_6$-$C_{12}$ | BRL | BRL |
| | >C12-C28 | 22915 | 2351 |
| | >C28-C35 | BRL | BRL |
| | Total C6-C35 | 22915 | 2351 |

*BRL: Below Recordable Limits

Example 7

High Shear Butane Conversion

A run with conditions and equipment similar to Example 5 was conducted with butane gas substituted for ethane. During this run, 1 L of water was injected into vessel 10 to assist in steam stripping of organics present. The analytical results are presented in Table 9.

TABLE 9

MBM 39-CW Cold Trap Liquid

| Test Method | Component | MBM 39-CW |
|---|---|---|
| SW-846 8015D Non-Purgeable Organic Compounds, mg/L | 2-Propanol | BRL* |
| | Ethanol | 117 |
| | Isobutyl Alcohol | BRL |
| | Methanol | 276 |
| | n-Butanol | BRL |
| | n-Propyl Alcohol | 24.0 |
| | sec-Butyl Alcohol | BRL |
| | t-Butyl Alcohol | BRL |
| SW-846 8015M Glycols, mg/L | Ethylene Glycol | BRL |
| | Diethylene Glycol | BRL |
| | Triethylene Glycol | BRL |
| | Tetraethylene glycol | BRL |
| | Ethyl Acetate | 18 |
| | Ethylbenzene | 0.462 |
| | MEK | 23.9 |
| SW-846 8260B Volatile Organic Compounds, mg/L | Methyl Acetate | 18.25 |
| | n-Butylbenzene | 0.462 |
| | n-Propylbenzene | 0.343 |
| | o-Xylene | 0.331 |
| | Toluene | 0.755 |
| | Xylenes | 0.331 |
| TX 1005 Total Petroleum Hydrocarbons, mg/L | $C_6$-$C_{12}$ | BRL |
| | >C12-C28 | 3525 |
| | >C28-C35 | BRL |
| | Total C6-C35 | 3525 |

*BRL: Below Recordable Limits

Example 8

Reaction of Carbon Monoxide and Hydrogen Via High Shear Mixing

The following example demonstrates the ability of the high shear device to facilitate the reaction between carbon monoxide and hydrogen in a synthesis gas conversion operation similar to what is commonly known as the Fischer Tropsch reaction where higher molecular weight hydrocarbons are synthesized.

Figure 4:
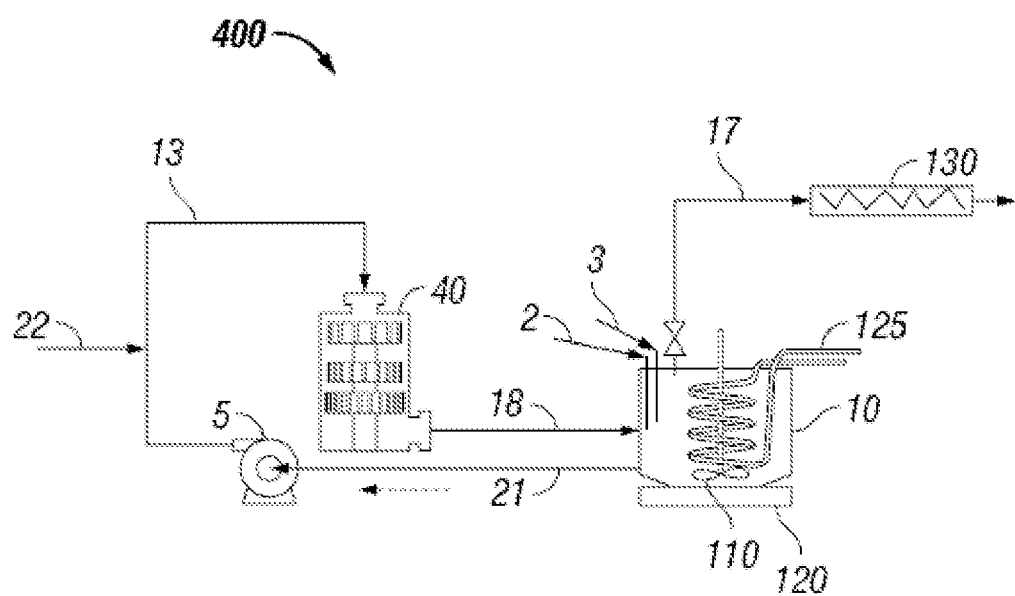
FIG. 4 is a process flow diagram of the apparatus used for the reaction of CO and $H_2$ in the experiment of Example 8.

An external IKA MK 2000 mill 40 (Registered trademark of IKA Works, Inc Wilmington, N.C.) was connected to a 10 liter stirred reactor. The apparatus used for the high shear process 400 for the reaction of CO and $H_2$ in this example is shown schematically in FIG. 4.

The ten liter reactor 10 was formed by welding a section of ten inch diameter stainless steel pipe with a base plate and a head plate equipped with an agitator shaft and seal. Reactor 10 comprised internal paddle agitator 110 and a cooling coil 125. Reactor 10 also comprised pressure relief valve 17, discharge line 21, temperature probe 2 and pressure gauge 3. Heating mantle 120 was used to heat reactor 10 during start-up.

Reactor 10 was charged with eight liters of methanol (anhydrous, 99.8%) used as the carrier fluid and 5 grams of Triruthenium dodecacarbonyl (99%) catalyst, both supplied by Sigma-Aldrich Corporation, St. Louis, Mo.

Reactor 10 was sealed and purged with hydrogen. Circulation of catalyst slurry was initiated with heating. The recirculating pump 5 was a Roper Type 1 gear pump, Roper Pump Company (Commerce Ga.).

Dispersible gas stream comprising a mixed gas stream having an $H_2$:CO mole ratio of 2 was fed via dispersible inlet line 22 into the inlet of the IKA unit 40 at ambient temperature, and gas flow was regulated by means of a pressure relief valve (not shown) between the supply manifold (not shown) and the reactor IKA unit 40. The reaction was then carried out, maintaining the flow of mixed gases into the reactor. Pressures and temperatures are tabulated in Table 10.

TABLE 10

Pressures and Temperatures for Example 8

| Time (min) | Pump 5 pressure (psig) | Pump 5 pressure kPa | Reactor 10 Pressure (psig) | Reactor 10 Pressure kPa | Temperature (° C.) | Mixed Gas Flow (cc/min) |
|---|---|---|---|---|---|---|
| 0 | 80 | 552 | 23 | 159 | 61 | 50 |
| 60 | 122 | 841 | 70 | 531 | 77 | 81 |
| 120 | 162 | 1117 | 115 | 538 | 78 | 183 |
| 180 | 193 | 1331 | 154 | 545 | 79 | 200 |

Excess volatiles were vented through reactor 10 via condenser 130 which was cooled by water. Reactor 10 vent gas line 17 was used to vent excess hydrogen, CO and volatile reaction products. High shear device 40 was set to 60 Hz. After 180 min the mixed gas flow in line 22 was terminated, the pressure of reactor 10 was reduced, and high shear system 400 was allowed to cool to room temperature. A sample was drawn from reactor 10 and analyzed using gas chromatography. The results of the analysis are presented as Table 11.

TABLE 11

Gas Chromatograph Results from Example 8

| Component | Weight % |
|---|---|
| Methanol | 90.83 |
| n-hexane* | 4.63 |
| 3-Methylpentane | 1.64 |
| 2,4-Dimethylpentane | 0.85 |
| 2-Methylpentane | 0.66 |
| C 22 | 0.20 |
| msc | 1.19 |
| Total | 100.00 |

*Used as a rinsing agent

The results indicate that the system produced several higher molecular weight ($C5^+$) hydrocarbon reaction products.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The disclosures of all patents, patent applications, and publications cited herein are hereby incorporated by reference, to the extent they provide exemplary, procedural or other details supplementary to those set forth herein.

What is claimed is:

1. A system for producing an organic, the system comprising:
    at least one external high shear mixing device comprising at least one rotor and at least one stator separated by a shear gap, wherein the shear gap is the minimum distance between the at least one rotor and the at least one stator, wherein the at least one rotor is configured to provide a tip speed of at least about 5 m/sec, wherein the tip speed is defined as $\pi Dn$, where D is the diameter of the at least one rotor and n is the frequency of revolution;
    a pump configured for delivering a fluid stream comprising a mixture of a liquid medium and a light gas to the at least one high shear mixing device, wherein the at least one high shear mixing device is configured to form a dispersion of the light gas in the liquid medium, wherein the dispersion comprises light gas bubbles having an average bubble diameter on the submicron or nanometer scale; and
    a reactor containing a multifunctional catalyst, and comprising at least one inlet and at least one outlet, wherein the at least one inlet of the reactor is fluidly connected to the at least one high shear mixing device, and wherein the at least one outlet of the reactor is configured for extracting the organic therefrom, and wherein the multifunctional catalyst promotes at least two of the following reactions: dehydrogenation, water dissociation, carbon dioxide dissociation, and Fischer-Tropsch synthesis;
    wherein the light gas comprises synthesis gas, and wherein the system further comprises at least one second high shear device configured for the gasification of a carbonaceous material, wherein the at least one second high shear device is fluidly connected with a source of a slurry comprising carbonaceous material, and a source of gasification gas or vapor, and is configured to contact the slurry with the gasification gas or vapor at a high shear rate of at least 20,000 $s^{-1}$, to produce a high shear-treated stream comprising the synthesis gas.

2. The system of claim 1, wherein the reactor is a Fischer-Tropsch reactor, a fixed-bed reactor, or a slurry reactor.

3. The system of claim 1, wherein the multifunctional catalyst also promotes alcohol synthesis.

4. The system of claim 2, wherein said multifunctional catalyst promotes both Fischer-Tropsch synthesis and alcohol synthesis reactions, or both dehydrogenation reactions and alcohol synthesis reactions.

5. The system of claim 1, wherein the high shear mixing device comprises a catalytic surface.

6. The system of claim 1, wherein the catalyst is selected from the group consisting of ruthenium carbonyl, ruthenium trichloride heptahydrate, palladium silica, and combinations thereof.

7. The system of claim 1, wherein the shear gap is in the range of from about 0.02 mm to about 5 mm.

8. The system of claim 1, wherein the at least one rotor and the at least one stator are complementarily-shaped.

9. The system of claim 1, wherein the at least one rotor is configured to provide a tip speed of at least about 23 m/sec, wherein the tip speed is defined as $\pi Dn$, where D is the diameter of the at least one rotor and n is the frequency of revolution.

10. The system of claim 1 further comprising a line for introducing the light gas into the liquid medium upstream of the at least one high shear mixing device.

11. The system of claim 10, further containing a light gas comprising carbon dioxide, methane, ethane, propane, butane, pentane, methanol, or a combination thereof.

12. The system of claim 1, further containing a light gas comprising carbon dioxide, and one or more component selected from the group consisting of methane, ethane, propane, butane, hydrogen, and combinations thereof.

13. The system of claim 1 comprising more than one high shear mixing device.

14. The system of claim 1, wherein the at least one high shear mixing device comprises at least two generators, wherein each generator comprises a rotor and a complementarily-shaped stator.

15. The system of claim 1, wherein the organic is selected from the group consisting of hydrocarbons, oxygenates, and combinations thereof.

16. The system of claim 1, wherein the organic is selected from the group consisting of C2+ hydrocarbons, alcohols, and combinations thereof.

17. The system of claim 1, wherein the light gas, the liquid medium, or both comprise a hydrogen source.

18. The system of claim 17, wherein the hydrogen source is selected from the group consisting of water, hydrogen, and simple alkanes.

19. The system of claim 18, wherein the light gas is selected from the group consisting of carbon dioxide, and simple alkanes.

20. The system of claim 1, wherein the liquid medium is selected from the group consisting of water, polyethylene glycol, and paraffinic oils.

21. The system of claim 1, wherein the liquid medium comprises water, and wherein the reactor is configured for steam stripping of organics and further comprises a water inlet line.

22. The system of claim 1, wherein the organic is selected from the group consisting of liquid oxygenates, C2+ hydrocarbons, and combinations thereof; wherein the system further contains a light gas comprising methane, carbon dioxide, or a combination thereof; and wherein the at least one high shear mixing device is operable to subject the fluid stream to a shear rate of greater than about 20,000 $s^{-1}$.

23. The system of claim 1 further containing a light gas comprising one or more gas selected from the group consisting of carbon dioxide, methane, ethane, propane, butane, pentane, methanol, and combinations thereof.

24. A system comprising:
at least one external high shear mixing device comprising at least one rotor and at least one stator separated by a shear gap, wherein the shear gap is the minimum distance between the at least one rotor and the at least one stator, wherein the at least one rotor is configured to provide a tip speed of at least about 5 m/sec, wherein the tip speed is defined as $\pi Dn$, where D is the diameter of the at least one rotor and n is the frequency of revolution;
a pump fluidly connected with a source of a gasification gas and a source of a slurry comprising a carbonaceous material, and configured for delivering the gasification gas and the slurry to the at least one external high shear mixing device, wherein the at least one external high shear mixing device is configured to form a high shear-treated stream comprising synthesis gas, wherein the high shear-treated stream comprises gasification gas bubbles having an average bubble diameter of less than about 1 μm; and
a vessel comprising at least one inlet and at least one outlet, wherein the at least one inlet of the vessel is fluidly connected to the at least one external high shear mixing device, and wherein the at least one outlet of the vessel is configured for extracting synthesis gas therefrom.

25. The system of claim 24 further comprising:
at least one second high shear mixing device comprising at least one rotor and at least one stator separated by a shear gap, wherein the shear gap is the minimum distance between the at least one rotor and the at least one stator, wherein the at least one rotor is configured to provide a tip speed of at least about 5 m/sec, wherein the tip speed is defined as $\pi Dn$, where D is the diameter of the at least one rotor and n is the frequency of revolution;
a pump configured for delivering a fluid stream comprising a mixture of a liquid medium and a light gas comprising at least a portion of the synthesis gas to the at least one second high shear mixing device, wherein the at least one second high shear mixing device is configured to form a dispersion of the light gas in the liquid medium; and
a reactor comprising at least one inlet and at least one outlet, wherein the at least one inlet of the reactor is fluidly connected to the at least one second high shear mixing device, and wherein the at least one outlet of the reactor is configured for extracting an organic produced therein from the light gas.

* * * * *